(12) United States Patent
Hyde et al.

(10) Patent No.: US 7,975,699 B2
(45) Date of Patent: Jul. 12, 2011

(54) CONDOMS CONFIGURED TO FACILITATE RELEASE OF NITRIC OXIDE

(75) Inventors: Roderick A. Hyde, Redmond, WA (US); Muriel Y. Ishikawa, Livermore, CA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 0 days.

(21) Appl. No.: 12/005,170

(22) Filed: Dec. 21, 2007

(65) Prior Publication Data
US 2009/0107512 A1    Apr. 30, 2009

Related U.S. Application Data

(63) Continuation-in-part of application No. 11/981,743, filed on Oct. 30, 2007, and a continuation-in-part of application No. 11/998,864, filed on Nov. 30, 2007, and a continuation-in-part of application No. 12/005,045, filed on Dec. 21, 2007, and a continuation-in-part of application No. 12/005,065, filed on Dec. 21, 2007, now Pat. No. 7,862,598, and a continuation-in-part of application No. 12/005,132, filed on Dec. 21, 2007, now Pat. No. 7,897,399.

(51) Int. Cl.
*A61F 6/02* (2006.01)
*A61F 5/00* (2006.01)
*A61F 5/44* (2006.01)

(52) U.S. Cl. ........ 128/844; 128/842; 128/917; 128/918; 600/38; 604/346; 604/347

(58) Field of Classification Search ................ 128/842, 128/844, 918; 600/38–41; 604/347–353
See application file for complete search history.

(56) References Cited

U.S. PATENT DOCUMENTS

| | | | |
|---|---|---|---|
| 4,162,536 A | 7/1979 | Morley | |
| 4,210,697 A | 7/1980 | Adiletta | |
| 4,248,214 A | 2/1981 | Hannah et al. | |
| 4,919,149 A | 4/1990 | Stang | |
| 5,109,871 A | 5/1992 | Thornton | |
| 5,351,698 A | 10/1994 | Wheeler et al. | |
| 5,366,997 A | 11/1994 | Keefer et al. | |
| 5,374,710 A | 12/1994 | Tsien et al. | |
| 5,405,919 A | 4/1995 | Keefer et al. | |
| 5,530,263 A | 6/1996 | DiVincenzo | |
| 5,571,152 A | 11/1996 | Chen et al. | |
| 5,580,433 A | 12/1996 | Baker et al. | |
| 5,665,077 A | 9/1997 | Rosen et al. | |
| 5,676,963 A | 10/1997 | Keefer et al. | |
| 5,683,668 A | 11/1997 | Hrabie et al. | |
| 5,690,777 A | 11/1997 | Kuethe et al. | |
| 5,736,152 A | 4/1998 | Dunn | |
| 5,765,558 A | 6/1998 | Psaros et al. | |
| 5,814,666 A | 9/1998 | Green et al. | |
| 5,858,799 A | 1/1999 | Yee et al. | |
| 5,900,433 A | 5/1999 | Igo et al. | |
| 5,910,316 A * | 6/1999 | Keefer et al. | ................ 424/433 |
| 5,943,160 A | 8/1999 | Downing | |
| 5,956,172 A | 9/1999 | Downing | |
| 5,980,705 A | 11/1999 | Allen et al. | |
| 5,994,444 A | 11/1999 | Trescony et al. | |
| 6,000,398 A | 12/1999 | Alla et al. | |
| 6,037,346 A | 3/2000 | Doherty, Jr. et al. | |
| 6,080,110 A | 6/2000 | Thorgersen | |
| 6,100,096 A | 8/2000 | Bollinger et al. | |
| 6,103,765 A | 8/2000 | Neal | |
| 6,127,363 A | 10/2000 | Doherty, Jr. et al. | |
| 6,143,314 A | 11/2000 | Chandrashekar et al. | |
| 6,149,606 A | 11/2000 | Alving et al. | |
| 6,156,753 A | 12/2000 | Doherty, Jr. et al. | |
| 6,182,661 B1 | 2/2001 | Solanki et al. | |
| 6,190,704 B1 | 2/2001 | Murrell | |
| 6,223,747 B1 | 5/2001 | Rudge et al. | |
| 6,280,604 B1 | 8/2001 | Allen et al. | |
| 6,287,601 B1 | 9/2001 | Russell | |
| 6,306,609 B1 | 10/2001 | Lai | |
| 6,308,708 B2 | 10/2001 | Strauss et al. | |
| 6,321,751 B1 | 11/2001 | Strauss et al. | |
| 6,327,074 B1 | 12/2001 | Bass et al. | |
| 6,341,607 B1 | 1/2002 | Couvreur | |
| 6,369,071 B1 | 4/2002 | Haj-Yehia | |
| 6,432,077 B1 | 8/2002 | Stenzler | |
| 6,436,470 B1 | 8/2002 | Iacocca et al. | |
| 6,440,498 B2 | 8/2002 | Schaller | |
| 6,451,337 B1 | 9/2002 | Smith et al. | |
| 6,469,051 B2 | 10/2002 | Nagano et al. | |
| 6,559,184 B2 | 5/2003 | Neal | |
| 6,621,687 B2 | 9/2003 | Lewis, Jr. et al. | |

(Continued)

FOREIGN PATENT DOCUMENTS

DE        20115123 U1 *  6/2001

(Continued)

OTHER PUBLICATIONS

"A Method of Nitric Oxide Delivery for Healing and Organ Preservation"; University of Texas at Dallas; bearing a date of May 18, 2009; p. 1; located at http://utdallas.technologypublisher.com/TechnologyProject.aspx?id=2302.
"Nanotechnology bandage speeds up healing"; Nanowerk News; Source: Akron Beacon Journal (Paula Schleis); bearing a date of Dec. 15, 2006; pp. 1-2; printed on Jul. 14, 2009; located at http://www.nanowerk.com/news/newsid=1156.php.
U.S. Appl. No. 12/008,708, Hyde et al.
U.S. Appl. No. 12/008,694, Hyde et al.
U.S. Appl. No. 12/006,090, Hyde et al.
U.S. Appl. No. 12/006,069, Hyde et al.
U.S. Appl. No. 12/006,049, Hyde et al.
Butler, P. et al.; "Cell Transplantation from Limb Allografts"; Plastic and Reconstructive Surgery; Bearing a date of Jul. 1998; pp. 161-168 (11 total pages); vol. 102, No. 1; American Society of Plastic Surgeons; located at: http://www.plasreconsurg.com; printed on Apr. 25, 2008.

(Continued)

*Primary Examiner* — Patricia M Bianco
*Assistant Examiner* — Brandon Jackson

(57) ABSTRACT

The present disclosure relates to condoms that are configured to facilitate release of nitric oxide.

20 Claims, 23 Drawing Sheets

U.S. PATENT DOCUMENTS

| | | | |
|---|---|---|---|
| 6,635,273 | B1 | 10/2003 | Loscalzo et al. |
| 6,635,415 | B1 | 10/2003 | Bollinger et al. |
| 6,636,652 | B1 | 10/2003 | Kopelman et al. |
| 6,639,007 | B2 | 10/2003 | Plamthottam |
| 6,651,667 | B2 | 11/2003 | Osterberg |
| 6,673,338 | B1 | 1/2004 | Arnold et al. |
| 6,673,871 | B2 | 1/2004 | Warneke et al. |
| 6,696,072 | B1 | 2/2004 | Podolski |
| 6,706,274 | B2 | 3/2004 | Herrmann et al. |
| 6,743,249 | B1 | 6/2004 | Alden |
| 6,747,062 | B2 | 6/2004 | Murrell |
| 6,773,714 | B2 | 8/2004 | Dunn et al. |
| 6,812,500 | B2 | 11/2004 | Reeh et al. |
| 6,818,356 | B1 | 11/2004 | Bates |
| 6,840,244 | B2 | 1/2005 | Kemp |
| 6,841,166 | B1 | 1/2005 | Zhang et al. |
| 6,900,891 | B2 * | 5/2005 | Kopelman et al. ............ 356/318 |
| 6,943,166 | B1 | 9/2005 | Pullman et al. |
| 6,983,751 | B2 | 1/2006 | Osterberg |
| 6,994,934 | B2 | 2/2006 | Stanish et al. |
| 7,052,711 | B2 | 5/2006 | West et al. |
| 7,088,040 | B1 | 8/2006 | Ducharme et al. |
| 7,105,502 | B2 | 9/2006 | Arnold et al. |
| 7,105,607 | B2 | 9/2006 | Chen |
| 7,122,046 | B2 | 10/2006 | Augustine et al. |
| 7,122,529 | B2 | 10/2006 | Ruane et al. |
| 7,144,655 | B2 | 12/2006 | Jenson et al. |
| 7,181,174 | B2 | 2/2007 | Fitzgibbon et al. |
| 7,181,261 | B2 | 2/2007 | Silver et al. |
| 7,183,001 | B1 | 2/2007 | Ederle et al. |
| 7,189,471 | B2 | 3/2007 | Jankowksi et al. |
| 7,194,801 | B2 | 3/2007 | Jenson et al. |
| 7,206,605 | B2 | 4/2007 | Hattori |
| 7,210,817 | B2 | 5/2007 | Lee et al. |
| 7,215,687 | B2 | 5/2007 | Kawai et al. |
| 7,215,887 | B2 | 5/2007 | Ternullo et al. |
| 7,217,882 | B2 | 5/2007 | Walukiewicz et al. |
| 7,218,900 | B2 | 5/2007 | Suzuki |
| 7,220,258 | B2 | 5/2007 | Myhr |
| 7,227,956 | B1 | 6/2007 | Onishi |
| 7,235,189 | B2 | 6/2007 | Höhn et al. |
| 7,235,361 | B2 | 6/2007 | Bawendi et al. |
| 7,235,505 | B2 | 6/2007 | Gromelski et al. |
| 7,236,595 | B1 | 6/2007 | Bean et al. |
| 7,238,628 | B2 | 7/2007 | Demaray et al. |
| 7,245,894 | B2 | 7/2007 | Sekiguchi et al. |
| RE39,785 | E | 8/2007 | Fuse |
| 7,253,953 | B2 | 8/2007 | Browning |
| 7,254,160 | B2 | 8/2007 | Kawamoto et al. |
| 7,256,923 | B2 | 8/2007 | Liu et al. |
| 7,257,327 | B2 | 8/2007 | Small |
| 7,260,155 | B2 | 8/2007 | Stonick et al. |
| 7,260,402 | B1 | 8/2007 | Ahmed |
| 7,260,764 | B2 | 8/2007 | Chen |
| 7,260,768 | B1 | 8/2007 | Matsumoto et al. |
| 7,261,693 | B2 | 8/2007 | Wilcox et al. |
| 7,264,602 | B1 | 9/2007 | Longsworth |
| 7,273,567 | B1 | 9/2007 | Wellinghoff et al. |
| 7,280,811 | B2 | 10/2007 | Sugiyama et al. |
| 7,283,710 | B2 | 10/2007 | Sano et al. |
| 7,294,678 | B2 | 11/2007 | McGlothlin et al. |
| 7,294,779 | B2 | 11/2007 | Watabe et al. |
| 7,295,737 | B2 | 11/2007 | Moorjani et al. |
| 7,295,741 | B2 | 11/2007 | Sako et al. |
| 7,298,605 | B2 | 11/2007 | Itoh et al. |
| 7,298,977 | B2 | 11/2007 | Ohsawa et al. |
| 7,301,751 | B2 | 11/2007 | Lee et al. |
| 7,301,754 | B1 | 11/2007 | Knowles |
| 7,303,333 | B2 | 12/2007 | Yu |
| 2002/0022046 | A1 | 2/2002 | Tedeschi et al. |
| 2002/0026937 | A1 | 3/2002 | Mault |
| 2002/0055702 | A1 * | 5/2002 | Atala et al. ..................... 604/20 |
| 2002/0068365 | A1 | 6/2002 | Kuhrts |
| 2002/0138051 | A1 | 9/2002 | Hole et al. |
| 2002/0165179 | A1 | 11/2002 | Baker, Jr. |
| 2003/0009127 | A1 | 1/2003 | Trescony et al. |
| 2003/0039697 | A1 | 2/2003 | Zhao et al. |
| 2003/0073133 | A1 | 4/2003 | Leyland-Jones |
| 2003/0077243 | A1 | 4/2003 | Fitzhugh et al. |
| 2003/0093143 | A1 | 5/2003 | Zhao et al. |
| 2003/0165578 | A1 | 9/2003 | Murrell |
| 2004/0009238 | A1 | 1/2004 | Miller et al. |
| 2004/0013747 | A1 | 1/2004 | Tucker et al. |
| 2004/0072360 | A1 | 4/2004 | Naaman et al. |
| 2004/0081580 | A1 | 4/2004 | Hole et al. |
| 2004/0193218 | A1 | 9/2004 | Butler |
| 2004/0247640 | A1 | 12/2004 | Zhao et al. |
| 2005/0079148 | A1 | 4/2005 | Fitzhugh et al. |
| 2005/0136483 | A1 | 6/2005 | Carlson |
| 2005/0181026 | A1 | 8/2005 | Davis et al. |
| 2005/0220838 | A1 | 10/2005 | Zhao et al. |
| 2005/0267090 | A1 | 12/2005 | Mascharak |
| 2006/0074282 | A1 | 4/2006 | Ward et al. |
| 2006/0134728 | A1 | 6/2006 | MacDonald et al. |
| 2006/0206171 | A1 | 9/2006 | Gertner et al. |
| 2006/0206173 | A1 | 9/2006 | Gertner et al. |
| 2006/0275350 | A1 | 12/2006 | Davis et al. |
| 2006/0280307 | A1 | 12/2006 | Ikushima et al. |
| 2007/0065473 | A1 | 3/2007 | Miller |
| 2007/0088316 | A1 | 4/2007 | Stenzler et al. |
| 2007/0148117 | A1 | 6/2007 | Davis et al. |
| 2007/0166357 | A1 | 7/2007 | Shaffer et al. |
| 2007/0181444 | A1 | 8/2007 | Bernstein et al. |
| 2007/0190122 | A1 | 8/2007 | Davis et al. |
| 2007/0208395 | A1 | 9/2007 | Leclerc et al. |
| 2007/0274874 | A1 | 11/2007 | Miller et al. |
| 2008/0069863 | A1 | 3/2008 | Peters |
| 2008/0097282 | A1 | 4/2008 | Hole et al. |
| 2008/0220048 | A1 | 9/2008 | Chen et al. |
| 2008/0281383 | A1 | 11/2008 | Butler |
| 2008/0286321 | A1 | 11/2008 | Reneker et al. |
| 2008/0311163 | A1 | 12/2008 | Peters |
| 2009/0081279 | A1 | 3/2009 | Jezek et al. |
| 2009/0202617 | A1 | 8/2009 | Ward et al. |
| 2009/0204057 | A1 | 8/2009 | Woo et al. |
| 2009/0214624 | A1 | 8/2009 | Smith et al. |
| 2010/0152683 | A1 | 6/2010 | Lindgren et al. |
| 2010/0197802 | A1 | 8/2010 | Jezek et al. |

FOREIGN PATENT DOCUMENTS

| | | | |
|---|---|---|---|
| EP | | 1 704 877 A1 | 9/2006 |
| WO | | WO 96/08966 A1 | 3/1996 |
| WO | | WO 00/53193 | 9/2000 |
| WO | | WO 01/10344 A1 | 2/2001 |
| WO | | WO 02/17898 A2 | 3/2002 |
| WO | | WO 02/057738 A2 | 7/2002 |
| WO | | WO 03/086282 A2 | 10/2003 |
| WO | | WO 2005/070008 A2 | 8/2005 |
| WO | | WO 2005/112954 A1 | 12/2005 |
| WO | | WO 2006/095193 A2 | 9/2006 |
| WO | | WO 2006/100155 A1 | 9/2006 |
| WO | | WO 2006/107122 A1 | 10/2006 |
| WO | | WO 2006/108420 A1 | 10/2006 |
| WO | | WO 2007/130702 A2 | 11/2007 |
| WO | | WO 2008/046211 A1 | 4/2008 |
| WO | | WO 2009/131931 A1 | 10/2009 |

OTHER PUBLICATIONS

Butler, A.R.; Nicholson, R.; *Life, Death and Nitric Oxide*; Bearing a date of Oct. 17, 2003; 1$^{st}$ edition; Royal Society of Chemistry; ISBN 978-0854046867 (Not Provided).

U.S. Appl. No. 12/148,284, Hyde et al.

U.S. Appl. No. 12/148,283, Hyde et al.

De Lima, R.G. et al.; "Controlled Nitric Oxide Photo-Release From Nitro Ruthenium Complexes: The Vasodilator Response Produced by UV Light Irradiation"; Inorganica Chimica Acta; Bearing a date of 2005; pp. 2643-2650; vol. 358; Elsevier B.V.; located at: http://www.sciencedirect.com.

Frank, S. et al.; "Nitric Oxide Triggers Enhanced Induction of Vascular Endothelial Growth Factor Expression in Cultured Keratinocytes (HaCaT) and During Cutaneous Wound Repair"; The FASEB Journal; Bearing a date of 1999; pp. 2002-2014; vol. 13.

Ghaffari, A. et al.; "A Direct Nitric Oxide Gas Delivery System for Bacterial and Mammalian Cell Cultures"; Nitric Oxide; Bearing a date of 2005; pp. 129-140; vol. 12; Elsevier Inc.; located at: http://www.sciencedirect.com.

Ghaffari, A. et al.; "Efficacy of Gaseous Nitric Oxide in the Treatment of Skin and Soft Tissue Infections"; Wound Repair and Regeneration; Bearing a date of 2007; pp. 368-377; vol. 15; Wound Healing Society.

Ghaffari, A. et al.; "Potential Application of Gaseous Nitric Oxide as a Topical Antimicrobial Agent"; Nitric Oxide; Bearing a date of 2006; pp. 21-29; vol. 14; Elsevier Inc.; located at: http://www.sciencedirect.com.

Goldsmith, P.C. et al.; "Inhibitors of Nitric Oxide Synthase in Human Skin"; The Journal of Investigative Dermatology; Bearing a date of Jan. 1996; pp. 113-118; vol. 106, No. 1; The Society for Investigative Dermatology, Inc.

Govers, R.; Rabelink, T.J.; "Cellular Regulation of Endothelial Nitric Oxide Synthase"; Am. J. Physiol. Renal. Physiol.; Bearing a date of 2001; pp. F193-F206; vol. 280; The American Physiological Society; located at: http://www.ajprenal.org.

Guo, H.; "Two-and Three-Photon Upconversion of LaOBr:$Er^{3+}$"; Optical Materials; Bearing a date of 2007; pp. 1840-1843; vol. 29; Elsevier B.V.; located at: http://www.sciencedirect.com.

Hassett, D.J.; Imlay, J.A.; "Bactericidal Antibiotics and Oxidative Stress: A Radical Proposal"; ACS Chemical Biology; Bearing a date of 2007; pp. 708-710; vol. 2, No. 11; located at: http://www.acschemicalbiology.org.

Miller, C.C. et al.; "Treatment of Chronic Nonhealing Leg Ulceration with Gaseous Nitric Oxide: A Case Study"; Journal of Cutaneous Medicine and Surgery; Bearing a date of Aug. 2004; pp. 233-238; vol. 8, No. 4.

Pacher, P. et al.; "Nitric Oxide and Peroxynitrite in Health and Disease"; Physiol. Rev.; Bearing a date of Jan. 2007; pp. 315-424; vol. 87; The American Physiological Society; located at: http://www.prv.org.

Patel, D.N. et al.; "Spectroscopic and Two-Photon Upconversion Studies of $Ho^{3+}$-Doped $Lu_3Al_5O_{12}$"; Optical Materials; Bearing a date of Jul. 1998; pp. 225-234; vol. 10; Elsevier Science B.V.

Rapaport, A. et al.; "Review of the Properties of Up-Conversion Phosphors for New Emissive Displays"; Journal of Display Technology; Bearing a date of Mar. 2006; pp. 68-78; vol. 2, No. 1; IEEE.

Roméro-Graillet, C. et al.; "Nitric Oxide Produced by Ultraviolet-Irradiated Keratinocytes Stimulates Melanogenesis"; J. Clin. Invest.; Bearing a date of Feb. 1997; pp. 635-642; vol. 99, No. 4; The American Society of Clinical Investigation, Inc.

Seabra, A.B. et al.; "S-Nitrosoglutathione Incorporated in Poly(Ethylene Glycol) Matrix: Potential Use for Topical Nitric Oxide Delivery"; Nitric Oxide; Bearing a date of 2004; pp. 263-272; vol. 11; Elsevier Inc.; located at: http://www.sciencedirect.com.

Shabani, M. et al.; "Enhancement of Wound Repair with a Topically Applied Nitric Oxide-Releasing Polymer"; Wound Repair and Regeneration; Bearing dates of Jul.-Sep. 1996; pp. 353-362; vol. 4, No. 3; The Wound Healing Society.

Sussman, C.; *Wound Care: A Collaborative Practice Manual*; Bearing a date of Jan. 2007; ISBN 0781774446 (Not Provided).

Suzuki, H.; Hewitt, C.W.; "Cell Transplantation from Limb Allografts: Discussion"; Plastic and Reconstructive Surgery; Bearing a date of Jul. 1998; pp. 169-170 (2 total pages); vol. 102, No. 1; American Society of Plastic Surgeons; located at: http://www.plasreconsurg.com; printed on May 2, 2008.

Tamir, S.; Tannenbaum, S.R.; "The Role of Nitric Oxide (NO) in the Carcinogenic Process"; Biochimica et Biophysica Acta; Bearing a date of 1996; pp. F31-F36; vol. 1288; Elsevier Science B.V.

Tu, H. et al.; "A Novel Electrochemical Microsensor for Nitric Oxide Based on Electropolymerized Film of o-Aminobenzaldehyde-Ethylene-Diamine Nickel"; Electroanalysis; Bearing a date of 1999; pp. 70-74; vol. 11, No. 1; Wiley-VCH.

Van Faassen, E.; Vanin, A. (Eds); *Radicals for Life: The Various Forms of Nitric Oxide*; Bearing a date of Mar. 2007; 442 pages; ISBN 978-0-444-52236-8; Elsevier (Not Provided).

Weller, R. et al.; "Antimicrobial Effect of Acidified Nitrite on Dermatophyte Fungi, *Candida* and Bacterial Skin Pathogens"; Journal of Applied Microbiology; Bearing a date of 2001; pp. 648-652; vol. 90; The Society for Applied Microbiology.

Weller, R. et al.; "Nitric Oxide Is Generated on the Skin Surface by Reduction of Sweat Nitrate"; The Journal of Investigative Dermatology; Bearing a date of Sep. 1996; pp. 327-331; vol. 107, No. 3; The Society of Investigative Dermatology, Inc.

Yamasaki, K. et al.; "Reversal of Impaired Wound Repair in iNOS-Deficient Mice by Topical Adenoviral-Mediated iNOS Gene Transfer"; J. Clin. Invest.; Bearing a date of Mar. 1998; pp. 967-971; vol. 101, No. 5; The American Society for Clinical Investigation, Inc.; located at: http://www.jci.org.

Zhelyaskov, V.R.; Godwin, D.W.; "Photolytic Generation of Nitric Oxide Through a Porous Glass Partitioning Membrane"; Nitric Oxide: Biology and Chemistry; Bearing a date of 1998; pp. 454-459; vol. 2, No. 6; Article No. NO980195; Academic Press.

"Nanotechnology—the new Viagra?"; Nanowerk News; bearing a date of Apr. 26, 2009; p. 1; located at http://www.nanowerk.com/news/newsid=10273.php.

Andrews, Karen L. et al.; "A Photosensitive Vascular Smooth Muscle Store of Nitric Oxide in Mouse Aorta: No Dependence on Expression of Endothelial Nitric Oxide Synthase"; British Journal of Pharmacology; 2003; pp. 932-940; vol. 138; Nature Publishing Group.

Bonaventura, Daniella et al.; "A Macrocyclic Nitrosyl Ruthenium Complex is a NO Donor that Induces Rat Aorta Relaxation"; Nitric Oxide; Mar. 2004; pp. 83-91 (p. 1); vol. 10, Issue 2; located at: http://www.sciencedirect.com; printed on Oct. 26, 2007 (Abstract Only).

Burrell, María A. et al.; "Detection of Nitric Oxide Synthase (NOS) in Somatostatin-Producing Cells of Human and Murine Stomach and Pancreas"; The Journal of Histochemistry and Cytochemistry; 1996; pp. 339-346; vol. 44, No. 4; The Histochemical Society, Inc.

Chmura, Antonina et al.; "The Role of Photoinduced Electron Transfer Processes in Photodegradation of the $[Fe_4(\mu_3-S)_3(NO)_7]^-$ Cluster"; Nitric Oxide; Dec. 2006; pp. 370-379 (p. 1); vol. 15, Issue 4; located at: http://www.sciencedirect.com; printed on Oct. 26, 2007 (Abstract Only).

Chen, X; Gillis, CN; "Methylene Blue Enhanced Photorelaxation in Aorta, Pulmonary Artery and Corpus Cavernosum"; Biochem. Biophys. Res. Commun.; Jan. 29, 1993; pp. 559-563 (pp. 1-2); vol. 190, No. 2; located at: http://www.pubmed.gov; printed on Oct. 26, 2007 (Abstract Only).

Dujić, Željko et al; "Aerobic Exercise Before Diving Reduces Venous Gas Bubble Formation in Humans"; J. Physiol.; 2004; pp. 637-642; vol. 555.3; The Physiological Society.

"Easy Life II"; Photon Technology International; pp. 1-3; located at: http://www.pti-nj.com/EasyLife/easylife.html; printed on Oct. 6, 2007.

Ferezin, Camila Z. et al; "The Complex Trans-$[RuCl([15]aneN_4)NO]^{2+}$ Rat Aorta Relaxation by Ultraviolet Light Irradiation"; Nitric Oxide; Nov. 2005; pp. 170-175 (p. 1); vol. 13, Issue 3; located at: http://www.sciencedirect.com; printed on Oct. 26, 2007 (Abstract Only).

Flitney, FW et al.; "Iron-Sulphur Cluster Nitrosyls, a Novel Class of Nitric Oxide Generator: Mechanism of Vasodilator Action on Rat Isolated Tail Artery"; Br. J. Pharmacol.; Nov. 1992; pp. 842-848 (pp. 1-2); vol. 107, No. 3; located at: http://www.pubmed.gov; printed on Oct. 26, 2007 (Abstract Only).

Flitney, Frederick Werner; Megson, Ian L.; "Nitric Oxide and the Mechanism of Rat Vascular Smooth Muscle Photorelaxation"; J. Physiol.; 2003; pp. 819-828; vol. 550.3; The Physiological Society.

Flitney, FW et al.; "Vasodilator Responses of Rat Isolated Tail Artery Enhanced by Oxygen-Dependent, Photochemical Release of Nitric Oxide from Iron-Sulphur-Nitrosyls"; Br. J. Pharmacol.; Apr. 1996; pp. 1549-1557 (pp. 1-2); vol. 117, No. 7; located at: http://www.pubmed.gov; printed on Oct. 26, 2007 (Abstract Only).

Fukuhara, Kiyoshi et al.; "Photochemical Generation of Nitric Oxide from 6-Nitrobenzo[a]pyrene"; J. Am. Chem. Soc.; 2001; pp. 8662-8666 (p. 1); vol. 123, No. 36; located at: http://pubs.acs.org/cgi-bin/abstract.cgi/jacsat/2001/123/i36/abs/ja0109038.html; printed on Oct. 26, 2007 (Abstract Only).

Gaston, Benjamin; "Summary: Systemic Effects of Inhaled Nitric Oxide"; Proceedings of the American Thoracic Society; 2006; pp. 170-172; vol. 3.

Gau, Jen-Jr et al.; "A MEMS Based Amperometric Detector for *E. coli* Bacteria Using Self-Assembled Monolayers"; Biosensors & Bioelectronics; 2001; pp. 745-755; vol. 16; Elsevier Science B.V.

Graham-Rowe, Duncan; "Photonic Fabrics Take Shape"; Nature Photonics; Jan. 2007; pp. 6-7; vol. 1; Nature Publishing Group.

Hardwick, J.B.J. et al.; "A Novel Method for the Delivery of Nitric Oxide Therapy to the Skin of Human Subjects Using a Semi-Permeable Membrane"; Clinical Science; 2001; pp. 395-400; vol. 100; The Biochemical Society and the Medical Research Society.

Hattenbach, Lars-Olof et al.; "Detection of Inducible Nitric Oxide Synthase and Vascular Endothelial Growth Factor in Choroidal Neovascular Membranes"; Ophthalmologica; 2002; pp. 209-214; vol. 216; S. Karger AG, Basel.

Hou, Yongchun et al.; "Nanomolar Scale Nitric Oxide Generation from Self-Assembled Monolayer Modified Gold Electrodes"; Chem. Commun.; 2000; pp. 1831-1832; The Royal Society of Chemistry.

Hrabie, Joseph A.; Keefer, Larry K.; "Chemistry of the Nitric Oxide-Releasing Diazeniumdiolate ("Nitrosohydroxylamine") Functional Group and Its Oxygen-Substituted Derivatives"; Chem. Rev.; 2002; pp. 1135-1154; vol. 102; American Chemical Society.

Ikeda, Osamu et al.; "Nitric Oxide Detection with Glassy Carbon Electrodes Coated with Charge-Different Polymer Films"; Sensors; Apr. 26, 2005; pp. 161-170; vol. 5; ISSN 1424-8220; MDPI.

"InNo-T Nitric Oxide Measurement System"; Warner Instruments; Bearing dates of 1998-2007; pp. 1-2; located at: http://www.warneronline.com/product_info.cfm?ID=220; printed on Oct. 24, 2007.

Keefer, Larry K.; "Nitric Oxide-Releasing Compounds: From Basic Research to Promising Drugs"; Chemtech; Aug. 1998; pp. 30-35 (pp. 1-8); vol. 28, No. 8; located at: http://pubs.acs.org/hotartcl/chemtech/98/aug/nitric.html; printed on Oct. 2, 2007; The American Chemical Society.

Khan, MA et al.; "The Effect of Superoxide Dismutase on Nitric Oxide-Mediated and Electrical Field-Stimulated Diabetic Rabbit Cavernosal Smooth Muscle Relaxation"; BJU Int.; Jan. 2001; pp. 98-103 (p. 1); vol. 87, No. 1; located at: http://www.pubmed.gov; printed on Sep. 27, 2007 (Abstract Only).

Kim, SC et al.; "Effects of Ultraviolet Light on the Tension of Isolated Human Cavernosal Smooth Muscle from Non-Diabetic and Diabetic Impotent Men"; Urol. Res.; 1997; pp. 149-152 (p. 1); vol. 25, No. 2; located at: http://www.pubmed.gov; printed on Sep. 27, 2007 (Abstract Only).

Kim, JH et al; "Mechanism of UV Light-Induced Photorelaxation in Isolated Rat Aorta"; J. Vet. Sci.; Dec. 2000; pp. 81-86 (p. 1); vol. 1, No. 2; located at: http://www.pubmed.gov; printed on Oct. 26, 2007 (Abstract Only).

Li, Chang Ming et al.; "Electrochemical Detection of Nitric Oxide on a SWCNT/RTIL Composite Gel Microelectrode"; Electroanalysis; 2006; pp. 713-718; vol. 18, No. 7; WILEY-VCH Verlag GmbH & Co. KGaA, Weinheim.

"Light-Emitting Diode (LED)"; Fiber Optics; Bearing a date of 2005; pp. 1-10; located at: http://www.fiber-optics.info/articles/LEDs.htm; printed on Oct. 6, 2007.

Lin, Hong-Yu et al.; "Side-Polished Multimode Fiber Biosensor Based on Surface Plasmon Resonance with Halogen Light"; Applied Optics; Feb. 10, 2007; pp. 800-806; vol. 46, No. 5; Optical Society of America.

Matthews, EK et al.; "Photon Pharmacology of an Iron-Sulphur Cluster Nitrosyl Compound Acting on Smooth Muscle"; Br. J. Pharmacol.; Sep. 1994; pp. 87-94 (p. 1); vol. 113, No. 1; located at: http://www.pubmed.gov; printed on Oct. 26, 2007 (Abstract Only).

Mendioroz, A. et al.; "Infrared to Visible and Ultraviolet Upconversion Processes in $Nd^{3+}$-Doped Potassium Lead Chloride Crystal"; Optical Materials; Sep. 2004; pp. 351-357 (p. 1); vol. 26, Issue 4; located at: http://www.sciencedirect.com; printed on Oct. 29, 2007 (Abstract Only).

Nablo, Brian J. et al.; "Inhibition of Implant-Associated Infections Via Nitric Oxide Release"; Biomaterials; Dec. 2005; pp. 6984-6990 (p. 1); vol. 26, Issue 34; located at: http://www.sciencedirect.com; printed on Oct. 26, 2007 (Abstract Only).

"NO Electrodes"; WPI-Europe-Biosensing-NO Electrodes; Bearing a date of Nov. 29, 2007; pp. 1-5; World Precision Instruments; located at: http://www.wpi-europe.com/products/biosensing/noelectrodes.htm; printed on Nov. 29, 2007.

"OL 770-LED: High-Speed LED Measurement System"; Bearing a date of 2001; pp. 1-6; located at: http://www.optroniclabs.com; Optronic Laboratories, Inc.

"Particulate Effects on Immunologic Function"; OST 1997AR; Bearing a date of 1997; pp. 1-2; located at: http://www.fda.gov/cdrh/ost/rpt97/OST1997AR9.HTML; printed on Oct. 16, 2007.

Peng, H. et al., "Ultraviolet Light-Emitting Diodes Operating in the 340 nm Wavelength Range and Application to Time-Resolved Fluorescence Spectroscopy"; Applied Physics Letters; Aug. 23, 2004; pp. 1436-1438 (p. 1); vol. 85, Issue 8; located at: http://scitation.aip.org; printed on Oct. 26, 2007 (Abstract Only).

Pou, SJ et al.; "Biological Studies of a Nitroso Compound that Releases Nitric Oxide Upon Illumination"; Molecular Pharmacology; Oct. 1, 1994; pp. 709-715 (p. 1); Vo. 46, Issue 4; located at: http://molpharm.aspetjournals.org/cgi/content/abstract/46/4/709; printed on Oct. 26, 2007 (Abstract Only).

"Probes for Nitric Oxide (NO) Research"; EMD-Calbiochem: Nitric Oxide Probes; Bearing a date of 2007; pp. 1-2; Calbiochem, Novabiochem, & Novagen; located at: http://www.emdbiosciences.com/html/cbc/nitric_oxide_probes.htm; printed on Nov. 29, 2007.

Räthel, Thomas R. et al.; "Application of 4,5-Diaminofluorescein to Reliably Measure Nitric Oxide Released from Endothelial Cells In Vitro"; Biological Procedures Online; Jun. 2, 2003; pp. 136-142; vol. 5, No. 1.

Rotta, J.C.G. et al.; "Nitric Oxide Release from the S-Nitrosothiol Zinc Phthalocyanine Complex by Flash Photolysis"; Brazilian Journal of Medical and Biological Research; 2003; pp. 587-594; vol. 36, No. 5; located at: http://www.scielo.br/pdf/bjmbr/v36n5/4604.pdf.

Seo, K.K. et al.; "Synergistic Effects of Sildenafil on Relaxation of Rabbit and Rat Cavernosal Smooth Muscles when Combined with Various Vasoactive Agents"; BJU International; 2001; pp. 596-601; vol. 88.

Singh, Ravinder Jit et al.; "Photosensitized Decomposition of S-Nitrosothiols and 2-Methyl-2-Nitrosopropane Possible Use for Site-Directed Nitric Oxide Production"; FEBS Letters; 1995; pp. 47-51; vol. 360; Federation of European Biochemical Societies.

Smith, DJ et al.; "Nitric Oxide-Releasing Polymers Containing the [N(O)NO]-Group"; J. Med. Chem.; Mar. 1, 1996; pp. 1148-1156 (p. 1); vol. 39, No. 5; located at: http://www.pubmed.gov; printed on Oct. 26, 2007 (Abstract Only).

Sonoki, T. et al.; "Detection of Inducible Nitric Oxide Synthase (iNOS) mRNA by RT-PCR in ATL Patients and HTLV-1 Infected Cell Lines: Clinical Features and Apoptosis by NOS Inhibitor"; Leukemia; 1999; pp. 713-718; vol. 13; Stockton Press.

Wadsworth, Roger et al.; "Physiologically Relevant Measurements of Nitric Oxide in Cardiovascular Research Using Electrochemical Microsensors"; Journal of Vascular Research; 2006; pp. 70-85; vol. 43; S. Karger AG, Basel.

Wang, Peng George et al.; "Nitric Oxide Donors: Chemical Activities and Biological Applications"; Chem. Rev.; 2002; pp. 1091-1134 (pp. 1-53); vol. 102, No. 4; American Chemical Society; located at: http://pubs.acs.org/cgi-bin/abstract.cgi/chreay/2002/102/i04/abs/cr0000401.html; printed on Oct. 26, 2007.

Wang, Tianlong et al.; "Inhaled Nitric Oxide in 2003: A Review of its Mechanisms of Action"; Canadian Journal of Anesthesia; 2003; pp. 839-846; vol. 50, No. 8.

Williamson, David; "Study: Nitric Oxide-Releasing Materials Might Reduce Medical Implant Infections"; UNC News Services; Sep. 7, 2001; pp. 1-2; No. 416; located at: http://www.unc.edu/news/archives/sep01/schoen090701.htm; printed on Oct. 4, 2007.

Xie, Rong-Jun; "Highly Efficient White-Light-Emitting Diodes Fabricated with Short-Wavelength Yellow Oxynitride Phosphors"; Applied Physics Letters; Mar. 6, 2006; pp. 101104.1-101104.3 (pp. 1-2); vol. 88; located at: http://scitation.aip.org/; printed on Oct. 26, 2007 (Abstract Only).

Liu et al.; "Novel Delivery System for the Bioregulatory Agent Nitric Oxide"; Chemistry of Materials; bearing a date of 2009; pp. 5032-5041; vol. 21, No. 21; © 2009 American Chemical Society.

"Nitric oxide-releasing wrap for donor organs and cloth for therapeutic socks"; e! Science News; bearing a date of Jan. 6, 2010; pp. 1-2; located at http://esciencenews.com/articles/2010/01/06/nitric.oxide.releasing.wrap.donor.organs.and.cloth.therapeutic.socks; printed on Jan. 19, 2010.

Birkeland et al.; "On The Oxidation Of Atmospheric Nitrogen in Electric Arcs"; Nature; bearing a date of 1898; pp. 98-116; No. 1,506, vol. 58.

Levine et al.; "A New, Highly Efficient Red-Emitting Cathodoluminescent Phosphor (YVO$_4$:Eu) for Color Television"; Applied Physics Letters; bearing a date of Sep. 15, 1964; pp. 1-3; vol. 5, No. 6.

Mellor, J. W.; "Modern Inorganic Chemistry"; excerpt from Modern Inorganic Chemistry; bearing a date of 1912; pp. 1-19; Longmans, Greene, and Co.

"The Shadow Mask and Aperture Grill"; The PC Guide; bearing a date of Apr. 17, 2001; pp. 1-3; © Copyright 1997-2004 Charles M. Kozierok; printed Oct. 6, 2009; located at http://www.pcguide.com/ref/crt/crtMask-c.html.

U.S. Appl. No. 12/928,029, filed Nov. 30, 2010, Hyde et al.
U.S. Appl. No. 12/928,028, filed Nov. 30, 2010, Hyde et al.
U.S. Appl. No. 12/927,610, filed Nov. 17, 2010, Hyde et al.
U.S. Appl. No. 12/930,351, Hyde et al.

Jamal, Sophie A. et al.; "Effect of Nitroglycerin Ointment on Bone Density and Strength in Postmenopausal Women"; JAMA; bearing a date of Feb. 23, 2011; pp. 800-807; vol. 305, No. 8; American Medical Association.

Khosla, Sundeep; "Is Nitroglycerin a Novel and Inexpensive Treatment for Osteoporosis?"; JAMA; bearing a date of Feb. 23, 2011; pp. 826-827; vol. 305, No. 8; American Medical Association.

Mims, Christopher; "Erectile Dysfunction Treatment to Save Soldiers' Lives"; Technology Review; bearing a date of Feb. 22, 2011; 2 pp.; MIT; located at http://www.technologyreview.com/blog/mimssbits/26427/?p1=A5.

Stubbington, Tommy; "New Condom Nears Approval"; The Wall Street Journal; Bearing a date of Apr. 20, 2011; pp. 1-2; Dow Jones & Company, Inc.

* cited by examiner

FIG. 18

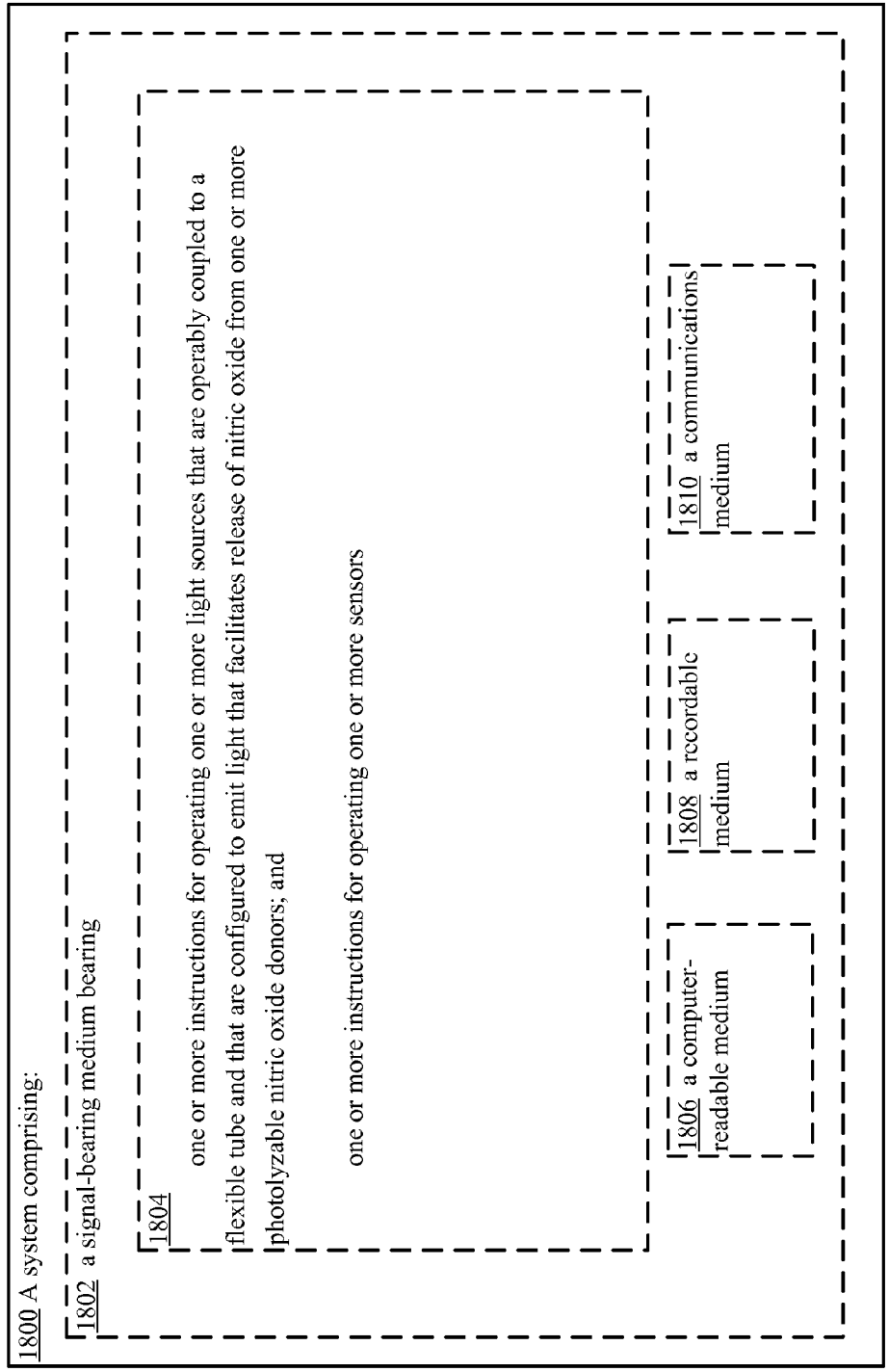

1800 A system comprising:

1802 a signal-bearing medium bearing 1804 one or more instructions for operating one or more light sources that are operably coupled to a flexible tube and that are configured to emit light that facilitates release of nitric oxide from one or more photolyzable nitric oxide donors; and one or more instructions for operating one or more sensors 1806 a computer-readable medium 1808 a recordable medium 1810 a communications medium

CONDOMS CONFIGURED TO FACILITATE RELEASE OF NITRIC OXIDE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/981,743, entitled Methods and Systems for Use of Photolyzable Nitric Oxide Donors, naming Roderick A. Hyde, Muriel Y. Ishikawa and Lowell L. Wood, Jr. as inventors, filed 30 Oct. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/998,864, entitled Systems and Devices that Utilize Photolyzable Nitric Oxide Donors, naming Roderick A. Hyde, Muriel Y. Ishikawa and Lowell L. Wood, Jr. as inventors, filed 30 Nov. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/005,045, entitled Systems and Devices Related to Nitric Oxide Releasing Materials, naming Roderick A. Hyde, Muriel Y. Ishikawa, Leif T. Stordal and Lowell L. Wood, Jr. as inventors, filed 21 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application ser. No. 12/005,065, entitled Devices and Systems that Deliver Nitric Oxide, naming Roderick A. Hyde, Muriel Y. Ishikawa, Leif T. Stordal and Lowell L. Wood, Jr. as inventors, filed 21 Dec. 2007 now U.S. Pat. No. 7,862,598, which is currently, or is an application of which a currently application is entitled to the benefit of the filing date.

For purposes of the USPTO extra-statutory requirements, the present application constitutes a continuation-in-part of U.S. patent application Ser. No. 12/005,132, entitled Nitric Oxide Sensors and Systems, naming Roderick A. Hyde, Muriel Y. Ishikawa, Leif T. Stordal and Lowell L. Wood, Jr. as inventors, filed 21 Dec. 2007 now U.S. Pat. No. 7,897,399, which is currently, or is an application of which a currently application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

The present disclosure relates to condoms that are configured to facilitate release of nitric oxide.

SUMMARY

In some embodiments one or more condoms are provided that include a flexible tube having an open end and a closed end and one or more light sources that are operably coupled to the flexible tube and that are configured to emit light that facilitates release of nitric oxide from one or more photolyzable nitric oxide donors. The condom may optionally include one or more photolyzable nitric oxide donors. The condom may optionally include one or more sensors. The condom may optionally include one or more nitric oxide permeable layers. In addition to the foregoing, other aspects are described in the claims, drawings, and text forming a part of the present disclosure.

In some embodiments one or more systems are provided that include circuitry for operating one or more light sources that are operably coupled to a flexible tube and that are configured to emit light that facilitates release of nitric oxide from one or more photolyzable nitric oxide donors. The system may optionally include circuitry for operating one or more sensors. In addition to the foregoing, other aspects are described in the claims, drawings, and text forming a part of the present disclosure.

In some embodiments one or more systems are provided that include means for operating one or more light sources that are operably coupled to a flexible tube and that are configured to emit light that facilitates release of nitric oxide from one or more photolyzable nitric oxide donors. The system may optionally include means for operating one or more sensors. In addition to the foregoing, other aspects are described in the claims, drawings, and text forming a part of the present disclosure.

In some embodiments one or more systems are provided that include a signal-bearing medium bearing one or more instructions for operating one or more light sources that are operably coupled to a flexible tube and that are configured to emit light that facilitates release of nitric oxide from one or more photolyzable nitric oxide donors. The system may optionally include one or more instructions for operating one or more sensors. In addition to the foregoing, other aspects are described in the claims, drawings, and text forming a part of the present disclosure.

In some embodiments, means include but are not limited to circuitry and/or programming for effecting the herein referenced functional aspects; the circuitry and/or programming can be virtually any combination of hardware, software, and/or firmware configured to effect the herein referenced functional aspects depending upon the design choices of the system designer. In addition to the foregoing, other system aspects means are described in the claims, drawings, and/or text forming a part of the present disclosure.

In some embodiments, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer. In addition to the foregoing, other system aspects are described in the claims, drawings, and/or text forming a part of the present application.

The foregoing summary is illustrative only and is not intended to be in any way limiting. In addition to the illustrative aspects, embodiments, and features described above, further aspects, embodiments, and features will become apparent by reference to the drawings, claims, and the following detailed description.

BRIEF DESCRIPTION OF THE FIGURES

FIG. 18 illustrates a partial view of a system 1800 that includes a computer program for executing a computer process on a computing device.

DETAILED DESCRIPTION

Figure 1:
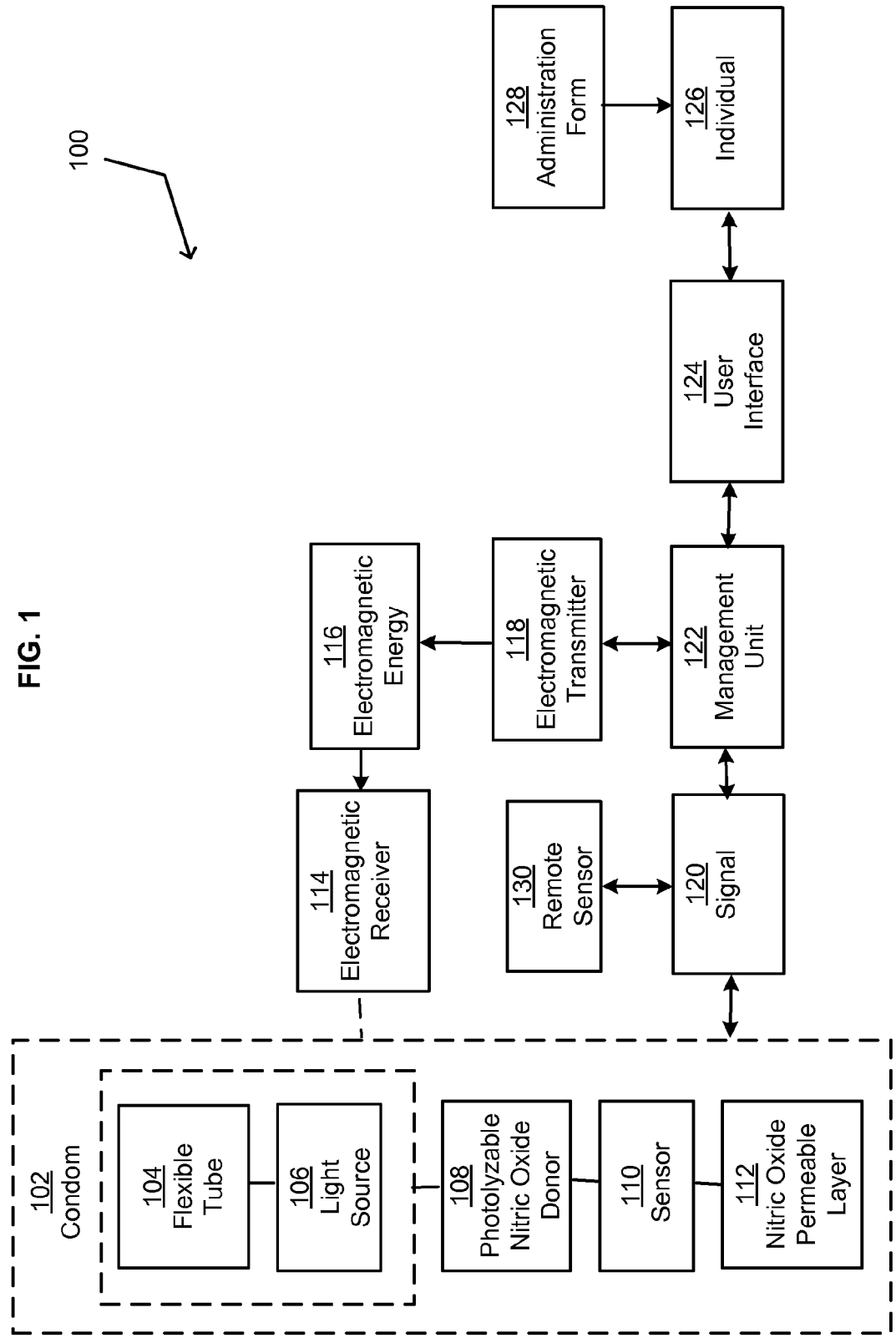
FIG. 1 illustrates an example system 100 in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

FIG. 1 illustrates a system 100 in which embodiments may be implemented. System 100 may include a condom 102 that includes a flexible tube 104 and one or more light sources 106. In some embodiments, a condom 102 may be associated with one or more photolyzable nitric oxide donors 108. In some embodiments, a condom 102 may be associated with one or more sensors 110. In some embodiments, a condom 102 may include one or more nitric oxide permeable layers 112. In some embodiments, a condom 102 may be configured to receive one or more signals 120. In some embodiments, one or more signals 120 may include instructions for operating one or more light sources 106 associated with the condom 102. In some embodiments, a condom 102 may be configured to transmit one or more signals 120. In some embodiments, system 100 may include one or more management units 122 that are configured to transmit and/or receive one or more signals 120. In some embodiments, system 100 may include one or more management units 122 that are operably associated with one or more user interfaces 124. In some embodiments, system 100 may include one or more management units 122 that are operably associated with one or more electromagnetic transmitters 118. In some embodiments, system 100 may include one or more electromagnetic transmitters 118 that transmit electromagnetic energy 116 that may be received by one or more light sources 106.

Condom

A condom 102 may be configured in numerous ways. In some embodiments, a condom 102 may include one or more light sources 106. In some embodiments, a condom 102 may include one or more photolyzable nitric oxide donors 108. In some embodiments, a condom 102 may include one or more sensors 110. In some embodiments, a condom 102 may include one or more nitric oxide permeable layers 112. In some embodiments, a condom 102 may include one or more electromagnetic receivers 114. In some embodiments, a condom 102 may be configured to receive electromagnetic energy 116 associated with one or more electromagnetic transmitters 118. In some embodiments, a condom 102 may be configured to emit light that facilitates release of nitric oxide from one or more photolyzable nitric oxide donors 108. In some embodiments, such photolyzable nitric oxide donors 108 may be systematically administered to an individual 126 to whom the condom 102 is applied. For example, in some embodiments, an individual 126 may orally administer one or more photolyzable nitric oxide donors 108 that may be photolyzed to release nitric oxide in the genital region of the individual 126 through light emitted by one or more condoms 102. In some embodiments, a condom 102 may include one or more photolyzable nitric oxide donors 108 which are applied to an individual 126 upon application of the condom 102 to the individual 126. In some embodiments, the photolyzable nitric oxide donors 108 may be formulated for penetration of the skin associated with the penis. For example, in some embodiments, one or more photolyzable nitric oxide donors 108 may be formulated within liposomes that facilitate delivery of the photolyzable nitric oxide donors 108 to the genital region of the individual 126. In some embodiments, one or more photolyzable nitric oxide donors 108 may be formulated with one or more detergents that facilitate penetration of the one or more photolyzable nitric oxide donors 108 into the genital region of the individual 126 to whom they are applied. In some embodiments, one or more light sources 106 that are associated with a condom 102 may be responsive to one or more sensors 110. In some embodiments, the one or more sensors 110 may be coupled to the condom 102. In some embodiments, the one or more sensors 110 may be separate from the condom 102. For example, in some embodiments, one or more sensors 110 may be implanted within an individual 126 that transmit one or more signals 120 that are received by one or more light sources 106 that are associated with a condom 102. Accordingly, in some embodiments, one or more light sources 106 associated with a condom 102 may be responsive to one or more remote sensors 130.

In some embodiments, a condom 102 may be associated with one or more agents. Examples, of such agents include, but are not limited to, antiviral agents, antimicrobial agents, spermicidal agents, lubricants, and the like.

Flexible Tube

System 100 may include a flexible tube 104. A flexible tube 104 may be configured to include an open end and a closed end. A flexible tube 104 may be configured in numerous ways such that it may be applied to a penis (e.g., human male penis). In some embodiments, a condom 102 may be configured to include one or more reservoirs. In some embodiments, one or more reservoirs may be configured to capture ejaculate. In some embodiments, one or more reservoirs may be configured to include one or more photolyzable nitric oxide donors 108. In some embodiments, one or more reservoirs may be configured to include one or more agents. Examples of such agents include, but are not limited to, one or more antiviral agents, one or more antimicrobial agents, one or more lubricants, one or more spermicides, and the like.

Numerous materials may be used to fabricate a flexible tube 104. In some embodiments, one type of material may be used to fabricate a flexible tube 104. In some embodiments, one or more types of material may be used to fabricate a flexible tube 104. In some embodiments, one or more types of material may be combined to fabricate a flexible tube 104. In some embodiments, an elastomeric material may be used to fabricate a flexible tube 104. In some embodiments, one or more natural materials may be used to fabricate a flexible tube 104. Examples of natural materials include, but are not limited to, skin, latex rubber, and the like. In some embodiments, one or more synthetic materials may be used to fabricate a flexible tube 104. Examples of synthetic materials include, but are not limited to, polyethylene, block copolymeric materials, and the like.

Photolyzable Nitric Oxide Donor

Numerous photolyzable nitric oxide donors 108 may be used within system 100. Examples of such photolyzable nitric oxide donors 108 include, but are not limited to, diazeniumdiolates (e.g., U.S. Pat. Nos. 7,105,502; 7,122,529; 6,673,338; herein incorporated by reference), trans-[RuCl([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550:819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference). In some embodiments, one or more photolyzable nitric oxide donors 108 may be used in association with additional nitric oxide donors that are not photolyzable. In some embodiments, one or more photolyzable nitric oxide donors 108 may be used in association with additional agents. Examples of such additional agents include, but are not limited to, enzyme inhibitors (e.g., U.S. Pat. No. 6,943,166; herein incorporated by reference), agents that increase the effects and/or concentration of nitric oxide (e.g., methylene blue and N(w)-nitro-L-arginine (L-NOARG) (see Chen and Gillis, Biochem. Biophys. Res. Commun., 190, 559-563 (1993) and Kim et al., J. Vet. Sci., 1:81-86 (2000)), L-arginine (e.g., U.S. Published Patent Application No. 20020068365 and U.S. Pat. No. 6,635,273; herein incorporated by reference), agents that stabilize nitric oxide donors (e.g., dimethly sulfoxide and ethanol), agents that increase the half life of nitric oxide (e.g., U.S. Published Patent Application No. 20030039697; herein incorporated by reference), and the like.

Nitric Oxide Permeable Layer

System 100 may include one or more nitric oxide permeable layers 112. In some embodiments, one or more nitric oxide permeable layers 112 may be included within a condom 102. In some embodiments, a condom 102 may include one or more portions that include one or more nitric oxide permeable layers 112 and one or more portions that include one or more nitric oxide impermeable layers.

In some embodiments, a condom 102 may be constructed with a nitric oxide permeable layer 112 on the interior of the condom 102 and a nitric oxide impermeable layer on the exterior of the condom 102. Accordingly, when such a condom 102 is applied to a penis, the nitric oxide permeable layer 112 is adjacent to the penis and between the penis and the nitric oxide impermeable layer. In some embodiments, one or more photolyzable nitric oxide donors 108 may be included within a space between the nitric oxide permeable layer 112 and the nitric oxide impermeable layer. Accordingly, nitric oxide released from the one or more photolyzable nitric oxide donors 108 may pass through the nitric oxide permeable layer 112 to the interior of the condom 102.

Nitric oxide permeable layers 112 may be constructed of numerous types of materials and combinations of materials. Examples of such materials include, but are not limited to, ceramics, polymeric materials, metals, plastics, and the like. In some embodiments, nitric oxide permeable layers 112 may include numerous combinations of materials. For example, in some embodiments, a nitric oxide permeable layer 112 may include a nitric oxide impermeable material that is coupled to a nitric oxide permeable material. In some embodiments, a nitric oxide permeable layer 112 may include one or more nitric oxide permeable membranes (e.g., U.S. Patent Application No. 20020026937). In some embodiments, a nitric oxide permeable layer 112 may include a selectively permeable membrane. For example, in some embodiments, a nitric oxide permeable layer 112 may include a selectively permeable membrane that is a hydrophilic polyester co-polymer membrane system that includes a copolymer with 70% polyester and 30% polyether (e.g., Sympatex™ 10 µm membrane, see Hardwick et al., Clinical Science, 100:395-400 (2001)). In some embodiments, a nitric oxide permeable layer 112 may include one or more woven materials that are permeable to nitric oxide. Accordingly, in some embodiments, a nitric oxide permeable layer 112 may include numerous types of woven glasses and/or ceramics that are permeable to nitric oxide. In some embodiments, a nitric oxide permeable layer 112 may include a porous metal portion that is permeable to nitric oxide. In some embodiments, a nitric oxide permeable layer 112 may include a nitric oxide permeable coating (e.g., U.S. Patent Application Nos. 20050220838 and 20030093143).

Light Source

Numerous light sources 106 may be used within system 100. In some embodiments, one or more light sources 106 may be used to facilitate release of nitric oxide from one or more photolyzable nitric oxide donors 108. In some embodiments, one or more light sources 106 may be configured to emit light of multiple wavelengths. In some embodiments, one or more light sources 106 may be configured to emit light that is selected to facilitate release of nitric oxide from one or more photolyzable nitric oxide donors 108. For example, in some embodiments, one or more light sources 106 may be configured to emit one or more wavelengths of light that are selected to facilitate release of nitric oxide from one or more identified photolyzable nitric oxide donors 108. In some embodiments, one or more light sources 106 may emit one or more wavelengths of light that are selected based on the absorption spectrum of one or more photolyzable nitric oxide donors 108. In some embodiments, one or more light sources 106 may emit one or more wavelengths of light that are selected based on decomposition of one or more photolyzable nitric oxide donors 108. For example, in some embodiments, one or more light sources 106 may be configured to emit one or more wavelengths of light that cause decomposition of one or more photolyzable nitric oxide donors 108 without causing injury to adjacent structures and/or tissues. In some embodiments, a first light source 106 may be configured to emit one or more wavelengths of light that cause a first photolyzable nitric oxide donor 108 to release nitric oxide and a second light source 106 may be configured to emit one or more wavelengths of light that cause a second photolyzable nitric oxide donor 108 to release nitric oxide. Accordingly, numerous light sources 106 may be coupled with numerous types of photolyzable nitric oxide donors 108 to provide for selective release of nitric oxide.

In some embodiments, one or more light sources 106 may include one or more quantum dots (e.g., U.S. Pat. No. 7,235,361). For example, in some embodiments, one or more light sources 106 may be configured to emit one or more wavelengths of light that are absorbed by one or more quantum dots. In some embodiments, one or more quantum dots may be configured to absorb light and then emit one or more wavelengths of light that cause release of nitric oxide from one or more photolyzable nitric oxide donors 108. Accordingly, in some embodiments, emission from one or more first quantum dots may be tuned to facilitate release of nitric oxide from one or more first photolyzable nitric oxide donors 108 and emission from one or more second quantum dots may be tuned to facilitate release of nitric oxide from one or more second photolyzable nitric oxide donors 108.

In some embodiments, one or more light sources 106 may be remotely controlled. For example, in some embodiments, one or more light sources 106 may be configured to receive one or more signals 120 that include instructions for operation of the one or more light sources 106. Such instructions may be associated with emission of light, non-emission of light, time when light is emitted, length of light emission, intensity of light emission, wavelengths of emitted light, and the like.

In some embodiments, light sources 106 may be configured to include one or more control units. In some embodiments, one or more light sources 106 may be configured to include a switch that may be used to turn the light source 106 on and off. For example, in some embodiments, a light source 106 may be configured to include a push button switch to turn the light source 106 on and off.

In some embodiments, one or more light sources 106 may include one or more light emitters that are coupled to one or more electromagnetic receivers 114. The one or more electromagnetic receivers 114 may be configured to couple with one or more electromagnetic transmitters 118 that produce one or more electromagnetic fields that induce an electrical current to flow in the one or more electromagnetic receivers 114 to energize the light emitters (e.g., U.S. Pat. No. 5,571,152; herein incorporated by reference). Accordingly, in some embodiments, one or more light sources 106 may be configured such that they are not directly coupled to an energy source.

A light source 106 may be configured to emit numerous types of light. In some embodiments, emitted light may be visible light. In some embodiments, emitted light may be infrared light. In some embodiments, emitted light may be ultraviolet light. In some embodiments, emitted light may be substantially any combination of visible light, infrared light, and/or ultraviolet light. In some embodiments, one or more light sources 106 may emit fluorescent light. In some embodiments, one or more light sources 106 may emit phosphorescent light.

In some embodiments, one or more light sources 106 may be configured to emit light continuously. In some embodiments, one or more light sources 106 may be configured to emit light as a pulse. In some embodiments, one or more light sources 106 may be configured to emit light as a flash. In some embodiments, one or more light sources 106 may be configured to emit light continuously, as a pulse, as a flash, or substantially any combination thereof.

In some embodiments, one or more light emitters and/or light sources 106 may be configured to provide for upconversion of energy. In some embodiments, infrared light may be upconverted to visible light (e.g., Mendioroz et al., Optical Materials, 26:351-357 (2004). In some embodiments, infrared light may be upconverted to ultraviolet light (e.g., Mendioroz et al., Optical Materials, 26:351-357 (2004). In some embodiments, one or more light sources 106 may include one or more rare-earth materials (e.g., ytterbium-erbium, ytterbium-thulium, or the like) that facilitate upconversion of energy (e.g., U.S. Pat. No. 7,088,040; herein incorporated by reference). For example, in some embodiments, one or more light sources 106 may be associated with $Nd^{3+}$ doped $KPb_2Cl_5$ crystals. In some embodiments, one or more light sources 106 may be associated with thiogallates doped with rare earths, such as $CaGa_2S_4:Ce^{3+}$ and $SrGa_2S_4:Ce^{3+}$. In some embodiments, one or more light sources 106 may be associated with aluminates that are doped with rare earths, such as $YAlO_3:Ce^{3+}$, $YGaO_3:Ce^{3+}$, $Y(Al,Ga)O_3:Ce^{3+}$, and orthosilicates $M_2SiO_5:Ce^{3+}$ (M:Sc, Y, Sc) doped with rare earths, such as, for example, $Y_2SiO_5:Ce^{3+}$. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

Electromagnetic Receiver

Numerous types of electromagnetic receivers 114 may be used within system 100. In some embodiments, one or more electromagnetic receivers 114 may be used to electromagnetically couple power to energize one or more light sources 106 from an external power supply. Methods to construct such electromagnetic receivers 114 have been described (e.g., U.S. Pat. No. 5,571,152). Briefly, in some embodiments, one or more electromagnetic receivers 114 may be associated with one or more rectifier chips. The one or more electromagnetic receivers 114 may include one or more cores about which are wrapped an electrical conductor. In some embodiments, cores may comprise a material, such as a ferrite material, due to its relatively high magnetic permeability and low magnetic hysteresis. However, other materials can be used for this purpose. In some embodiments, the electromagnetic receiver 114 may be operably coupled to a light emitting diode.

Electromagnetic Transmitter

Numerous types of electromagnetic transmitters 118 may be used within system 100. Methods to construct electromagnetic transmitters 118 have been described (e.g., U.S. Pat. No. 5,571,152). Briefly, in some embodiments, the electromagnetic transmitter 118 may include a ferrite core around which is wrapped an electrical conductor. Other types of material having high magnetic permeability and relatively low magnetic hysteresis may be used for the core. Insulating tape may be wrapped around the electrical conductor, or the electromagnetic transmitter 118 may be dipped in a resin to form a coating that stabilizes and fixes the electrical conductor on the core. A return lead from one end of the electrical conductor may include one of two leads that are coupled to an AC power supply.

Electromagnetic Energy

Electrical power may be electromagnetically coupled from one or more electromagnetic transmitters 118 with one or more electromagnetic receivers 114. Accordingly, electrical power that is transferred to the one or more electromagnetic receivers 114 may be used to power one or more light emitters. Methods and devices that may be used to transmit electrical power to a light emitter have been described (e.g., U.S. Pat. No. 5,571,152).

Sensor

Numerous types of sensors 110 may be used within system 100. In some embodiments, a condom 102 may include one or more sensors 110. In some embodiments, a sensor 110 may include one or more nitric oxide sensors 110 that are configured for implantation into an individual 126 (e.g., U.S. Pat. No. 7,181,261). For example, in some embodiments, one or more sensors 110 may be configured to be implanted into the genital region of an individual 126. Accordingly, in some embodiments, one or more sensors 110 may be used to determine the presence of nitric oxide in one or more tissues. In some embodiments, a sensor 110 may be configured for use on the outside surface of an individual 126. For example, in some embodiments, one or more sensors 110 may be configured to detect the concentration of nitric oxide on the surface of skin. In some embodiments, a sensor 110 may be configured to utilize fluorescence to detect nitric oxide. For example, in some embodiments, a sensor 110 may detect nitric oxide through use of one or more fluorescent probes, such as 4,5-diaminofluorescein diacetate (EMD Chemicals Inc., San Diego, Calif.). In some embodiments, a sensor 110 may detect nitric oxide through use of one or more electrodes. For example, in some embodiments, a sensor 110 may utilize an electrode that includes a single walled carbon nanotube and an ionic liquid to detect nitric oxide (e.g., Li et al., Electroanalysis, 18:713-718 (2006)). Numerous sensors 110 are commercially available and have been described (e.g., World Precision Instruments, Inc., Sarasota, Fla., USA; U.S. Pat. Nos. 6,100,096; 6,280,604; 5,980,705).

In some embodiments, one or more sensors 110 may be configured to detect one or more nitric oxide synthases. In some embodiments, one or more sensors 110 may be configured to detect nitric oxide synthase activity. Nitric oxide synthase detection kits are commercially available (e.g., Cell Technology, Inc., Mountain View, Calif.). In some embodiments, one or more sensors 110 may be configured to detect nitric oxide synthase messenger ribonucleic acid (mRNA). Methods that may be used to detect such mRNA have been reported (e.g., Sonoki et al., Leukemia, 13:713-718 (1999)). In some embodiments, one or more sensors 110 may be configured to detect nitric oxide synthase through immunological methods. Methods that may be used to detect nitric oxide synthase been reported (e.g., Burrell et al., J. Histochem. Cytochem., 44:339-346 (1996) and Hattenbach et al., Ophthalmologica, 216:209-214 (2002)). In some embodiments, micro-electro-mechanical systems may be used to detect nitric oxide synthase. In some embodiments, antibodies and/or aptamers that bind to nitric oxide synthase may be used within one or more micro-electro-mechanical systems to detect nitric oxide synthase. Methods to construct micro-electro-mechanical detectors have been described (e.g., Gau et al., Biosensors 1070 & Bioelectronics, 16:745-755 (2001)). Accordingly, sensors 110 may be configured in numerous ways to detect one or more nitric oxide synthases.

In some embodiments, one or more sensors 110 may be configured to detect one or more nitric oxide donors. In some embodiments, one or more sensors 110 may include one or more surface plasmon resonance chemical electrodes that are configured to detect one or more nitric oxide donors. For example, in some embodiments, one or more sensors 110 may include one or more surface plasmon resonance chemical electrodes that include antibodies and/or aptamers that bind to one or more nitric oxide donors. Accordingly, such electrodes may be used to detect the one or more nitric oxide donors through use of surface plasmon resonance. Methods to construct surface plasmon resonance chemical electrodes are known and have been described (e.g., U.S. Pat. No. 5,858, 799; Lin et al., Applied Optics, 46:800-806 (2007)). In some embodiments, antibodies and/or aptamers that bind to one or more nitric oxide donors may be used within one or more micro-electro-mechanical systems to detect one or more nitric oxide donors. Methods to construct micro-electro-mechanical detectors have been described (e.g., Gau et al., Biosensors & Bioelectronics, 16:745-755 (2001)).

In some embodiments, one or more sensors 110 may be configured to detect strain. For example, in some embodiments, one or more sensors 110 may include one or more strain gauges. In some embodiments, one or more sensors 110 may be configured to detect penile rigidity. In some embodiments, one or more sensors 110 may be configured to detect blood pressure. In some embodiments, one or more sensors 110 may include one or more transmitters. Accordingly, in some embodiments, one or more sensors 110 may transmit one or more signals 120 to which one or more light sources 106 that are associated with a condom 102 will respond.

Transmitter

The system 100 may include one or more transmitters. In some embodiments, a condom 102 may include one or more transmitters that transmit one or more signals 120 that are received by one or more management units 122. In some embodiments, system 100 may include one or more transmitters that transmit one or more signals 120 that are received by one or more condoms 102. Numerous types of transmitters may be used in association with system 100. Examples of such transmitters include, but are not limited to, transmitters that transmit one or more optical signals 120, radio signals 120, wireless signals 120, hardwired signals 120, infrared signals 120, ultrasonic signals 120, acoustic signals 120, and the like (e.g., U.S. Pat. Nos. RE39,785; 7,260,768; 7,260,764; 7,260,402; 7,257,327; 7,215,887; 7,218,900; herein incorporated by reference). In some embodiments, one or more transmitters may transmit one or more signals 120 that are encrypted. Numerous types of transmitters are known and have been described (e.g., U.S. Pat. Nos. and Published U.S. Patent Application: 7,236,595; 7,260,155; 7,227,956; US2006/0280307; herein incorporated by reference).

Management Unit

System 100 may include one or more management units 122. In some embodiments, one or more management units 122 may be associated with one or more condoms 102. For example, in some embodiments, one or more management units 122 may be configured to regulate the operation of one or more light sources 106 that are associated with a condom 102. In some embodiments, one or more management units 122 may be configured to receive one or more signals 120 from one or more sensors 110 that are associated with a condom 102. In some embodiments, one or more management units 122 may be configured to receive one or more signals 120 from one or more light sources 106 that are associated with a condom 102. Accordingly, in some embodiments, one or more management units 122 may be used to regulate the operation of one or more light sources 106 associated with a condom 102. In some embodiments, a management unit 122 may include memory. In some embodiments, a management unit 122 may include one or more programs that provide instructions for controlling a condom 102.

Receiver

System 100 may include one or more receivers. In some embodiments, one or more receivers may be associated with a condom 102. In some embodiments, one or more receivers may be associated with one or more light sources 106. In some embodiments, one or more receivers may be associated with one or more sensors 110. Numerous types of receivers may be used in association with system 100. Examples of such receivers include, but are not limited to, receivers that receive one or more optical signals 120, radio signals 120, wireless signals 120, hardwired signals 120, infrared signals 120, ultrasonic signals 120, acoustic signals 120, and the like. Such receivers are known and have been described (e.g., U.S. Pat. Nos. RE39,785; 7,218,900; 7,254,160; 7,245,894; 7,206, 605; herein incorporated by reference).

Signal

Numerous types of signals 120 may be used in association with system 100. Examples of such signals 120 include, but are not limited to, optical signals 120, radio signals 120, wireless signals 120, hardwired signals 120, infrared signals 120, ultrasonic signals 120, and the like. In some embodiments, one or more signals 120 may not be encrypted. In some embodiments, one or more signals 120 may be encrypted. In some embodiments, one or more signals 120 may be sent through use of a secure mode of transmission. In some embodiments, one or more signals 120 may be coded for receipt by a specific individual 126. In some embodiments, such code may include anonymous code that is specific for an individual 126. Accordingly, information included within one or more signals 120 may be protected against being accessed by others who are not the intended recipient.

Individual

A condom 102 may be used to deliver nitric oxide to an individual 126. In some embodiments, an individual 126 may be a human. In some embodiments, an individual 126 may be a human male. In some embodiments, a condom 102 may be used to deliver nitric oxide to an individual 126 to treat sexual dysfunction. In some embodiments, a condom 102 may be used to treat male erectile disorder. In some embodiments, sexual dysfunction may be due to a physical condition. For example, in some embodiments, sexual dysfunction may result from surgery, a physical injury, pharmaceutical use, age, or the like. In some embodiments, sexual dysfunction may be due to a mental condition. For example, in some embodiments, sexual dysfunction may be due to depression, lack of interest, insecurity, anxiety, or the like. In some embodiments, a condom 102 may deliver nitric oxide to increase sexual performance and/or pleasure.

Administration Form

Numerous types of administration forms 128 may be used to provide one or more photolyzable nitric oxide donors 108 to an individual 126. In some embodiments, an administration form 128 may be a formulation of one or more photolyzable nitric oxide donors 108. In some embodiments, an administration form 128 may be configured for oral delivery of one or more photolyzable nitric oxide donors 108 to an individual 126. For example, in some embodiments, an administration form 128 may be configured as a pill, a lozenge, a capsule, a liquid, and the like. In some embodiments, an administration form 128 may be configured for topical delivery of one or more photolyzable nitric oxide donors 108 to an individual 126. For example, in some embodiments, an administration form 128 may be configured as a gel, a cream, a lotion, a lubricant, a jelly, and the like. In some embodiments, one or more photolyzable nitric oxide donors 108 may be formulated with one or more liposomes to provide for delivery of the one or more photolyzable nitric oxide donors 108 to the individual 126. In some embodiments, one or more photolyzable nitric oxide donors 108 may be formulated with one or more detergents to facilitate delivery of the one or more photolyzable nitric oxide donors 108 to the individual 126. In some embodiments, one or more photolyzable nitric oxide donors 108 may be formulated with one or more agents that stabilize the one or more photolyzable nitric oxide donors 108. In some embodiments, one or more photolyzable nitric oxide donors 108 may be formulated for administration to one or more individuals 126 through inhalation. In some embodiments, one or more photolyzable nitric oxide donors 108 may be formulated for administration to an individual 126 through parenteral administration.

In some embodiments, an administration form 128 may include an implant. In some embodiments, one or more photolyzable nitric oxide donors 108 may be coupled to a structure that can be implanted within an individual 126. For example, in some embodiments, one or more photolyzable nitric oxide donors 108 may be coupled to a polymeric structure for implantation into an individual 126 (e.g., U.S. Pat. Nos. 5,405,919; 6,451,337; 7,052,711: herein incorporated by reference, Smith et al., J. Med. Chem., 1:1148-1156 (1996)). In some embodiments, one or more photolyzable nitric oxide donors 108 may be included within a porous structure and/or matrix for implantation into an individual 126 (e.g., U.S. Published Patent Application No. 20030039697; herein incorporated by reference). Such structures may be constructed from numerous materials that include, but are not limited to, polymers, ceramics, metals, and the like. In some embodiments, one or more photolyzable nitric oxide donors 108 may be formulated for depot administration to an individual 126. For example, in some embodiments, one or more photolyzable nitric oxide donors 108 may be formulated with one or more biodegradable materials that degrade within an individual 126 to release the one or more photolyzable nitric oxide donors 108 (e.g., U.S. Pat. Nos. 5,736,152; 6,143,314; 6,773,714; herein incorporated by reference). Accordingly, in some embodiments, one or more photolyzable nitric oxide donors 108 may be included within a flowable material that forms an implant upon being injected into an individual 126.

In some embodiments, one or more photolyzable nitric oxide donors 108 may be formulated with one or more additional agents. Examples of such agents include, but are not limited to, enzyme inhibitors, additional nitric oxide donors, free radical scavengers, and the like. In some embodiments, one or more photolyzable nitric oxide donors 108 may be associated with one or more light sources 106 (e.g., U.S. Pat. No. 5,571,152; herein incorporated by reference). In some embodiments, one or more photolyzable nitric oxide donors 108 may be formulated with one or more quantum dots (e.g., U.S. Pat. No. 7,235,361; herein incorporated by reference).

User Interface/User

System 100 may include numerous types of user interfaces 124. For example, one or more users (e.g., individuals 126) may interact through use of numerous user interfaces 124 that utilize hardwired methods, such as through use of an on/off switch, a push button, a keyboard, and the like. In some embodiments, the user interface 124 may utilize wireless methods, such as methods that utilize a transmitter and receiver, utilize the internet, and the like.

Figure 2:
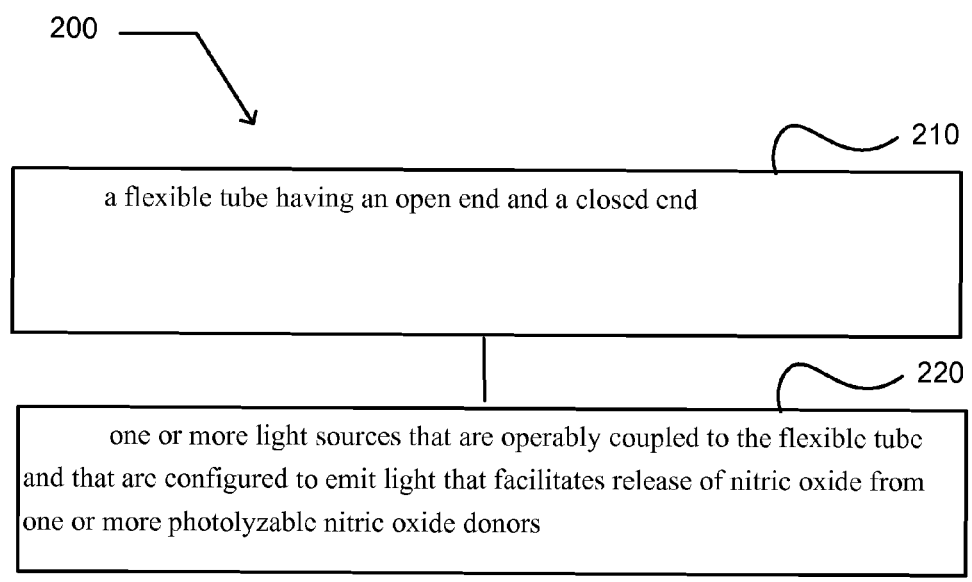
FIG. 2 illustrates embodiment 200 of condom 102 within system 100.

FIG. 2 illustrates embodiment 200 of condom 102 within system 100. In FIG. 2, discussion and explanation may be provided with respect to the above-described example of FIG. 1, and/or with respect to other examples and contexts. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 200 may include module 210 that includes a flexible tube having an open end and a closed end. In some embodiments, a condom 102 may include a flexible tube 104 having an open end and a closed end. In some embodiments, a flexible tube 104 may include one layer of elastomeric material. In some embodiments, a flexible tube 104 may include one or more layers of elastomeric material. For example, in some embodiments, a flexible tube 104 may be constructed of a single layer of latex rubber. In some embodiments, a flexible tube 104 may be constructed of a single layer of polyethylene. In some embodiments, a flexible tube 104 may be constructed of two or more laminated layers. For example, in some embodiments, a flexible tube 104 may include an inner layer that is constructed from polyethylene and an outer layer that is made from latex and laminated onto the inner layer. In some embodiments, a flexible tube 104 may include an inner layer that is a nitric oxide permeable layer 112 and an outer layer that is a nitric oxide impermeable layer. In some embodiments, a flexible tube 104 may include an inner layer that is a nitric oxide permeable layer, an outer layer that is a nitric oxide impermeable layer, and one or more photolyzable nitric oxide donors 108 positioned between the inner layer and the outer layer. In some embodiments, a flexible tube 104 may include one or more spermicidal agents. In some embodiments, one or more spermicidal agents may be associated with one or more portions of an interior surface of a flexible tube 104. In some embodiments, one or more spermicidal agents may be associated with one or more portions of an exterior surface of a flexible tube 104. In some embodiments, one or more spermicidal agents may be associated with one or more portions of an interior surface and one or more portions of an external surface of a flexible tube 104. In some embodiments, a flexible tube 104 may include one or more antimicrobial agents. In some embodiments, one or more antimicrobial agents may be associated with one or more portions of an interior surface of a flexible tube 104. In some embodiments, one or more antimicrobial agents may be associated with one or more portions of an exterior surface of a flexible tube 104. In some embodiments, one or more antimicrobial agents may be associated with one or more portions of an interior surface and one or more portions of an external surface of a flexible tube 104. In some embodiments, a flexible tube 104 may include one or more antiviral agents. In some embodiments, one or more antiviral agents may be associated with one or more portions of an interior surface of a flexible tube 104. In some embodiments, one or more antiviral agents may be associated with one or more portions of an exterior surface of a flexible tube 104. In some embodiments, one or more antiviral agents may be associated with one or more portions of an interior surface and one or more portions of an external surface of a flexible tube 104.

A flexible tube 104 may be constructed through use of numerous processes. For example, in some embodiments, a flexible tube 104 may be constructed through a dipping process where a former is coated with one or more elastomeric materials. In some embodiments, a flexible tube 104 may be constructed through a spraying process where a former is spray coated with one or more elastomeric materials. In some embodiments, a flexible tube 104 may be constructed through a molding process where one or more elastomeric materials are introduced into a mold and cast into a flexible tube 104. Accordingly, numerous processes may be used to construct flexible tubes 104. In some embodiments, one or more light sources 106 may be applied to a form and then the form may be coated with one or more elastomeric materials to form a flexible tube 104 that is associated with one or more light sources 106. In some embodiments, one or more light sources 106 may be associated with a preformed flexible tube 104. Methods that may be used to construct a flexible tube 104 are known and have been described (e.g., U.S. Pat. Nos. 7,235, 505; 6,983,751; 6,651,667; 6,308,708; 6,000,398; and 4,919, 149).

The embodiment 200 may include module 220 that includes one or more light sources that are operably coupled to the flexible tube and that are configured to emit light that facilitates release of nitric oxide from one or more photolyzable nitric oxide donors. In some embodiments, a condom 102 may include one or more light sources 106 that are operably coupled to a flexible tube 104 and that are configured to emit light that facilitates release of nitric oxide from one or more photolyzable nitric oxide donors 108. A light source 106 may be configured in numerous ways. For example, in some embodiments, a light source 106 may include a chemiluminescent light source 106. In some embodiments, a light source 106 may include a phosphorescent light source 106. In some embodiments, a light source 106 may include a light emitter that is coupled to a power supply. For example, in some embodiments, a light source 106 may include one or more light emitting diodes that are coupled to one or more power supplies. Examples of power supplies include, but are not limited to, capacitors, batteries, electromagnetic receivers 114, and the like. In some embodiments, one or more light sources 106 may be configured to emit light that specifically facilitates release of nitric oxide from one or more photolyzable nitric oxide donors 108. For example, in some embodiments, one or more light sources 106 may be configured to emit one or more wavelengths of light that facilitate photodecomposition of one or more photolyzable nitric oxide donors 108. In some embodiments, one or more light sources 106 may be configured such that they do not emit one or more wavelengths of light that do not facilitate photodecomposition of one or more photolyzable nitric oxide donors 108. Accordingly, in some embodiments, one or more light sources 106 may be configured to emit light that is matched to one or more photolyzable nitric oxide donors 108 and causes photodecomposition of the one or more photolyzable nitric oxide donors 108. In some embodiments, one or more light sources 106 may be configured such that they do not emit light that cross-links biological structures (e.g., proteins) or that causes the formation of DNA adducts. Accordingly, in some embodiments, one or more light sources 106 may be configured to emit light that photolyzes one or more photolyzable nitric oxide donors 108 with reduced damage to surrounding tissue. For example, in some embodiments, one or more light sources 106 may be configured to emit visible light ($\lambda$=550 nm) to facilitate homolytic decomposition of S-nitrosoglutathione to generate nitric oxide (e.g., Singh et al., FEBS Letters, 360:47-51 (1995)). In some embodiments, ultraviolet light may be used to facilitate release of nitric oxide from one or more photolyzable nitric oxide donors 108. For example, in some embodiments, one or more light sources 106 may be configured to emit ultraviolet light ($\lambda$=355 nm) to release nitric oxide from S-nitrosothiols (e.g., Rotta et al., Braz. J. Med. Biol. Res., 36:587-594 (2003)). In some embodiments, one or more light sources 106 may be configured to emit light over a broad range of wavelengths that will facilitate release of nitric oxide from one or more photolyzable nitric oxide donors 108. For example, in some embodiments, $O^2$-benzyl substituted diazeniumdiolates, $O^2$-napthylmethyl substituted diazeniumdiolates, and/or $O^2$-napththylallyl substituted diazeniumdiolates may be photolyzed by light over a broad range of wavelengths ($\lambda$=254 nm to $\lambda$=700 nm) (e.g., U.S. Pat. No. 7,122,529).

Figure 3:
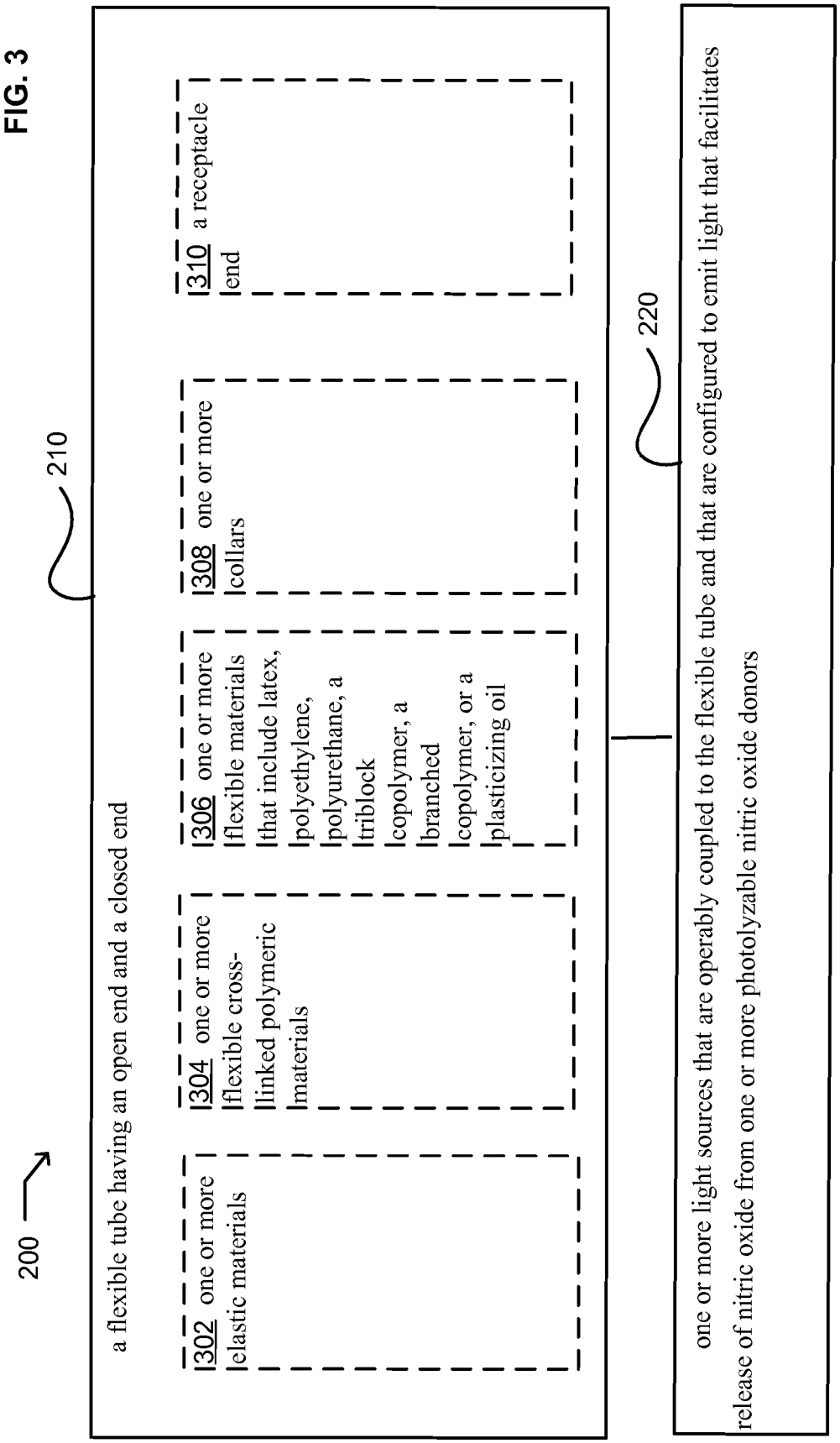
FIG. 3 illustrates alternate embodiments of module 210 of embodiment 200 of condom 102 within system 100.

FIG. 3 illustrates alternative embodiments of embodiment 200 of condom 102 within system 100 of FIG. 2. FIG. 3 illustrates example embodiments of module 210 of condom 102. Additional embodiments may include an embodiment 302, an embodiment 304, an embodiment 306, an embodiment 308, and/or an embodiment 310.

At embodiment 302, module 210 may include one or more elastic materials. In some embodiments, a flexible tube 104 may include one or more elastic materials. Numerous types of elastic materials may be used to construct a flexible tube 104. Examples of such elastic materials include, but are not limited to, polyurethanes (e.g., polyester based polyurethanes), polyesters, polybutadienes and copolymers thereof, latex, natural rubbers, natural skins, and/or substantially any combination thereof (e.g., U.S. Pat. No. 5,351,698).

At embodiment 304, module 210 may include one or more flexible cross-linked polymeric materials. In some embodiments, a flexible tube 104 may include one or more flexible cross-linked polymeric materials. In some embodiments, a flexible tube 104 may include polynitrile oxide crosslinked rubber (e.g., U.S. Pat. No. 7,294,678). For example, in some embodiments, such cross-linked rubber may be natural rubber or synthetic cis-1,4-polyisoprene rubber that is crosslinked with a polynitrile oxide crosslinking agent. In some embodiments, a flexible tube 104 may include a synthetic polymer that is cross-linked with a metal oxide cross-linking agent. Examples of such cross-linking agents include, but are not limited to, zinc oxide, magnesium oxide, cadmium oxide, and the like. Examples of synthetic polymers that may be cross-linked with a metal oxide cross-linking agent include, but are not limited to, BARRIERPRO BP 2000 (Riechold Chemicals, Inc., North Carolina, USA) (e.g., U.S. Pat. No. 6,673,871). Accordingly, a flexible tube 104 may be fabricated from numerous types of cross-linked polymeric materials.

At embodiment 306, module 210 may include one or more flexible materials that include latex, polyethylene, polyurethane, a triblock copolymer, a branched copolymer, or a plasticizing oil. In some embodiments, a flexible tube 104 may include one or more flexible (e.g., elastomeric) materials that include latex, polyethylene, polyurethane, a triblock copolymer, a branched copolymer, a plasticizing oil, and/or substantially any combination thereof (e.g., U.S. Pat. No. 7,105,607). In some embodiments, a tyrene-ethylene-butylene-styrene block copolymer may be used to fabricate a flexible tube 104 (e.g., U.S. Pat. No. 6,639,007).

At embodiment 308, module 210 may include one or more collars. In some embodiments, a flexible tube 104 may include one or more collars. In some embodiments, a flexible tube 104 may include one or more collars that are configured to form a seal around a penis when the flexible tube 104 is applied to the penis. For example, in some embodiments, one or more collars may be configured to form a seal around the base of a penis to which the flexible tube 104 is applied to facilitate retention of nitric oxide released within the flexible tube 104 next to the enclosed penis. In some embodiments, one or more collars may be associated with one or more adhesives to facilitate association of a flexible tube 104 with a penis to which the flexible tube 104 is applied. In some embodiments, one or more collars may be associated with one or more light sources 106. For example, in some embodiments, one or more collars may include one or more light emitters. In some embodiments, one or more collars may include one or more power supplies. In some embodiments, one or more collars may include one or more electromagnetic receivers 114. In some embodiments, one or more collars may be associated with one or more photolyzable nitric oxide donors 108. For example, in some embodiments, one or more collars may include one or more reservoirs that are configured to contain one or more photolyzable nitric oxide donors 108 and/or compositions that include one or more photolyzable nitric oxide donors 108. In some embodiments, one or more collars may be associated with one or more sensors 110. In some embodiments, one or more collars may be associated with one or more control units.

At embodiment 310, module 210 may include a receptacle end. In some embodiments, a flexible tube 104 may include a receptacle end. In some embodiments, a receptacle end may be configured to receive ejaculate. In some embodiments, a receptacle end may be configured to contain one or more spermicidal agents. In some embodiments, a receptacle end may be configured to contain one or more antimicrobial agents. In some embodiments, a receptacle end may be configured to contain one or more antiviral agents. In some embodiments, a receptacle end may be configured to contain one or more photolyzable nitric oxide donors 108.

Figure 4:
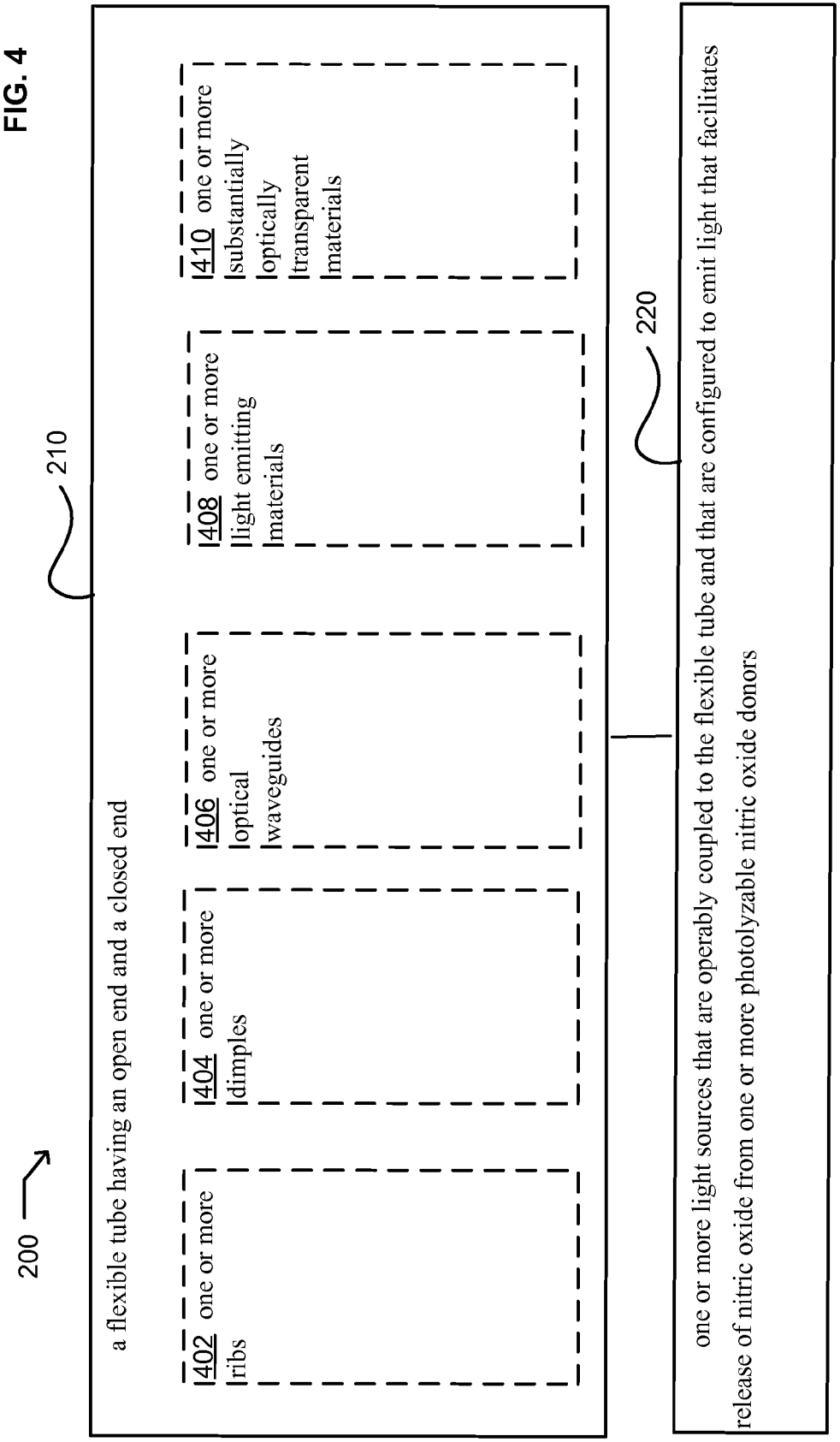
FIG. 4 illustrates alternate embodiments of module 210 of embodiment 200 of condom 102 within system 100.

FIG. 4 illustrates alternative embodiments of embodiment 200 of condom 102 within system 100 of FIG. 2. FIG. 4 illustrates example embodiments of module 210 of condom 102. Additional embodiments may include an embodiment 402, an embodiment 404, an embodiment 406, and/or an embodiment 408.

At embodiment 402, module 210 may include one or more ribs. In some embodiments, a flexible tube 104 may include one or more ribs (e.g., U.S. Pat. Nos. 6,308,708 and 5,109,871). In some embodiments, a flexible tube 104 may include spiral crisscross ribbing (e.g., U.S. Pat. No. 6,321,751). A flexible tube 104 may include one or more ribs that are configured in numerous ways. In some embodiments, one or more light emitters may be included within the one or more ribs. For example, in some embodiments, fiber optic fibers may be associated with a flexible tube 104 to form ribbing on the flexible tube 104. In some embodiments, fiber optic fibers may be associated with a flexible tube 104 by applying one or more flexible materials to a form to produce a flexible tube 104 and then applying fiber optic fibers to the flexible tube 104. In some embodiments, fiber optic fibers may be associated with a flexible tube 104 by applying one or more flexible materials to a form to produce a flexible tube 104, applying fiber optic fibers to the flexible tube 104, and then covering the fiber optic fibers with another layer of flexible material. In some embodiments, one or more fiber optic fibers may be applied to a form that is then coated with one or more flexible materials to form a flexible tube 104 that is associated with the one or more optical fibers. In some embodiments, a flexible tube 104 may be associated with one or more ribs that are configured to provide for passage of gases, fluids, gels, and the like (e.g., configured to include one or more tubes). Accordingly, in some embodiments, one or more ribs may be configured to provide channels that facilitate delivery of one or more photolyzable nitric oxide donors 108 to locations associated with the flexible tube 104. In some embodiments, one or more ribs may be configured to provide channels that facilitate delivery of nitric oxide to locations associated with the flexible tube 104.

At embodiment 404, module 210 may include one or more dimples. In some embodiments, a flexible tube 104 may include one or more dimples (e.g., U.S. Pat. No. 6,440,498). In some embodiments, one or more dimples may be associated with one or more light sources 106. For example, in some embodiments, one or more light emitting diodes that are coupled with an electromagnetic receiver 114 may be associated with one or more dimples (e.g., U.S. Pat. No. 5,571,152). In some embodiments, one or more dimples may be configured as one or more reservoirs for one or more photolyzable nitric oxide donors 108. In some embodiments, one or more dimples may be configured as one or more reservoirs for one or more antiviral agents. In some embodiments, one or more dimples may be configured as one or more reservoirs for one or more antimicrobial agents.

At embodiment 406, module 210 may include one or more optical waveguides. In some embodiments, a flexible tube 104 may include one or more optical waveguides. Such waveguides may be configured to associate with one or more light sources 106. Numerous types of optical waveguides may be associated a flexible tube 104. For example, in some embodiments, a waveguide may be an optical fiber waveguide. In some embodiments, a waveguide may be a rectangular waveguide. In some embodiments, a waveguide may be a dielectric slab waveguide. In some embodiments, optical waveguides may include, but are not limited to, planar waveguides, strip waveguides, and/or fiber waveguides. In some embodiments, an optical waveguide may have a single-mode structure. In some embodiments, an optical waveguide may have a multi-mode structure. In some embodiments, an optical waveguide may exhibit a step refractive index distribution. In some embodiments, an optical waveguide may exhibit a gradient refractive index distribution. An optical waveguide may be constructed from numerous types of materials that include, but are not limited to, glass, polymers, semiconductors, and the like. Methods to construct optical waveguides have been described (e.g., U.S. Pat. No. 7,283,710).

At embodiment 408, module 210 may include one or more light emitting materials. In some embodiments, a flexible tube 104 may include one or more light emitting materials. In some embodiments, a flexible tube 104 may be constructed entirely of one or more light emitting materials. In some embodiments, a flexible tube 104 may be constructed partially of one or more light emitting materials. In some embodiments, a flexible tube 104 may include one or more portions that include one or more light emitting materials and one or more portions that are not made of light emitting materials. A flexible tube 104 may include numerous types of light emitting materials. In some embodiments, a light emitting material may include a light-emitting diode. In some embodiments, a light emitting material may include an organic light-emitting diode. In some embodiments, an organic light-emitting diode may be a light-emitting diode having an emissive electroluminescent layer that includes a film of organic compounds. In some embodiments, a flexible tube 104 may include one or more light-emitting polymers. In some embodiments, a light-emitting polymer may include one or more derivatives of poly(p-phenylene vinylene). In some embodiments, a light-emitting polymer may include one or more derivatives of poly(fluorene). In some embodiments, a polymeric backbone may be substituted with different side chains to determine the color of light emitted by the light-emitting polymer.

At embodiment 408, module 210 may include one or more substantially optically transparent materials. In some embodiments, a flexible tube 104 may include one or more substantially optically transparent materials. In some embodiments, a substantially optically transparent material may allow multiple wavelengths of light to pass through the material. In some embodiments, a substantially optically transparent material may allow visible light to pass through the material. In some embodiments, a substantially optically transparent material may allow ultraviolet light to pass through the material. In some embodiments, a substantially optically transparent material may allow infrared light to pass through the material. In some embodiments, a substantially optically transparent material may allow ultraviolet light, visible light, and infrared light to pass through the material.

Figure 5:
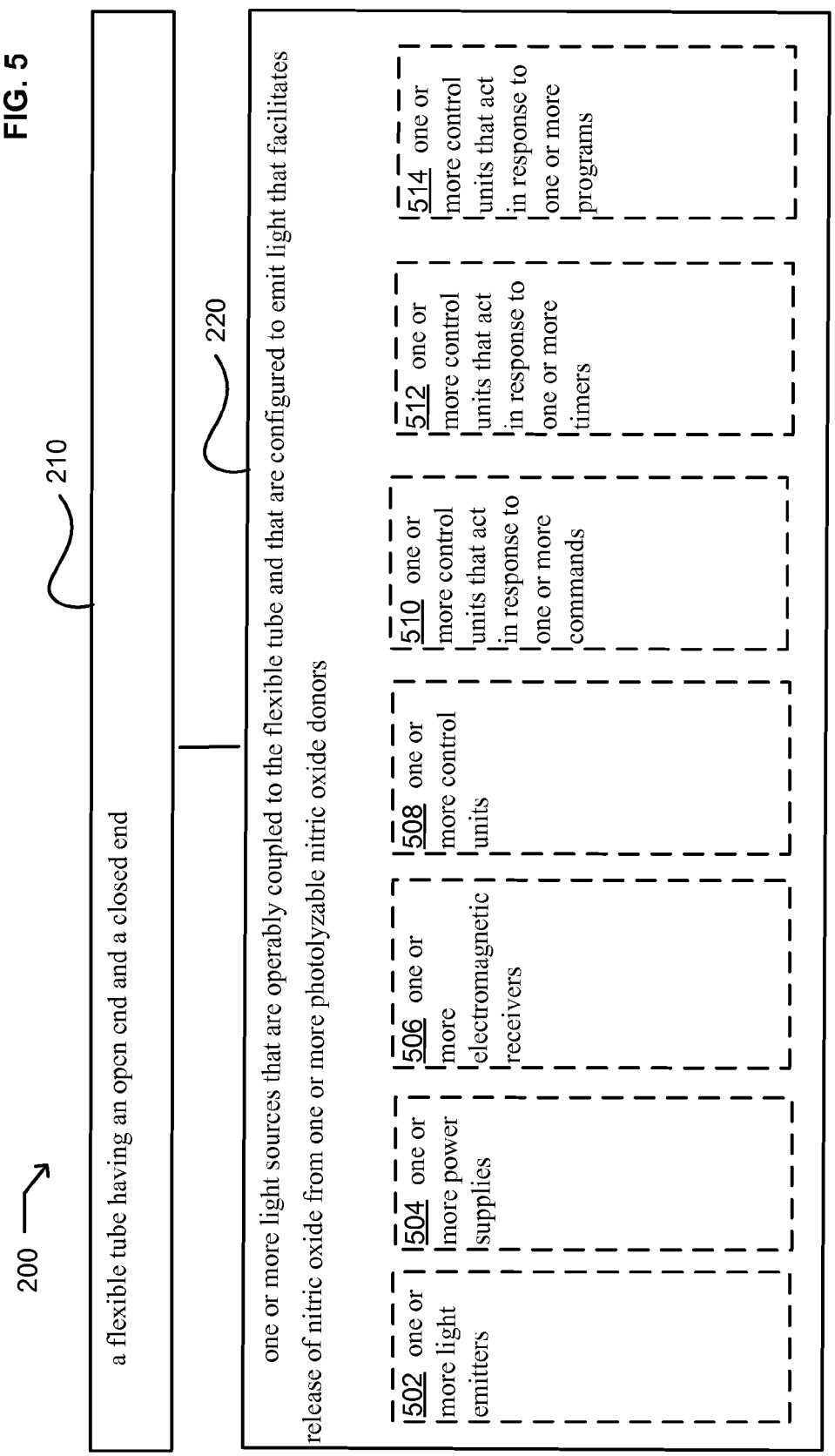
FIG. 5 illustrates alternate embodiments of module 220 of embodiment 200 of condom 102 within system 100.

FIG. 5 illustrates alternative embodiments of embodiment 200 of condom 102 within system 100 of FIG. 2. FIG. 5 illustrates example embodiments of module 220 of condom 102. Additional embodiments may include an embodiment 502, an embodiment 504, an embodiment 506, an embodiment 508, an embodiment 510, an embodiment 512, and/or an embodiment 514.

At embodiment 502, module 220 may include one or more light emitters. In some embodiments, a light source 106 may include one or more light emitters. Numerous types of light emitters may be associated with one or more light sources 106. Examples of such light emitters include, but are not limited to, light emitting diodes, filaments, arc lamps, fluorescent light emitters, phosphorescent light emitters, chemiluminescent emitters, and the like. In some embodiments, one or more light emitters may be coupled with one or more quantum dots. In some embodiments, one or more light emitters may be coupled with one or more rare-earth materials.

At embodiment 504, module 220 may include one or more power supplies. In some embodiments, a light source 106 may include one or more power supplies. Numerous types of power supplies may be associated with one or more light sources 106. Examples of such power supplies include, but are not limited to, batteries (e.g., thin film batteries), electromagnetic receivers 114, capacitors, and the like.

At embodiment 506, module 220 may include one or more electromagnetic receivers. In some embodiments, a light source 106 may include one or more electromagnetic receivers 114. In some embodiments, one or more electromagnetic receivers 114 may be used to receive electromagnetic energy 116 for use in providing power to one or more light emitters. Methods to construct electromagnetic receivers 114 have been described (e.g., U.S. Pat. No. 5,571,152).

At embodiment 508, module 220 may include one or more control units. In some embodiments, a light source 106 may include one or more control units. A light source 106 may include numerous types of control units. In some embodiments, one or more control units may be operably coupled with one or more light sources 106, one or more sensors 110, one or more electromagnetic receivers 114, or substantially any combination thereof. Control units may be configured in numerous ways. For example, in some embodiments, a control unit may be configured as an on/off switch. Accordingly, in some embodiments, a control unit may be configured to turn a light source 106 on and/or off. In some embodiments, a control unit may be configured to control the emission of light from one or more light sources 106. For example, in some embodiments, one or more control units may regulate the intensity of light emitted from one or more light sources 106, the duration of light emitted from one or more light sources 106, the frequency of light emitted from one or more light sources 106, wavelengths of light emitted from one or more light sources 106, or substantially any combination thereof. In some embodiments, one or more control units may be configured to receive one or more signals 120 from one or more sensors 110. Accordingly, in some embodiments, one or more control units may be configured to control one or more light sources 106 in response to one or more signals 120 received from one or more sensors 110. For example, in some embodiments, one or more sensors 110 may sense a low concentration of nitric oxide in one or more tissues and send one or more signals 120 to one or more control units. The one or more control units may then turn one or more light sources 106 on to facilitate release of nitric oxide from one or more photolyzable nitric oxide donors 108. Accordingly, in some embodiments, one or more sensors 110 may sense a high concentration of nitric oxide in one or more tissues and send one or more signals 120 to one or more control units. The one or more control units may then turn one or more light sources 106 off to end release of nitric oxide from one or more photolyzable nitric oxide donors 108. In some embodiments, one or more control units may be programmed to control one or more light sources 106. For example, in some embodiments, one or more control units may be programmed to turn one or more light sources 106 on for a predetermined amount of time and then turn off. Accordingly, in some embodiments, one or more control units may be preprogrammed. In some embodiments, one or more control units may be dynamically programmed. For example, in some embodiments, one or more management units 122 may receive one or more signals 120 from one or more sensors 110 and program one or more control units in response to the one or more signals 120 received from the one or more sensors 110. In some embodiments, one or more control units may include one or more receivers that are able to receive one or more signals 120, one or more information packets, or substantially any combination thereof. Control units may be configured in numerous ways. For example, in some embodiments, one or more control units may be operably coupled to one or more light sources 106 that include numerous light emitting diodes that emit light of different wavelengths. Accordingly, in some embodiments, one or more control units may control the wavelengths of light emitted by the one or more light sources 106 by controlling the operation of light emitting diodes that emit light of the selected wavelength. Accordingly, control units may be configured in numerous ways and utilize numerous types of mechanisms.

At embodiment 510, module 220 may include one or more control units that act in response to one or more commands. In some embodiments, a light source 106 may include one or more control units that act in response to one or more commands. For example, in some embodiments, one or more control units may receive one or more signals 120 that act as commands for the one or more control units. In some embodiments, one or more control units may receive one or more information packets that act as commands for the one or more control units.

At embodiment 512, module 220 may include one or more control units that act in response to one or more timers. In some embodiments, a light source 106 may include one or more control units that act in response to one or more timers. In some embodiments, one or more control units may be configured to include one or more timers to which the one or more control units are responsive. In some embodiments, one or more control units may be responsive to one or more timers that are remote from the one or more control units. For example, in some embodiments, one or more control units may be responsive to one or more timers that are associated with one or more management units 122 that send instructions to the one or more control units.

At embodiment 514, module 220 may include one or more control units that act in response to one or more programs. In some embodiments, a light source 106 may include one or more control units that act in response to one or more programs. For example, in some embodiments, one or more control units may be responsive to a programmed set of instructions. In some embodiments, the one or more control units may be directly programmed. For example, in some embodiments, one or more control units may include a programmable memory that can include instructions. In some embodiments, the one or more control units may receive instructions from a program that is associated with one or more management units 122.

Figure 6:
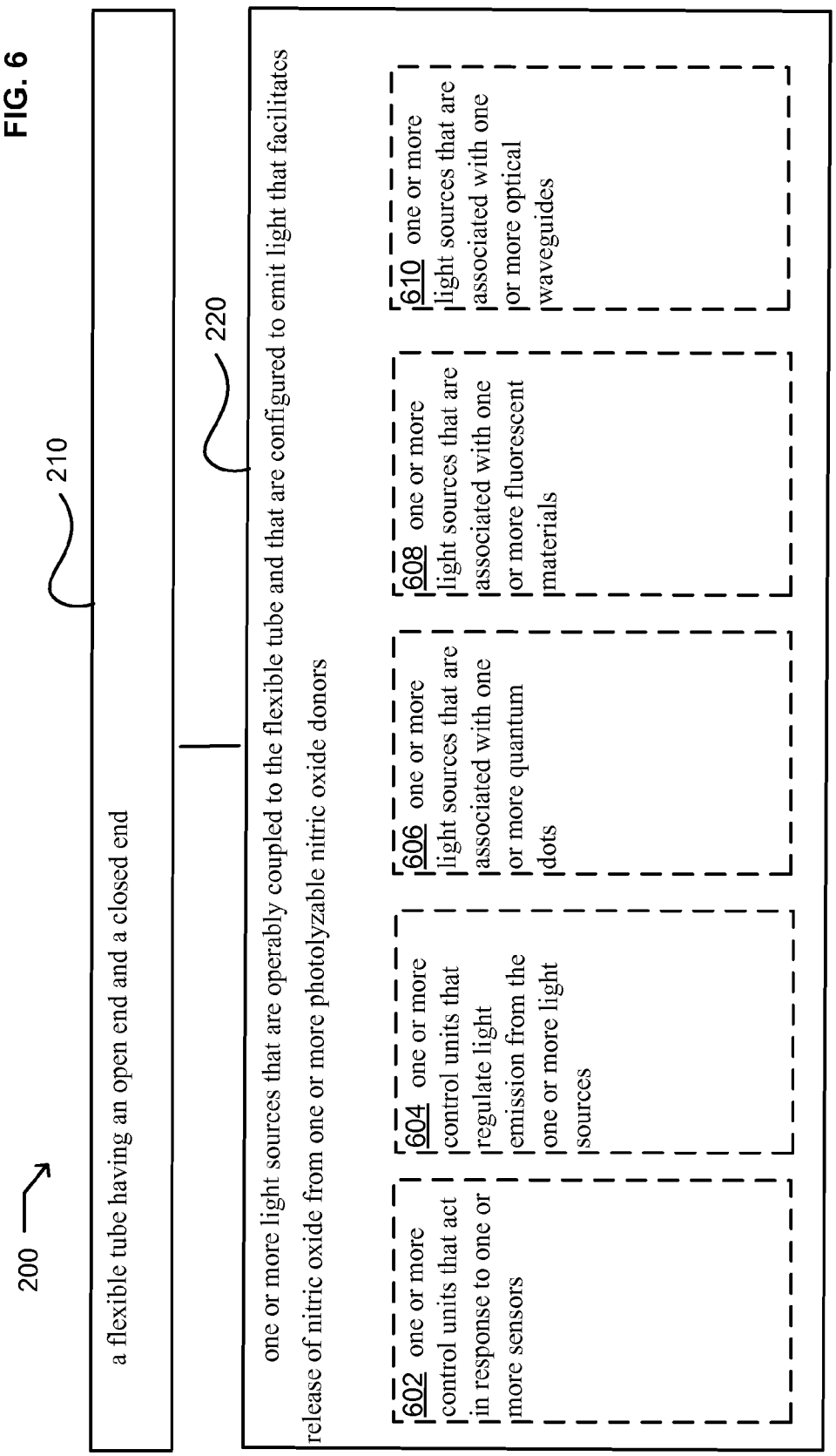
FIG. 6 illustrates alternate embodiments of module 220 of embodiment 200 of condom 102 within system 100.

FIG. 6 illustrates alternative embodiments of embodiment 200 of condom 102 within system 100 of FIG. 2. FIG. 6 illustrates example embodiments of module 220 of condom 102. Additional embodiments may include an embodiment 602, an embodiment 604, an embodiment 606, an embodiment 608, and/or an embodiment 610.

At embodiment 602, module 220 may include one or more control units that act in response to one or more sensors. In some embodiments, a light source 106 may include one or more control units that act in response to one or more sensors 110. In some embodiments, one or more control units may act in response to one or more sensors 110 that are coupled to a condom 102. For example, in some embodiments, one or more control units may act in response to one or more sensors 110 that are included within one or more collars associated with a condom 102. In some embodiments, one or more control units may act in response to one or more sensors 110 that are not directly coupled to the one or more control units. For example, in some embodiments, one or more control units may act in response to one or more sensors 110 that are implanted within an individual 126 and which are not directly coupled to the one or more control units. One or more control units may act in response to numerous types of sensors 110. Examples of such sensors 110 include, but are not limited to, sensors 110, strain sensors 110, penile rigidity sensors 110, nitric oxide synthase sensors 110, nitric oxide donor sensors 110, and the like. The one or more control units may be associated with one or more light sources 106. Accordingly, the one or more control units may regulate light emitted by one or more light sources 106 in response to one or more sensors 110.

At embodiment 604, module 220 may include one or more control units that regulate light emission from the one or more light sources. In some embodiments, a light source 106 may include one or more control units that regulate light emission from the one or more light sources 106. One or more control units may regulate numerous aspects of one or more light sources 106. Examples of such aspects include, but are not limited to, intensity of emitted light, duration of emitted light, pulse frequency of emitted light, wavelengths of emitted light, one or more times when light is emitted, one or more times when light is not emitted, and the like.

At embodiment 606, module 220 may include one or more light sources that are associated with one or more quantum dots. In some embodiments, a light source 106 may include one or more light sources 106 that are associated with one or more quantum dots (e.g., U.S. Pat. No. 7,235,361; herein incorporated by reference). For example, in some embodiments, one or more light sources 106 may be configured to emit one or more wavelengths of light that are absorbed by one or more quantum dots. In some embodiments, one or more quantum dots may be configured to absorb light and then emit one or more wavelengths of light that cause release of nitric oxide from one or more photolyzable nitric oxide donors 108. Accordingly, in some embodiments, emission from one or more first quantum dots may be tuned to facilitate release of nitric oxide from a first photolyzable nitric oxide donor 108 and emission from one or more second quantum dots may be tuned to facilitate release of nitric oxide from a second photolyzable nitric oxide donor 108.

At embodiment 608, module 220 may include one or more light sources that are associated with one or more fluorescent materials. In some embodiments, a light source 106 106 may include one or more light sources 106 that are associated with one or more fluorescent materials. Numerous fluorescent materials may be associated with one or more light sources 106. Examples of such materials include, but are not limited to, 1,4-diphenylbutadiyne; 9,10-diphenylanthracene; benzene; biphenyl; ethyl-p-dimethylaminobenzoate; naphthalene; P-terphenyl; ethyl-p-dimethylaminobenzoate; stilbene; tryptophan; tyrosine; 1,2-diphenylacetylene; 7-methoxycoumarin-4-acetic acid; anthracene; indo-1; POPOP; P-quaterphenyl; pyrene; and the like.

At embodiment 610, module 220 may include one or more light sources that are associated with one or more optical waveguides. In some embodiments, a light source 106 may be associated with one or more optical waveguides. Numerous types of optical waveguides may be associated with one or more light sources 106. For example, in some embodiments, a waveguide may be an optical fiber waveguide. In some embodiments, a waveguide may be a rectangular waveguide. In some embodiments, a waveguide may be a dielectric slab waveguide. In some embodiments, optical waveguides may include, but are not limited to, planar waveguides, strip waveguides, and/or fiber waveguides. In some embodiments, an optical waveguide may have a single-mode structure. In some embodiments, an optical waveguide may have a multi-mode structure. In some embodiments, an optical waveguide may exhibit a step refractive index distribution. In some embodiments, an optical waveguide may exhibit a gradient refractive index distribution. An optical waveguide may be constructed from numerous types of materials that include, but are not limited to, glass, polymers, semiconductors, and the like. Methods to construct optical waveguides have been described (e.g., U.S. Pat. No. 7,283,710).

Figure 7:
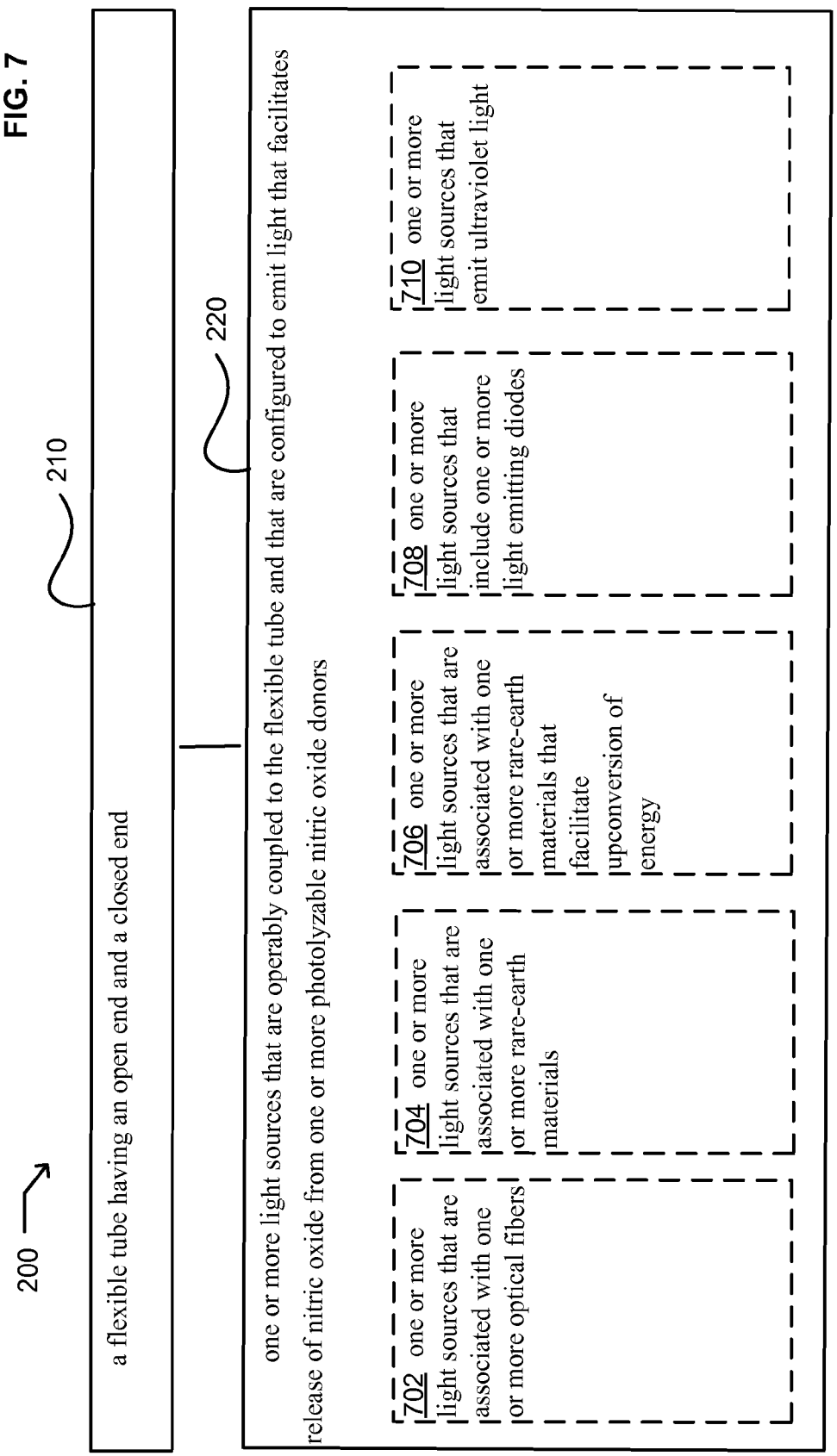
FIG. 7 illustrates alternate embodiments of module 220 of embodiment 200 of condom 102 within system 100.

FIG. 7 illustrates alternative embodiments of embodiment 200 of condom 102 within system 100 of FIG. 2. FIG. 7 illustrates example embodiments of module 220 of condom 102. Additional embodiments may include an embodiment 702, an embodiment 704, an embodiment 706, an embodiment 708, and/or an embodiment 710.

At embodiment 702, module 220 may include one or more light sources that are associated with one or more optical fibers. In some embodiments, a light source 106 may be associated with one or more optical fibers. One or more light sources 106 may be associated with numerous types of optical fibers. Methods to construct optical fibers have been described. Examples of optical fibers include, but are not limited to, optical fibers that include a single core and/or one or more cores. In some embodiments, an optical fiber may include silica glass. In some embodiments, an optical fiber may include a cladding. Optical fibers have been described (e.g., U.S. Pat. Nos. 7,295,741; 7,295,737).

In some embodiments, one or more photolyzable nitric oxide donors 108 may be directly associated with one or more optical fibers. For example, in some embodiments, one or more optical fibers may be directly coated with one or more photolyzable nitric oxide donors 108. In some embodiments, one or more optical fibers may be directly coated with one or more compositions that include one or more photolyzable nitric oxide donors 108. In some embodiments, one or more portions of one or more optical fibers may be directly coated with one or more photolyzable nitric oxide donors 108. In some embodiments, one or more portions of one or more optical fibers may be directly coated with one or more compositions that include one or more photolyzable nitric oxide donors 108. In some embodiments, one or more photolyzable nitric oxide donors 108 may be indirectly associated with one or more optical fibers. For example, in some embodiments, one or more optical fibers may be inserted into a structure that is coated with one or more photolyzable nitric oxide donors 108. In some embodiments, one or more optical fibers may be inserted into a structure that is coated with one or more compositions that include one or more photolyzable nitric oxide donors 108. In some embodiments, one or more optical fibers may be inserted into a structure that is partially coated with one or more photolyzable nitric oxide donors 108. In some embodiments, one or more optical fibers may be inserted into a structure that is partially coated with one or more compositions that include one or more photolyzable nitric oxide donors 108. For example, in some embodiments, one or more optical fibers may be inserted into one or more tubes that are coated with one or more photolyzable nitric oxide donors 108. In some embodiments, one or more optical fibers may be inserted into one or more tubes that are coated with one or more compositions that include one or more photolyzable nitric oxide donors 108.

At embodiment 704, module 220 may include one or more light sources that are associated with one or more rare-earth materials. In some embodiments, a light source 106 may include one or more light sources 106 that are associated with one or more rare-earth materials. In some embodiments, one or more rare-earth materials may include one or more rare-earth elements. The rare-earth elements are a collection of sixteen chemical elements in the periodic table, namely scandium, yttrium, and fourteen of the fifteen lanthanoids (excluding promethium). In some embodiments, one or more rare-earth materials may include one or more rare-earth elements that fluoresce.

At embodiment 706, module 220 may include one or more light sources that are associated with one or more rare-earth materials that facilitate upconversion of energy. In some embodiments, a light source 106 may include one or more light sources 106 that are associated with one or more rare-earth materials that facilitate upconversion of energy. In some embodiments, infrared light may be upconverted to visible light (e.g., Mendioroz et al., Optical Materials, 26:351-357 (2004). In some embodiments, infrared light may be upconverted to ultraviolet light (e.g., Mendioroz et al., Optical Materials, 26:351-357 (2004). In some embodiments, one or more light sources 106 may include one or more rare-earth materials (e.g., ytterbium-erbium, ytterbium-thulium, or the like) that facilitate upconversion of energy (e.g., U.S. Pat. No. 7,088,040; herein incorporated by reference). For example, in some embodiments, one or more light sources 106 may be associated with Nd3+ doped KPb2Cl5 crystals. In some embodiments, one or more light sources 106 may be associated with thiogallates doped with rare earths, such as CaGa2S4:Ce3+ and SrGa2S4:Ce3+. In some embodiments, one or more light sources 106 may be associated with aluminates that are doped with rare earths, such as YAlO3:Ce3+, YGaO3:Ce3+, Y(Al,Ga)O3:Ce3+, and orthosilicates M2SiO5:Ce3+ (M:Sc, Y, Sc) doped with rare earths, such as, for example, Y2SiO5:Ce3+. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

At embodiment 708, module 220 may include one or more light sources that include one or more light emitting diodes. In some embodiments, a light source 106 may include one or more light sources 106 that include one or more light emitting diodes. One or more light sources 106 may include one or more light emitting diodes that are configured to emit light of select wavelengths. For example, light emitting diodes may be configured to emit infrared light, visible light, near-ultraviolet light, or ultraviolet light. In some embodiments, a light source 106 may include a conventional light emitting diode that can include a variety of inorganic semiconductor materials. Examples of such materials and the emitting light include, but are not limited to, aluminium gallium arsenide (red and infrared), aluminium gallium phosphide (green), aluminium gallium indium phosphide (high-brightness orange-red, orange, yellow, and green), gallium arsenide phosphide (red, orange-red, orange, and yellow), gallium phosphide (red, yellow and green), gallium nitride (green, pure green, emerald green, blue, and white (if it has an AlGaN Quantum Barrier)), indium gallium nitride (near ultraviolet, bluish-green and blue), silicon carbide (blue), silicon (blue), sapphire (blue), zinc selenide (blue), diamond (ultraviolet), aluminium nitride (near to far ultraviolet), aluminium gallium nitride (near to far ultraviolet), aluminium gallium indium nitride (near to far ultraviolet).

At embodiment 710, module 220 may include one or more light sources that emit ultraviolet light. In some embodiments, a light source 106 may include one or more light sources 106 that emit ultraviolet light. In some embodiments, one or more light sources 106 may emit a broad spectrum of ultraviolet light. In some embodiments, one or more light sources 106 may emit a narrow spectrum of ultraviolet light. In some embodiments, one or more light sources 106 that emit one or more wavelengths of ultraviolet light that are specifically selected to release nitric oxide from one or more photolyzable nitric oxide donors 108. In some embodiments, one or more light sources 106 may emit ultraviolet light that does not include one or more wavelengths of light. In some embodiments, one or more light sources 106 may emit ultraviolet light that is selected to avoid and/or reduce damage to structures and/or tissues of an individual 126. For example, in some embodiments, one or more light sources 106 may emit ultraviolet light that does not include wavelengths of light that are absorbed by nucleic acids. In some embodiments, one or more light sources 106 may emit ultraviolet light that does not include wavelengths of light that are absorbed by polypeptides. In some embodiments, one or more light sources 106 may emit light that does not include one or more wavelengths of ultraviolet light within the following range: 250-320 nm. For example, in some embodiments, one or more light sources 106 may not emit 260 nm light. In some embodiments, one or more light sources 106 may not emit 280 nm light. In some embodiments, one or more light sources 106 may not emit 260 nm light or 280 nm light. Accordingly, numerous combinations of wavelengths of light may be excluded from emission by one or more light sources 106. In some embodiments, light may be emitted continuously. In some embodiments, light may be emitted as a flash. In some embodiments, light may be emitted alternately as continuous light and a flash. In some embodiments, light may be emitted as a pulse. In some embodiments, light may be emitted continuously, as a flash, as a pulse, or substantially any combination thereof.

Figure 8:
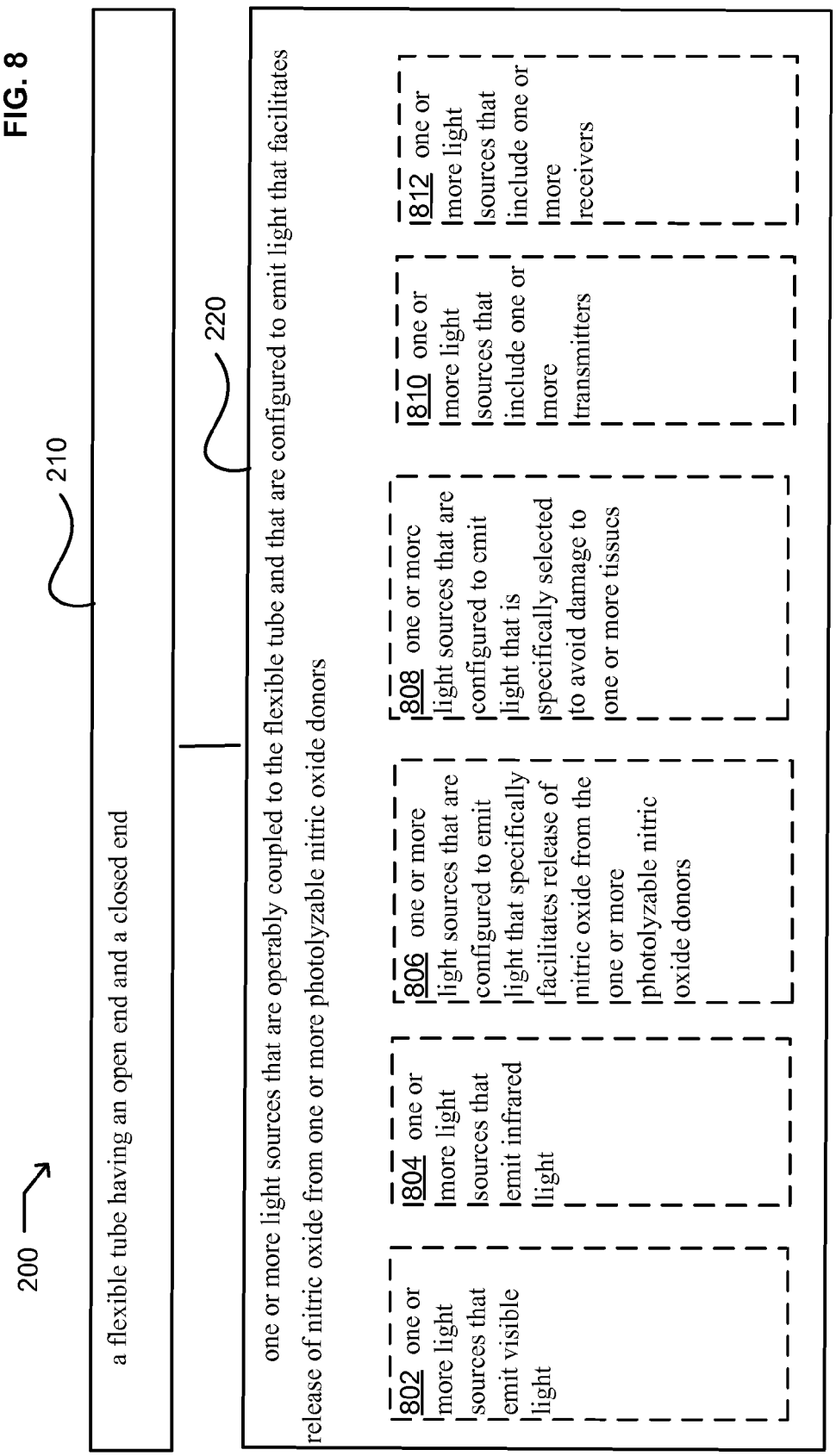
FIG. 8 illustrates alternate embodiments of module 220 of embodiment 200 of condom 102 within system 100.

FIG. 8 illustrates alternative embodiments of embodiment 200 of condom 102 within system 100 of FIG. 2. FIG. 8 illustrates example embodiments of module 220 of condom 102. Additional embodiments may include an embodiment 802, an embodiment 804, an embodiment 806, an embodiment 808, an embodiment 810, and/or an embodiment 812.

At embodiment 802, module 220 may include one or more light sources that emit visible light. In some embodiments, a light source 106 may include one or more light sources 106 that may emit visible light. In some embodiments, one or more light sources 106 may emit a broad spectrum of visible light. In some embodiments, one or more light sources 106 may emit a narrow spectrum of visible light. In some embodiments, one or more light sources 106 may emit one or more wavelengths of visible light that are specifically selected to release nitric oxide from one or more photolyzable nitric oxide donors 108. In some embodiments, one or more light sources 106 may emit visible light that does not include one or more wavelengths of light. In some embodiments, one or more light sources 106 may emit visible light that is selected to avoid and/or reduce damage to structures and/or tissues of an individual 126. Accordingly, numerous combinations of wavelengths of light may be excluded from emission by one or more light sources 106. In some embodiments, light may be emitted continuously. In some embodiments, light may be emitted as a flash. In some embodiments, light may be emitted alternately as continuous light and a flash. In some embodiments, light may be emitted as a pulse. In some embodiments, light may be emitted continuously, as a flash, as a pulse, or substantially any combination thereof. In some embodiments, the visible light may be upconverted.

At embodiment 804, module 220 may include one or more light sources that emit infrared light. In some embodiments, a light source 106 may include one or more light sources 106 that emit infrared light. In some embodiments, one or more light sources 106 may emit a broad spectrum of infrared light. In some embodiments, one or more light sources 106 may emit a narrow spectrum of infrared light. In some embodiments, one or more light sources 106 may emit one or more wavelengths of infrared light that are specifically selected to release nitric oxide from one or more photolyzable nitric oxide donors 108. In some embodiments, one or more light sources 106 may emit infrared light that does not include one or more wavelengths of light. In some embodiments, one or more light sources 106 may emit infrared light that is selected to avoid and/or reduce damage to structures and/or tissues of an individual 126. Accordingly, numerous combinations of wavelengths of light may be excluded from emission by one or more light sources 106. In some embodiments, light may be emitted continuously. In some embodiments, light may be emitted as a flash. In some embodiments, light may be emitted alternately as continuous light and a flash. In some embodiments, light may be emitted as a pulse. In some embodiments, light may be emitted continuously, as a flash, as a pulse, or substantially any combination thereof. In some embodiments, the infrared light may be upconverted.

At embodiment 806, module 220 may include one or more light sources that are configured to emit light that specifically facilitates release of nitric oxide from the one or more photolyzable nitric oxide donors. In some embodiments, a light source 106 may include one or more light sources 106 that are configured to emit light that specifically facilitates release of nitric oxide from the one or more nitric oxide donors. For example, in some embodiments, one or more light sources 106 may be configured to emit light that includes one or more wavelengths of light that correspond to the absorption maximum for one or more nitric oxide donors. Examples of nitric oxide donors and their associated $\lambda_{max}$ (nm) are provided in Table I below. Accordingly, one or more light sources 106 may be configured to emit numerous wavelengths of light.

TABLE I

Example Nitric Oxide Donors

| Compound Name | $\lambda_{max}$ (nm) |
|---|---|
| $O^2$-(Acetoxymethyl) 1-(N,N-Diethylamino)diazen-1-ium-1,2-diolate | 230 |
| $O^2$-(Acetoxymethyl) 1-(Pyrrolidin-1-yl)diazen-1-ium-1,2-diolate | 256 |
| Sodium 1-(N-Benzyl-N-methylamino)diazen-1-ium-1,2-diolate | 252 |
| $O^2$-[(2,3,4,6-Tetra-O-acetyl)-β-D-glucosyl] 1-[4-(2,3-Dihydroxypropyl)piperazin-1 | 232 |
| Sodium 1-[4-(2,3-Dihydroxypropyl)piperazin-1-yl-]diazen-1-ium-1,2-diolate | 248.5 |
| $O^2$-Methyl 1-[(4-Carboxamido)piperidin-1-yl]diazen-1-ium-1,2-diolate | 241 |
| $O^2$-(2-Chloropyrimidin-4-yl) 1-(Pyrrolidin-1-yl)diazen-1-ium-1,2-diolate | 274 |
| $O^2$-(2,4-Dinitrophenyl) 1-[4-(N,N-Diethylcarboxamido)piperazin-1-yl]diazen-1-ium-1,2-diolate | 300 |
| $O^2$-(2,4-Dinitrophenyl) 1-(4-Nicotinylpiperazin-1-yl)diazen-1-ium-1,2-diolate | 300 |
| $O^2$-(2,4-Dinitrophenyl) 1-{4-[2-(4-{2-Methylpropyl}phenyl)propionyl]piperazin-1-yl}diazen-1-ium-1,2-diolate | 300 |
| Sodium 1-(4-Benzyloxycarbonylpiperazin-1-yl)diazen-1-ium-1,2-diolate | 252 |
| $O^2$-(2,4-Dinitrophenyl) 1-[4-(tert-Butoxycarbonyl)piperazin-1-yl]diazen-1-ium-1,2-diolate | 299 |
| $O^2$-(2,4-Dinitrophenyl) 1-(4-Acetylpiperazin-1-yl)diazen-1-ium-1,2-diolate | 394 |
| $O^2$-(2,4-Dinitrophenyl) 1-[4-(Succinimidoxycarbonyl)piperazin-1-yl]diazen-1-ium-1,2-diolate | 300 |
| $O^2$-(2,4-Dinitrophenyl) 1-(Piperazin-1-yl)diazen-1-ium-1,2-diolate, Hydrochloride Salt | 297 |

TABLE I-continued

Example Nitric Oxide Donors

| Compound Name | $\lambda_{max}$ (nm) |
|---|---|
| $O^2$-(2,3,4,6-Tetra-O-acetyl-D-glucopyranosyl) 1-(N,N-Diethylamino)diazen-1-ium-1,2-diolate | 228 |
| $O^2$-(-D-Glucopyranosyl) 1-(N,N-Diethylamino)diazen-1-ium-1,2-diolate | 228 |
| Sodium (Z)-1-(N,N-Diethylamino)diazen-1-ium-1,2-diolate | 250 |
| 1-[N-(2-Aminoethyl)-N-(2-ammonioethyl)amino]diazen-1-ium-1,2-diolate | 252 |
| Sodium 1-(N,N-Dimethylamino)diazen-1-ium-1,2-diolate | 250 |
| $O^2$-(2,4-Dinitrophenyl) 1-(N,N-Diethylamino)diazen-1-ium-1,2-diolate | 302 |
| 1-[N-(3-Aminopropyl)-N-(3-ammoniopropyl]diazen-1-ium-1,2-diolate | 252 |
| 1-[N-(3-Aminopropyl)-N-(3-ammoniopropyl]diazen-1-ium-1,2-diolate | 252 |
| Bis-diazeniumdiolated benzyl imidate dehydrate | 264 |
| p-Bisdiazeniumdiolated benzene | 316 |
| Methane Trisdiazeniumdiolate trihydrate | 316 |
| $O^2$-(β-D-Glucopyranosyl) 1-(Isopropylamino)diazen-1-ium-1,2-diolate | 278 |
| Sodium 1-[4-(5-Dimethylamino-1-naphthalenesulfonyl)piperazin-1-yl]diazen-1-ium-1,2-diolate | 344 |
| 1-(2-Methyl-1-propenyl)piperidine diazeniumdiolate | 246 |
| 1-(2-Methyl-1-propenyl)pyrrolidine diazeniumdiolate | 246 |
| $O^2$-Vinyl 1-(Pyrrolidin-1-yl)diazen-1-ium-1,2-diolate | 268 |
| 1-{N-[3-Aminopropyl]-N-[4-(3-aminopropylammoniobutyl)]}diazen-1-ium-1,2-diolate | 252 |
| Disodium 1-[(2-Carboxylato)pyrrolidin-1-yl]diazen-1-ium-1,2-diolate | 252 |
| 1-[N-(3-Ammoniopropyl)-N-(n-propyl)amino]diazen-1-ium-1,2-diolate | 250 |
| (Z)-1-{N-Methyl-N-[6-(N-methylammoniohexyl)amino]}diazen-1-ium-1,2-diolate | 250 |
| $O^2$-(2,4-Dinitrophenyl) 1-[(4-Ethoxycarbonyl)piperazin-1-yl]diazen-1-ium-1,2-diolate | 300 |

At embodiment 808, module 220 may include one or more light sources that are configured to emit light that is specifically selected to avoid damage to one or more tissues. In some embodiments, a light source 106 may include one or more light sources 106 that are configured to emit light that is specifically selected to avoid damage to one or more tissues. In some embodiments, one or more light sources 106 may emit light that is selected to avoid and/or reduce damage to one or more structures and/or one or more tissues of an individual 126. For example, in some embodiments, one or more light sources 106 may emit light that does not include wavelengths of light that are absorbed by nucleic acids. In some embodiments, one or more light sources 106 may emit light that does not include wavelengths of light that are absorbed by polypeptides. In some embodiments, one or more light sources 106 may emit light that does not include one or more wavelengths of light within the following range: 250-320 nm. For example, in some embodiments, one or more light sources 106 may not emit 260 nm light. In some embodiments, one or more light sources 106 may not emit 280 nm light. In some embodiments, one or more light sources 106 may not emit 260 nm light or 280 nm light. Accordingly, numerous combinations of wavelengths of light may be excluded from emission by one or more light sources 106. In some embodiments, light may be emitted continuously. In some embodiments, light may be emitted as a flash. In some embodiments, light may be emitted alternately as continuous light and a flash. In some embodiments, light may be emitted as a pulse.

At embodiment 810, module 220 may include one or more light sources that include one or more transmitters. In some embodiments, a light source 106 may include one or more light sources 106 that include one or more transmitters. Accordingly, in some embodiments, a light source 106 may include a transmitter that is configured to transmit one or more signals 120. For example, in some embodiments, one or more transmitters may transmit one or more optical signals 120, radio signals 120, wireless signals 120, hardwired signals 120, infrared signals 120, ultrasonic signals 120, acoustic signals 120, and the like. In some embodiments, one or more light sources 106 may transmit one or more signals 120 that include information associated with operation of the one or more light sources 106. Examples of such information include, but are not limited to, wavelengths of emitted light, times of light emission, duration of light emission, intensity of emitted light, and the like.

At embodiment 812, module 220 may include one or more light sources that include one or more receivers. In some embodiments, a light source 106 may include one or more light sources 106 that include one or more receivers. Accordingly, in some embodiments, a light source 106 may include a receiver that is configured to receive one or more signals 120. For example, in some embodiments, one or more receivers may receive one or more optical signals 120, radio signals 120, wireless signals 120, hardwired signals 120, infrared signals 120, ultrasonic signals 120, acoustic signals 120, and the like. In some embodiments, one or more light sources 106 may receive one or more signals 120 that include information associated with operation of the one or more light sources 106. Examples of such information include, but are not limited to, wavelengths of light to be emitted, times of light emission, duration of light emission, intensity of emitted light, and the like. In some embodiments, one or more light sources 106 may receive one or more signals 120 from one or more sensors 110. Accordingly, in some embodiments, one or more light sources 106 may be configured to be responsive to one or more signals 120 received from one or more sensors 110.

Figure 9:
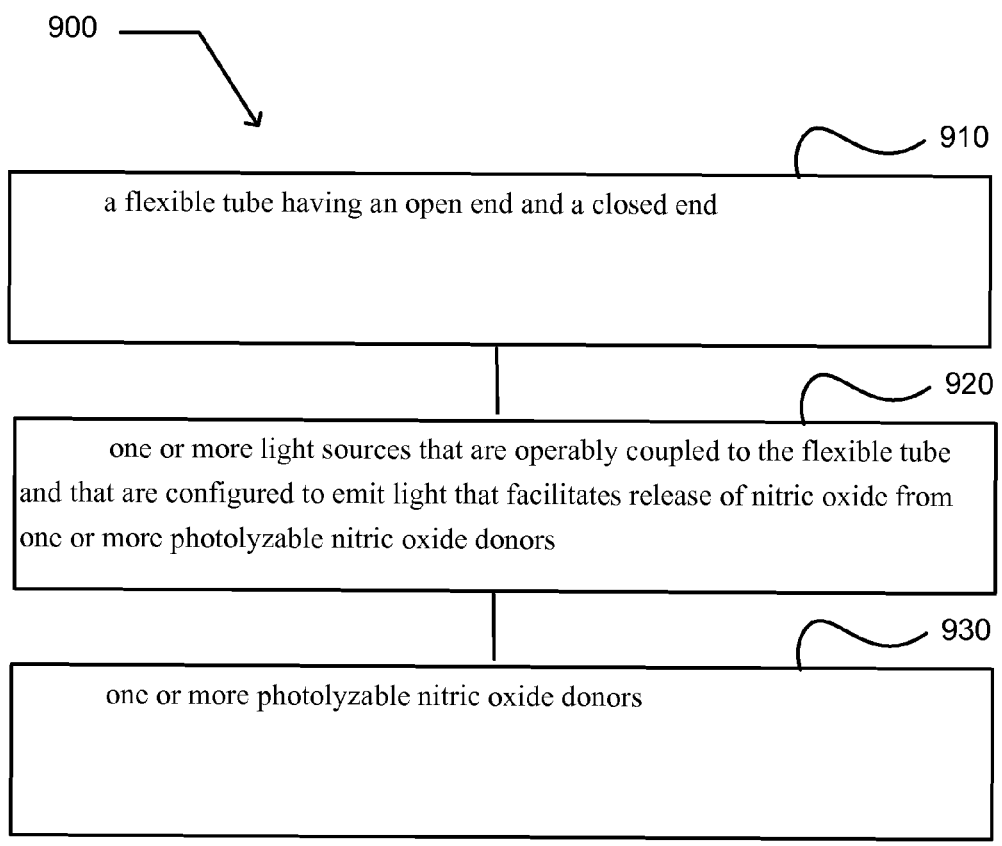
FIG. 9 illustrates embodiment 900 of condom 102 within system 100.

FIG. 9 illustrates embodiment 200 of condom 102 within system 100. In FIG. 9, discussion and explanation may be provided with respect to the above-described example of FIG. 1, and/or with respect to other examples and contexts. In some embodiments, modules 210 and 220 as described with respect to embodiment 200 of condom 102 of FIG. 2 may correspond to modules 910 and 920 as described with respect to embodiment 900 of condom 102 within system 100. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 900 may include module 910 that includes a flexible tube having an open end and a closed end. In some embodiments, a condom 102 may include a flexible tube 104 having an open end and a closed end. In some embodiments, a flexible tube 104 may include one layer of elastomeric material. In some embodiments, a flexible tube 104 may include one or more layers of elastomeric material. For example, in some embodiments, a flexible tube 104 may be constructed of a single layer of latex rubber. In some embodiments, a flexible tube 104 may be constructed of a single layer of polyethylene. In some embodiments, a flexible tube 104 may be constructed of two or more laminated layers. For example, in some embodiments, a flexible tube 104 may include an inner layer that is constructed from polyethylene and an outer layer that is made from latex and laminated onto the inner layer. In some embodiments, a flexible tube 104 may include an inner layer that is a nitric oxide permeable layer 112 and an outer layer that is a nitric oxide impermeable layer. In some embodiments, a flexible tube 104 may include an inner layer that is a nitric oxide permeable layer 112, an outer layer that is a nitric oxide impermeable layer, and one or more photolyzable nitric oxide donors 108 positioned between the inner layer and the outer layer. In some embodiments, a flexible tube 104 may include one or more spermicidal agents. In some embodiments, one or more spermicidal agents may be associated with one or more portions of an interior surface of a flexible tube 104. In some embodiments, one or more spermicidal agents may be associated with one or more portions of an exterior surface of a flexible tube 104. In some embodiments, one or more spermicidal agents may be associated with one or more portions of an interior surface and one or more portions of an external surface of a flexible tube 104. In some embodiments, a flexible tube 104 may include one or more antimicrobial agents. In some embodiments, one or more antimicrobial agents may be associated with one or more portions of an interior surface of a flexible tube 104. In some embodiments, one or more antimicrobial agents may be associated with one or more portions of an exterior surface of a flexible tube 104. In some embodiments, one or more antimicrobial agents may be associated with one or more portions of an interior surface and one or more portions of an external surface of a flexible tube 104. In some embodiments, a flexible tube 104 may include one or more antiviral agents. In some embodiments, one or more antiviral agents may be associated with one or more portions of an interior surface of a flexible tube 104. In some embodiments, one or more antiviral agents may be associated with one or more portions of an exterior surface of a flexible tube 104. In some embodiments, one or more antiviral agents may be associated with one or more portions of an interior surface and one or more portions of an external surface of a flexible tube 104.

A flexible tube 104 may be constructed through use of numerous processes. For example, in some embodiments, a flexible tube 104 may be constructed through a dipping process where a former is coated with one or more elastomeric materials. In some embodiments, a flexible tube 104 may be constructed through a spraying process where a former is spray coated with one or more elastomeric materials. In some embodiments, a flexible tube 104 may be constructed through a molding process where one or more elastomeric materials are introduced into a mold and cast into a flexible tube 104. Accordingly, numerous processes may be used to construct flexible tubes 104. In some embodiments, one or more light sources 106 may be applied to a form and then the form may be coated with one or more elastomeric materials to form a flexible tube 104 that is associated with one or more light sources 106. In some embodiments, one or more light sources 106 may be associated with a preformed flexible tube 104. Methods that may be used to construct a flexible tube 104 are known and have been described (e.g., U.S. Pat. Nos. 7,235,505; 6,983,751; 6,651,667; 6,308,708; 6,000,398; and 4,919,149).

The embodiment 900 may include module 920 that includes one or more light sources that are operably coupled to the flexible tube and that are configured to emit light that facilitates release of nitric oxide from one or more photolyzable nitric oxide donors. In some embodiments, a condom 102 may include one or more light sources 106 that are operably coupled to a flexible tube 104 and that are configured to emit light that facilitates release of nitric oxide from one or more photolyzable nitric oxide donors 108. A light source 106 may be configured in numerous ways. For example, in some embodiments, a light source 106 may include a chemiluminescent light source 106. In some embodiments, a light source 106 may include a phosphorescent light source 106. In some embodiments, a light source 106 may include a light emitter that is coupled to a power supply. For example, in some embodiments, a light source 106 may include one or more light emitting diodes that are coupled to one or more power supplies. Examples of power supplies include, but are not limited to, capacitors, batteries, electromagnetic receivers 114, and the like. In some embodiments, one or more light sources 106 may be configured to emit light that specifically facilitates release of nitric oxide from one or more photolyzable nitric oxide donors 108. For example, in some embodiments, one or more light sources 106 may be configured to emit one or more wavelengths of light that facilitate photodecomposition of one or more photolyzable nitric oxide donors 108. In some embodiments, one or more light sources 106 may be configured such that they do not emit one or more wavelengths of light that do not facilitate photodecomposition of one or more photolyzable nitric oxide donors 108. Accordingly, in some embodiments, one or more light sources 106 may be configured to emit light that is matched to one or more photolyzable nitric oxide donors 108 and causes photodecomposition of the one or more photolyzable nitric oxide donors 108. In some embodiments, one or more light sources 106 may be configured such that they do not emit light that cross-links biological structures (e.g., proteins) or that causes the formation of DNA adducts. Accordingly, in some embodiments, one or more light sources 106 may be configured to emit light that photolyzes one or more photolyzable nitric oxide donors 108 with reduced damage to surrounding tissue. For example, in some embodiments, one or more light sources 106 may be configured to emit visible light ($\lambda$=550 nm) to facilitate homolytic decomposition of S-nitrosoglutathione to generate nitric oxide (e.g., Singh et al., FEBS Letters, 360:47-51 (1995)). In some embodiments, ultraviolet light may be used to facilitate release of nitric oxide from one or more photolyzable nitric oxide donors 108. For example, in some embodiments, one or more light sources 106 may be configured to emit ultraviolet light ($\lambda$=355 nm) to release nitric oxide from S-nitrosothiols (e.g., Rotta et al., Braz. J. Med. Biol. Res., 36:587-594 (2003)). In some embodiments, one or more light sources 106 may be configured to emit light over a broad range of wavelengths that will facilitate release of nitric oxide from one or more photolyzable nitric oxide donors 108. For example, in some embodiments, $O^2$-benzyl substituted diazeniumdiolates, $O^2$-napthylmethyl substituted diazeniumdiolates, and/or $O^2$-napththylallyl substituted diazeniumdiolates may be photolyzed by light over a broad range of wavelengths ($\lambda$=254 nm to $\lambda$=700 nm) (e.g., U.S. Pat. No. 7,122,529).

The embodiment 900 may include module 930 that includes one or more photolyzable nitric oxide donors. In some embodiments, a condom 102 may include one or more photolyzable nitric oxide donors 108 that release nitric oxide upon photolysis. Examples of such photolyzable nitric oxide donors 108 include, but are not limited to, diazeniumdiolates (e.g., U.S. Pat. Nos. 7,105,502; 7,122,529; 6,673,338; herein incorporated by reference), trans-[RuCl([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550: 819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference).

Figure 10:
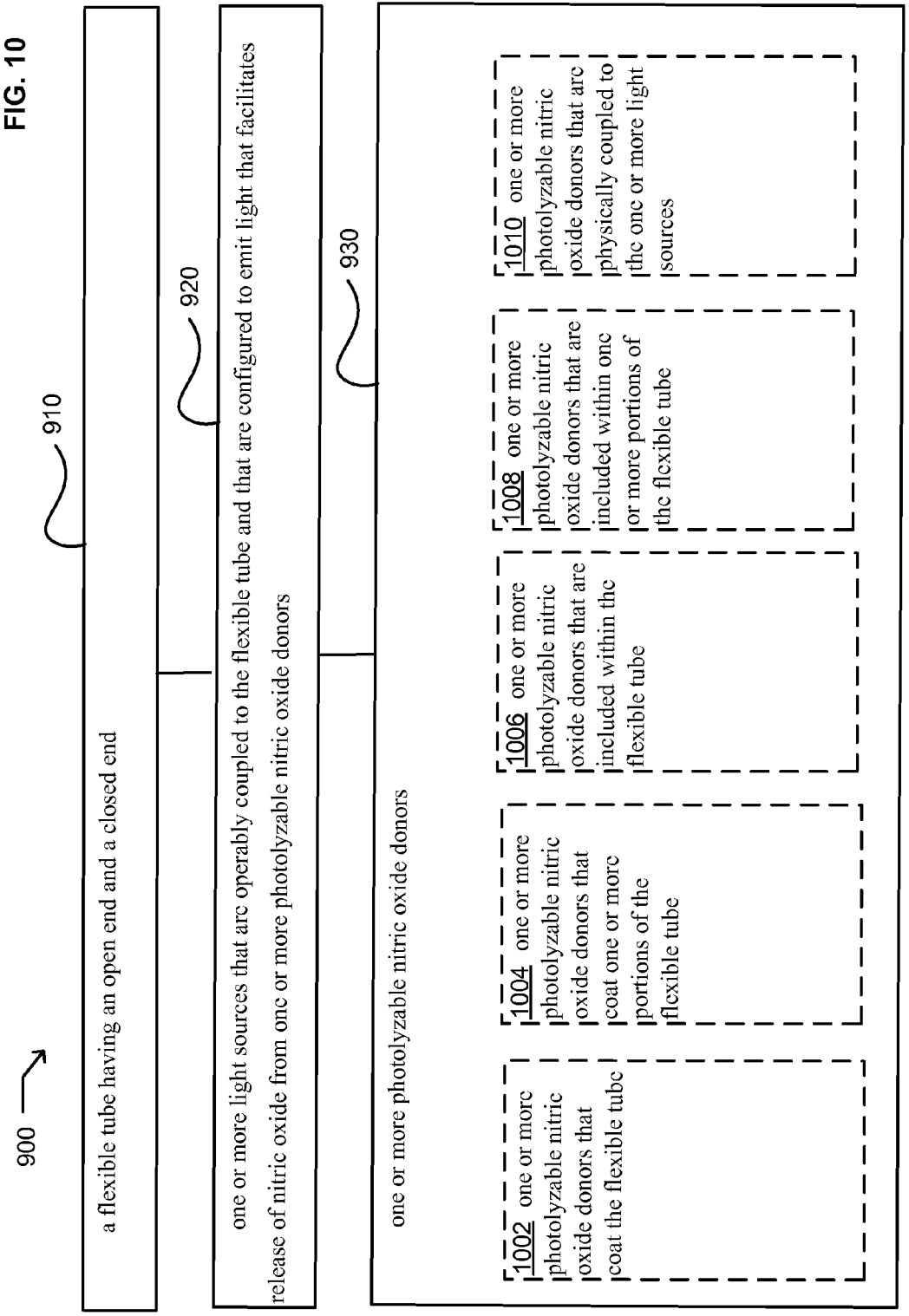
FIG. 10 illustrates alternate embodiments of module 930 of embodiment 900 of condom 102 within system 100.

FIG. 10 illustrates alternative embodiments of embodiment 900 of condom 102 within system 100 of FIG. 9. FIG. 10 illustrates example embodiments of module 930 of condom 102. Additional embodiments may include an embodiment 1002, an embodiment 1004, an embodiment 1006, an embodiment 1008, and/or an embodiment 1010.

At embodiment 1002, module 930 may include one or more photolyzable nitric oxide donors that coat the flexible tube. In some embodiments, one or more photolyzable nitric oxide donors 108 may include one or more photolyzable nitric oxide donors 108 that coat a flexible tube 104. In some embodiments, one or more photolyzable nitric oxide donors 108 may coat the entire interior of a flexible tube 104. In some embodiments, one or more photolyzable nitric oxide donors 108 may coat one or more portions of the inside of a flexible tube 104. Accordingly, in some embodiments, application of a condom 102 to an individual 126 will administer one or more photolyzable nitric oxide donors 108 to the surface of the individual's 126 penis. In some embodiments, a flexible tube 104 may be coated with one or more photolyzable nitric oxide donors 108 that are formulated to penetrate skin. For example, in some embodiments, one or more photolyzable nitric oxide donors 108 may be included within liposomes that can penetrate the skin of the penis.

At embodiment 1004, module 930 may include one or more photolyzable nitric oxide donors that coat one or more portions of the flexible tube. In some embodiments, one or more photolyzable nitric oxide donors 108 may include one or more photolyzable nitric oxide donors 108 that coat one or more portions of a flexible tube 104. In some embodiments, one or more photolyzable nitric oxide donors 108 may coat one or more portions of the inside of a flexible tube 104. Accordingly, in some embodiments, application of a condom 102 to an individual 126 will administer one or more photolyzable nitric oxide donors 108 to the surface of the individual's 126 penis. In some embodiments, a flexible tube 104 may be coated with one or more photolyzable nitric oxide donors 108 that are formulated to penetrate skin. For example, in some embodiments, one or more photolyzable nitric oxide donors 108 may be included within liposomes that can penetrate the skin of the penis.

At embodiment 1006, module 930 may include one or more photolyzable nitric oxide donors that are included within the flexible tube. In some embodiments, one or more photolyzable nitric oxide donors 108 may include one or more photolyzable nitric oxide donors 108 that are included within the flexible tube 104. For example, in some embodiments, a flexible tube 104 may include a porous layer that is impregnated with one or more photolyzable nitric oxide donors 108. In some embodiments, a flexible tube 104 may include a multilayered laminate construction which may include one or more photolyzable nitric oxide donors 108 between the layers. In some embodiments, a flexible tube 104 may include one or more photolyzable nitric oxide donors 108 that are chemically coupled to the flexible tube 104.

At embodiment 1008, module 930 may include one or more photolyzable nitric oxide donors that are included within one or more portions of the flexible tube. In some embodiments, one or more photolyzable nitric oxide donors 108 may include one or more photolyzable nitric oxide donors 108 that are included within one or more portions of the flexible tube 104. For example, in some embodiments, a flexible tube 104 may include a porous layer that is impregnated within one or more portions with one or more photolyzable nitric oxide donors 108. In some embodiments, a flexible tube 104 may include a multilayered laminate construction which may include one or more photolyzable nitric oxide donors 108 between one or more portions of the layers. In some embodiments, a flexible tube 104 may include one or more photolyzable nitric oxide donors 108 that are chemically coupled to one or more portions of the flexible tube 104.

At embodiment 1010, module 930 may include one or more photolyzable nitric oxide donors that are physically coupled to the one or more light sources. In some embodiments, one or more photolyzable nitric oxide donors 108 may include one or more photolyzable nitric oxide donors 108 that are physically coupled to the one or more light sources 106. In some embodiments, the one or more light sources 106 may be directly coupled to one or more photolyzable nitric oxide donors 108. For example, in some embodiments, the one or more photolyzable nitric oxide donors 108 may be chemically coupled to a surface of the light source 106 (e.g., chemically coupled to a polymer coating on the light source 106). In some embodiments, one or more photolyzable nitric oxide donors 108 may be indirectly coupled to one or more light sources 106. For example, in some embodiments, one or more photolyzable nitric oxide donors 108 may be coupled to a material that is used to coat the one or more light sources 106.

Figure 11:
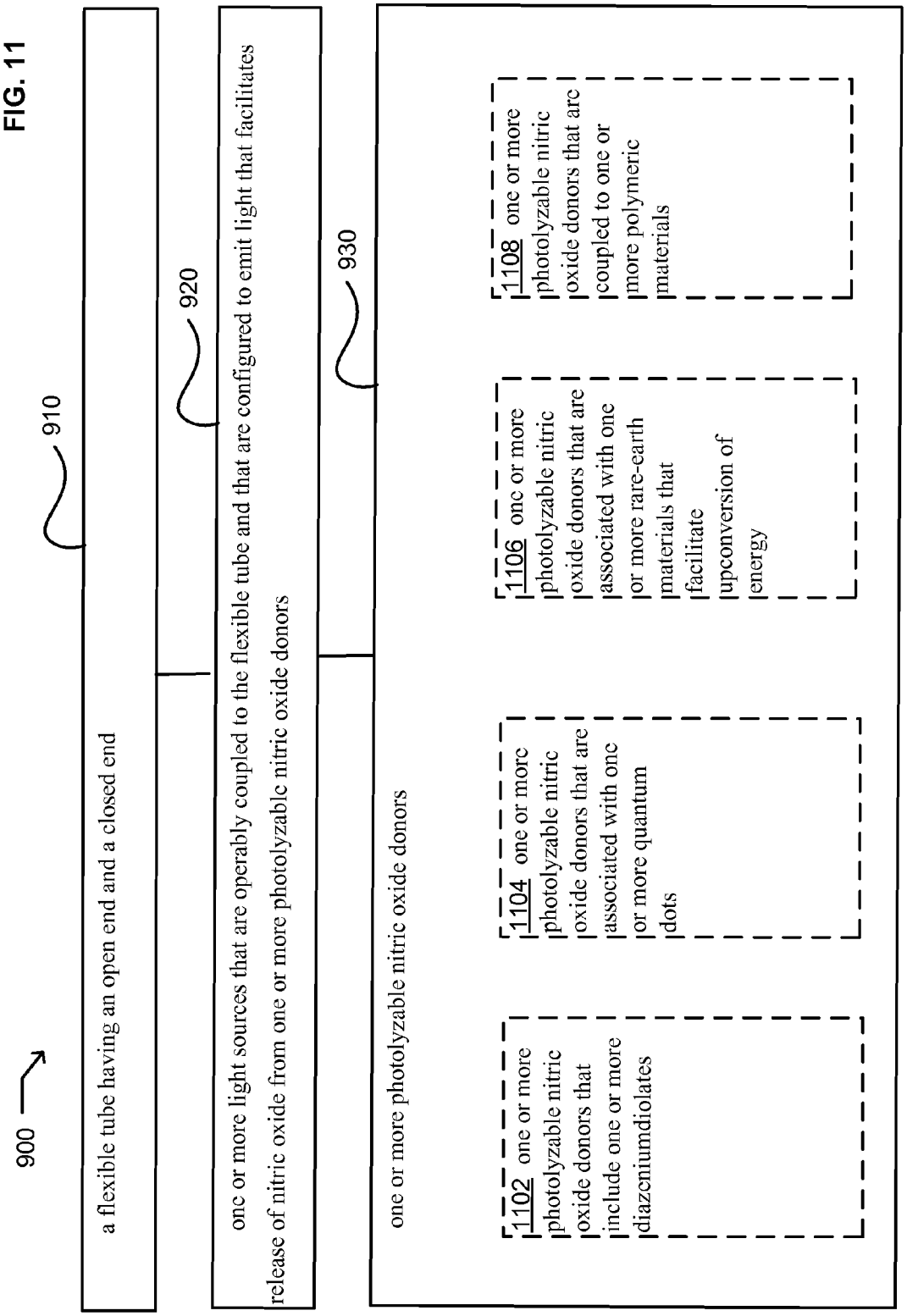
FIG. 11 illustrates alternate embodiments of module 930 of embodiment 900 of condom 102 within system 100.

FIG. 11 illustrates alternative embodiments of embodiment 900 of condom 102 within system 100 of FIG. 9. FIG. 11 illustrates example embodiments of module 930 of condom 102. Additional embodiments may include an embodiment 1102, an embodiment 1104, an embodiment 1106, and/or an embodiment 1108.

At embodiment 1102, module 930 may include one or more photolyzable nitric oxide donors that include one or more diazeniumdiolates. In some embodiments, one or more photolyzable nitric oxide donors 108 may include one or more photolyzable nitric oxide donors 108 that include one or more diazeniumdiolates. Many photolyzable nitric oxide donors 108 that are diazeniumdiolates are known and have been described (e.g., U.S. Pat. No. 7,122,529). Examples of such diazeniumdiolates include, but are not limited to, $O^2$-benzyl,$O^2$-naphthylmethyl substituted diazeniumdiolates and $O^2$-naphthylallyl substituted diazeniumdiolates.

At embodiment 1104, module 930 may include one or more photolyzable nitric oxide donors that are associated with one or more quantum dots. In some embodiments, one or more photolyzable nitric oxide donors 108 may include one or more photolyzable nitric oxide donors 108 that are associated with one or more quantum dots. In some embodiments, one or more quantum dots may be tuned to emit light that facilitates photolysis of one or more nitric oxide donors. In some embodiments, a quantum dot may be tuned to emit light that specifically facilitates photolysis of one or more nitric oxide donors. For example, in some embodiments, one or more quantum dots may emit select wavelengths of light that correspond to wavelengths of light that cause photolysis of one or more nitric oxide donors. In some embodiments, one or more quantum dots may be selected that absorb light emitted by one or more light sources 106 and emit light that facilitates photolysis of one or more nitric oxide donors.

At embodiment 1106, module 930 may include one or more photolyzable nitric oxide donors that are associated with one or more rare-earth materials that facilitate upconversion of energy. In some embodiments, one or more photolyzable nitric oxide donors 108 may include one or more photolyzable nitric oxide donors 108 that are associated with one or more rare-earth materials that facilitate upconversion of energy. In some embodiments, infrared light may be upconverted to visible light (e.g., Mendioroz et al., Optical Materials, 26:351-357 (2004). In some embodiments, infrared light may be upconverted to ultraviolet light (e.g., Mendioroz et al., Optical Materials, 26:351-357 (2004). In some embodiments, one or more photolyzable nitric oxide donors 108 may be associated with one or more rare-earth materials (e.g., ytterbium-erbium, ytterbium-thulium, or the like) that facilitate upconversion of energy (e.g., U.S. Pat. No. 7,088,040; herein incorporated by reference). For example, in some embodiments, one or more photolyzable nitric oxide donors 108 may be associated with $Nd^{3+}$ doped $KPb_2Cl_5$ crystals. In some embodiments, one or more photolyzable nitric oxide donors 108 may be associated with thiogallates doped with rare earths, such as $CaGa_2S_4:Ce^{3+}$ and $SrGa_2S_4:Ce^{3+}$. In some embodiments, one or more photolyzable nitric oxide donors 108 may be associated with aluminates that are doped with rare earths, such as $YAlO_3:Ce^{3+}$, $YGaO_3:Ce^{3+}$, $Y(Al,Ga)O_3:Ce^{3+}$, and orthosilicates $M_2SiO_5:Ce^{3+}$ (M:Sc, Y, Sc) doped with rare earths, such as, for example, $Y_2SiO_5:Ce^{3+}$. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

At embodiment 1108, module 930 may include one or more photolyzable nitric oxide donors that are coupled to one or more polymeric materials. In some embodiments, one or more photolyzable nitric oxide donors 108 may include one or more photolyzable nitric oxide donors 108 that are coupled to one or more polymeric materials. For example, in some embodiments, one or more polymer matrices may be impregnated with one or more photolyzable nitric oxide donors 108 (e.g., U.S. Pat. No. 5,994,444). In some embodiments, one or more photolyzable nitric oxide donors 108 may be bound to a polymer. Methods that can be used to couple nitric oxide donors to a polymeric matrix have been reported (e.g., U.S. Pat. No. 5,405,919). In some embodiments, one or more photolyzable nitric oxide donors 108 may be coupled to polymeric materials used to produce condoms 102. Accordingly, in some embodiments, one or more photolyzable nitric oxide donors 108 may be coupled to a condom 102.

Figure 12:
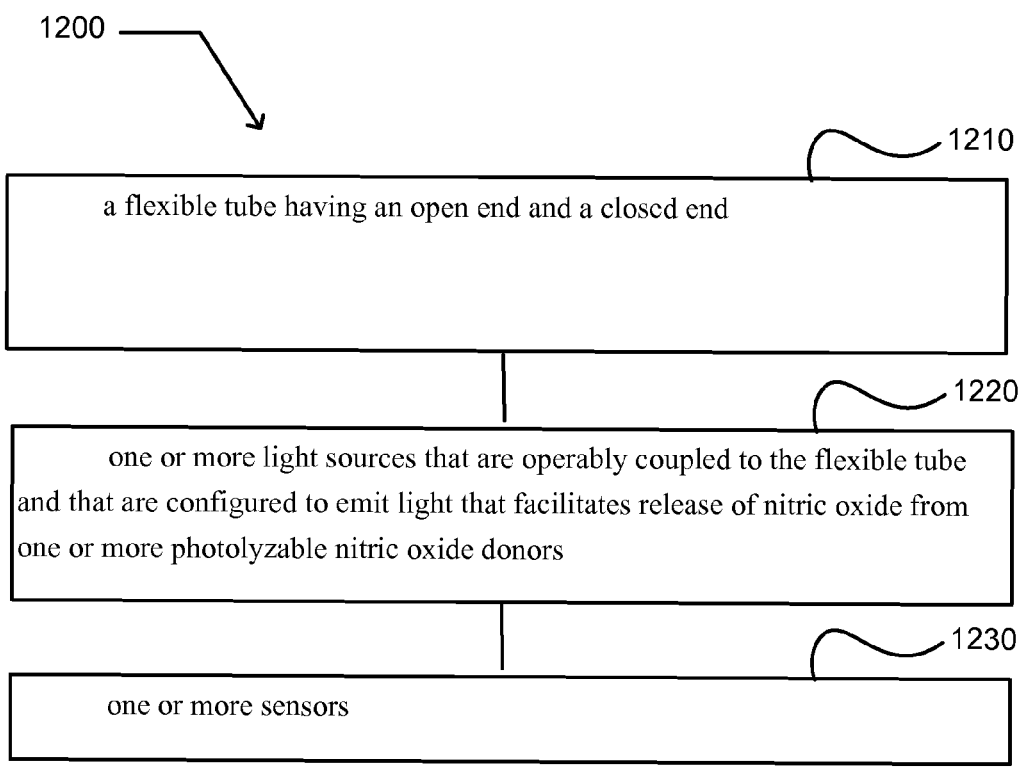
FIG. 12 illustrates embodiment 1200 of condom 102 within system 100.

FIG. 12 illustrates embodiment 1200 of condom 102 within system 100. In FIG. 12, discussion and explanation may be provided with respect to the above-described example of FIG. 1, and/or with respect to other examples and contexts. In some embodiments, modules 210 and 220 as described with respect to embodiment 200 of condom 102 of FIG. 2 may correspond to modules 1210 and 1220 as described with respect to embodiment 1200 of condom 102 within system 100. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 1200 may include module 1210 that includes a flexible tube having an open end and a closed end. In some embodiments, a condom 102 may include a flexible tube 104 having an open end and a closed end. In some embodiments, a flexible tube 104 may include one layer of elastomeric material. In some embodiments, a flexible tube 104 may include one or more layers of elastomeric material. For example, in some embodiments, a flexible tube 104 may be constructed of a single layer of latex rubber. In some embodiments, a flexible tube 104 may be constructed of a single layer of polyethylene. In some embodiments, a flexible tube 104 may be constructed of two or more laminated layers. For example, in some embodiments, a flexible tube 104 may include an inner layer that is constructed from polyethylene and an outer layer that is made from latex and laminated onto the inner layer. In some embodiments, a flexible tube 104 may include an inner layer that is a nitric oxide permeable layer 112 and an outer layer that is a nitric oxide impermeable layer. In some embodiments, a flexible tube 104 may include an inner layer that is a nitric oxide permeable layer, an outer layer that is a nitric oxide impermeable layer, and one or more photolyzable nitric oxide donors 108 positioned between the inner layer and the outer layer. In some embodiments, a flexible tube 104 may include one or more spermicidal agents. In some embodiments, one or more spermicidal agents may be associated with one or more portions of an interior surface of a flexible tube 104. In some embodiments, one or more spermicidal agents may be associated with one or more portions of an exterior surface of a flexible tube 104. In some embodiments, one or more spermicidal agents may be associated with one or more portions of an interior surface and one or more portions of an external surface of a flexible tube 104. In some embodiments, a flexible tube 104 may include one or more antimicrobial agents. In some embodiments, one or more antimicrobial agents may be associated with one or more portions of an interior surface of a flexible tube 104. In some embodiments, one or more antimicrobial agents may be associated with one or more portions of an exterior surface of a flexible tube 104. In some embodiments, one or more antimicrobial agents may be associated with one or more portions of an interior surface and one or more portions of an external surface of a flexible tube 104. In some embodiments, a flexible tube 104 may include one or more antiviral agents. In some embodiments, one or more antiviral agents may be associated with one or more portions of an interior surface of a flexible tube 104. In some embodiments, one or more antiviral agents may be associated with one or more portions of an exterior surface of a flexible tube 104. In some embodiments, one or more antiviral agents may be associated with one or more portions of an interior surface and one or more portions of an external surface of a flexible tube 104.

A flexible tube 104 may be constructed through use of numerous processes. For example, in some embodiments, a flexible tube 104 may be constructed through a dipping process where a former is coated with one or more elastomeric materials. In some embodiments, a flexible tube 104 may be constructed through a spraying process where a former is spray coated with one or more elastomeric materials. In some embodiments, a flexible tube 104 may be constructed through a molding process where one or more elastomeric materials are introduced into a mold and cast into a flexible tube 104. Accordingly, numerous processes may be used to construct flexible tubes 104. In some embodiments, one or more light sources 106 may be applied to a form and then the form may be coated with one or more elastomeric materials to form a flexible tube 104 that is associated with one or more light sources 106. In some embodiments, one or more light sources 106 may be associated with a preformed flexible tube 104. Methods that may be used to construct a flexible tube 104 are known and have been described (e.g., U.S. Pat. Nos. 7,235,505; 6,983,751; 6,651,667; 6,308,708; 6,000,398; and 4,919,149).

The embodiment 1200 may include module 1220 that includes one or more light sources that are operably coupled to the flexible tube and that are configured to emit light that facilitates release of nitric oxide from one or more photolyzable nitric oxide donors. In some embodiments, a condom 102 may include one or more light sources 106 that are operably coupled to a flexible tube 104 and that are configured to emit light that facilitates release of nitric oxide from one or more photolyzable nitric oxide donors 108. A light source 106 may be configured in numerous ways. For example, in some embodiments, a light source 106 may include a chemiluminescent light source 106. In some embodiments, a light source 106 may include a phosphorescent light source 106. In some embodiments, a light source 106 may include a light emitter that is coupled to a power supply. For example, in some embodiments, a light source 106 may include one or more light emitting diodes that are coupled to one or more power supplies. Examples of power supplies include, but are not limited to, capacitors, batteries, electromagnetic receivers 114, and the like. In some embodiments, one or more light sources 106 may be configured to emit light that specifically facilitates release of nitric oxide from one or more photolyzable nitric oxide donors 108. For example, in some embodiments, one or more light sources 106 may be configured to emit one or more wavelengths of light that facilitate photodecomposition of one or more photolyzable nitric oxide donors 108. In some embodiments, one or more light sources 106 may be configured such that they do not emit one or more wavelengths of light that do not facilitate photodecomposition of one or more photolyzable nitric oxide donors 108. Accordingly, in some embodiments, one or more light sources 106 may be configured to emit light that is matched to one or more photolyzable nitric oxide donors 108 and causes photodecomposition of the one or more photolyzable nitric oxide donors 108. In some embodiments, one or more light sources 106 may be configured such that they do not emit light that cross-links biological structures (e.g., proteins) or that causes the formation of DNA adducts. Accordingly, in some embodiments, one or more light sources 106 may be configured to emit light that photolyzes one or more photolyzable nitric oxide donors 108 with reduced damage to surrounding tissue. For example, in some embodiments, one or more light sources 106 may be configured to emit visible light ($\lambda$=550 nm) to facilitate homolytic decomposition of S-nitrosoglutathione to generate nitric oxide (e.g., Singh et al., FEBS Letters, 360:47-51 (1995)). In some embodiments, ultraviolet light may be used to facilitate release of nitric oxide from one or more photolyzable nitric oxide donors 108. For example, in some embodiments, one or more light sources 106 may be configured to emit ultraviolet light ($\lambda$=355 nm) to release nitric oxide from S-nitrosothiols (e.g., Rotta et al., Braz. J. Med. Biol. Res., 36:587-594 (2003)). In some embodiments, one or more light sources 106 may be configured to emit light over a broad range of wavelengths that will facilitate release of nitric oxide from one or more photolyzable nitric oxide donors 108. For example, in some embodiments, $O^2$-benzyl substituted diazeniumdiolates, $O^2$-napthylmethyl substituted diazeniumdiolates, and/or $O^2$-napththylallyl substituted diazeniumdiolates may be photolyzed by light over a broad range of wavelengths ($\lambda$=254 nm to $\lambda$=700 nm) (e.g., U.S. Pat. No. 7,122,529).

The embodiment 1200 may include module 1230 that includes one or more sensors. In some embodiments, a condom 102 may include one or more sensors 110. Numerous types of sensors 110 may be associated with a condom 102. In some embodiments, one or more sensors 110 may be used to determine the presence of nitric oxide in one or more tissues. In some embodiments, a sensor 110 may be configured for use on the outside surface of an individual 126. For example, in some embodiments, one or more sensors 110 may be configured to detect the concentration of nitric oxide on the penile surface. In some embodiments, one or more sensors 110 may be configured to be included within a flexible tube 104. For example, in some embodiments, one or more sensors 110 may be configured to be included within one or more collars that are associated with a flexible tube 104. In some embodiments, one or more sensors 110 may be configured to be included within one or more nitric oxide permeable layers 112. In some embodiments, a sensor 110 may be configured to utilize fluorescence to detect nitric oxide. For example, in some embodiments, a sensor 110 may detect nitric oxide through use of one or more fluorescent probes, such as 4,5-diaminofluorescein diacetate (EMD Chemicals Inc., San Diego, Calif.). In some embodiments, a sensor 110 may detect nitric oxide through use of one or more electrodes. For example, in some embodiments, a sensor 110 may utilize an electrode that includes a single walled carbon nanotube and an ionic liquid to detect nitric oxide (e.g., Li et al., Electroanalysis, 18:713-718 (2006)). Numerous sensors 110 are commercially available and have been described (e.g., World Precision Instruments, Inc., Sarasota, Florida, USA; U.S. Pat. Nos. 6,100,096; 6,280,604; 5,980,705). In some embodiments, a sensor 110 may include one or more transmitters. In some embodiments, a sensor 110 may include one or more receivers. In some embodiments, a sensor 110 may be configured to transmit one or more signals 120. In some embodiments, a sensor 110 may be configured to receive one or more signals 120.

Numerous types of sensors 110 may be associated with a condom 102. Examples of such sensors 110 include, but are not limited to, temperature sensors 110, pressure sensors 110 (e.g., blood pressure, hydrostatic pressure), pulse rate sensors 110, clocks, strain sensors 110, light sensors 110, nitric oxide sensors 110, and the like.

Figure 13:
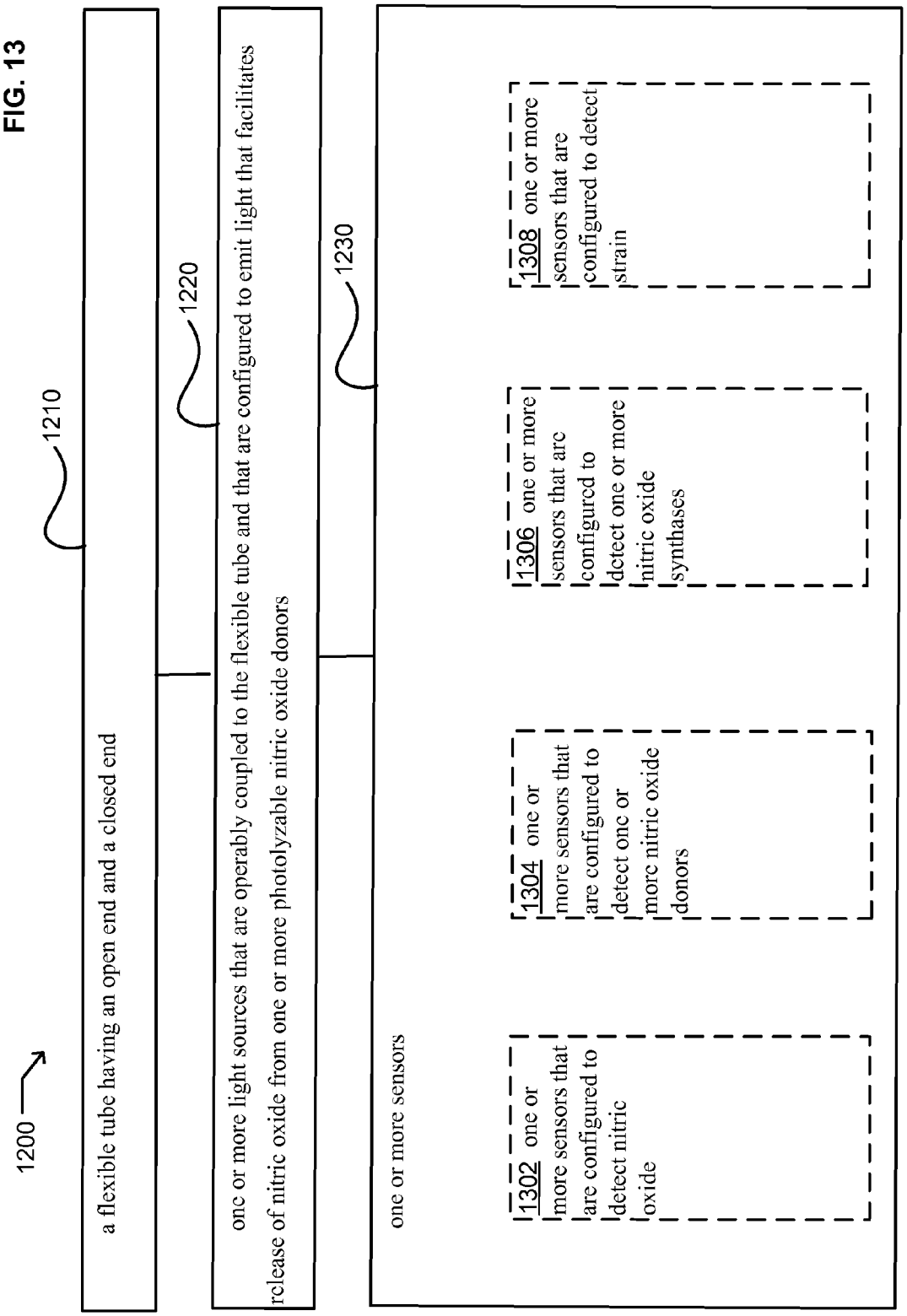
FIG. 13 illustrates alternate embodiments of module 1230 of embodiment 1200 of condom 102 within system 100.

FIG. 13 illustrates alternative embodiments of embodiment 1200 of condom 102 within system 100 of FIG. 12. FIG. 13 illustrates example embodiments of module 1230 of condom 102. Additional embodiments may include an embodiment 1302, an embodiment 1304, an embodiment 1306, and/or an embodiment 1308.

At embodiment 1302, module 1230 may include one or more sensors that are configured to detect nitric oxide. In some embodiments, one or more sensors 110 may include one or more sensors 110 that are configured to detect nitric oxide. Sensors 110 may be configured in numerous ways. In some embodiments, a sensor 110 may be configured to utilize fluorescence to detect nitric oxide. For example, in some embodiments, a sensor 110 may detect nitric oxide through use of one or more fluorescent probes, such as 4,5-diaminofluorescein diacetate (EMD Chemicals Inc., San Diego, Calif.). In some embodiments, a sensor 110 may detect nitric oxide through use of one or more electrodes. For example, in some embodiments, a sensor 110 may utilize an electrode that includes a single walled carbon nanotube and an ionic liquid to detect nitric oxide (e.g., Li et al., Electroanalysis, 18:713-718 (2006)). Numerous sensors 110 are commercially available and have been described (e.g., World Precision Instruments, Inc., Sarasota, Fla., USA; U.S. Pat. Nos. 6,100,096; 6,280,604; 5,980,705).

At embodiment 1304, module 1230 may include one or more sensors that are configured to detect one or more nitric oxide donors. In some embodiments, one or more sensors 110 may include one or more sensors 110 that are configured to detect one or more nitric oxide donors. In some embodiments, one or more sensors 110 may include one or more surface plasmon resonance chemical electrodes that are configured to detect one or more nitric oxide donors. For example, in some embodiments, one or more sensors 110 may include one or more surface plasmon resonance chemical electrodes that include antibodies and/or aptamers that bind to one or more nitric oxide donors. Accordingly, such electrodes may be used to detect the one or more nitric oxide donors through use of surface plasmon resonance. Methods to construct surface plasmon resonance chemical electrodes are known and have been described (e.g., U.S. Pat. No. 5,858,799; Lin et al., Applied Optics, 46:800-806 (2007)). In some embodiments, antibodies and/or aptamers that bind to one or more nitric oxide donors may be used within one or more micro-electro-mechanical systems to detect one or more nitric oxide donors. Methods to construct micro-electro-mechanical detectors have been described (e.g., Gau et al., Biosensors & Bioelectronics, 16:745-755 (2001)).

At embodiment 1306, module 1230 may include one or more sensors that are configured to detect one or more nitric oxide synthases. In some embodiments, one or more sensors 110 may include one or more sensors 110 that are configured to detect one or more nitric oxide synthases. In some embodiments, one or more sensors 110 may be configured to detect nitric oxide synthase activity. Nitric oxide synthase detection kits are commercially available (e.g., Cell Technology, Inc., Mountain View, Calif.). In some embodiments, one or more sensors 110 may be configured to detect nitric oxide synthase messenger ribonucleic acid (mRNA). Methods that may be used to detect such mRNA have been reported (e.g., Sonoki et al., Leukemia, 13:713-718 (1999)). In some embodiments, one or more sensors 110 may be configured to detect nitric oxide synthase through immunological methods. Methods that may be used to detect nitric oxide synthase directly been reported (e.g., Burrell et al., J. Histochem. Cytochem., 44:339-346 (1996) and Hattenbach et al., Ophthalmologica, 216:209-214 (2002)). In some embodiments, micro-electro-mechanical systems may be used to detect nitric oxide synthase. In some embodiments, antibodies and/or aptamers that bind to nitric oxide synthase may be used within one or more micro-electro-mechanical systems to detect nitric oxide synthase. Methods to construct micro-electro-mechanical detectors have been described (e.g., Gau et al., Biosensors & Bioelectronics, 16:745-755 (2001)). Accordingly, sensors 110 may be configured in numerous ways to detect one or more nitric oxide synthases.

At embodiment 1308, module 1230 may include one or more sensors that are configured to detect strain. In some embodiments, one or more sensors 110 may include one or more sensors 110 that are configured to detect strain. In some embodiments, a condom 102 may be configured to include one or more strain gauges. Strain gauges may be configured in numerous ways. For example, in some embodiments, one or more strain gauges may be configured to measure strain along the length of a flexible tube 104. In some embodiments, one or more strain gauges may be configured to measure strain that is substantially perpendicular to the length of a flexible tube 104. In some embodiments, one or more strain gauges may be configured to measure strain that is substantially diagonal to the length of a flexible tube 104. In some embodiments, one or more strain gauges may be configured to measure strain along numerous axis relative to the length of a flexible tube 104. In some embodiments, a Wheatstone bridge circuit may be used to convert a gauge's microstrain into a voltage change that can be detected. In some embodiments, a variable capacitor may be used to construct a strain gauge. Accordingly, numerous types of strain gauges may be associated with a condom 102.

Figure 14:
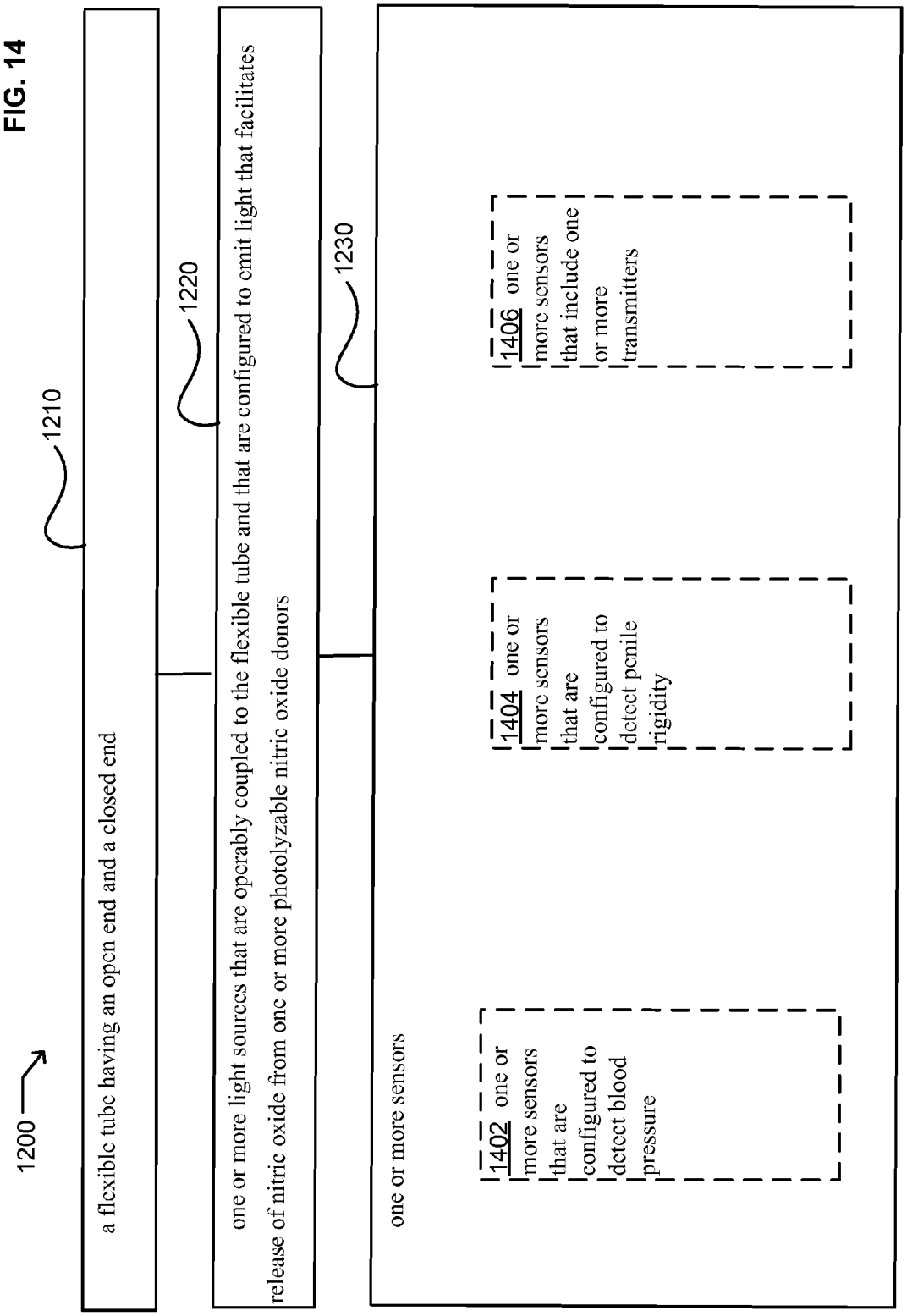
FIG. 14 illustrates alternate embodiments of module 1230 of embodiment 1200 of condom 102 within system 100.

FIG. 14 illustrates alternative embodiments of embodiment 1200 of condom 102 within system 100 of FIG. 12. FIG. 14 illustrates example embodiments of module 1230 of condom 102. Additional embodiments may include an embodiment 1402, an embodiment 1404, and/or an embodiment 1406.

At embodiment 1402, module 1230 may include one or more sensors that are configured to detect blood pressure. In some embodiments, one or more sensors 110 may include one or more sensors 110 that are configured to detect blood pressure. In some embodiments, one or more sensors 110 may be configured to detect blood pressure through use of an oscillometric method in which an electronic pressure sensor 110 may be used to measure blood flow. In some embodiments, one or more sensors 110 may be coupled with one or more collars that are associated with a flexible tube 104 to measure blood flow.

At embodiment 1404, module 1230 may include one or more sensors that are configured to detect penile rigidity. In some embodiments, one or more sensors 110 may include one or more sensors 110 that are configured to detect penile rigidity. For example, in some embodiments, one or more sensors 110 may include one or more strain gauges that are associated with a flexible tube 104. Accordingly, such strain gauges may be configured to detect penile rigidity when a condom 102 is applied to a penis through measurement of strain associated with the flexible tube 104. In some embodiments, strain may be determined along the length of the tube. In some embodiments, strain may be determined perpendicular to the length of the tube (e.g., strain occurring in one or more collars that are associated with a flexible tube 104 that surround the penis).

At embodiment 1406, module 1230 may include one or more sensors that include one or more transmitters. In some embodiments, one or more sensors 110 may include one or more sensors 110 that include one or more transmitters. Accordingly, in some embodiments, one or more sensors 110 may transmit one or more signals 120 that include information associated with penile rigidity, nitric oxide concentration, pressure, and the like.

Figure 15:
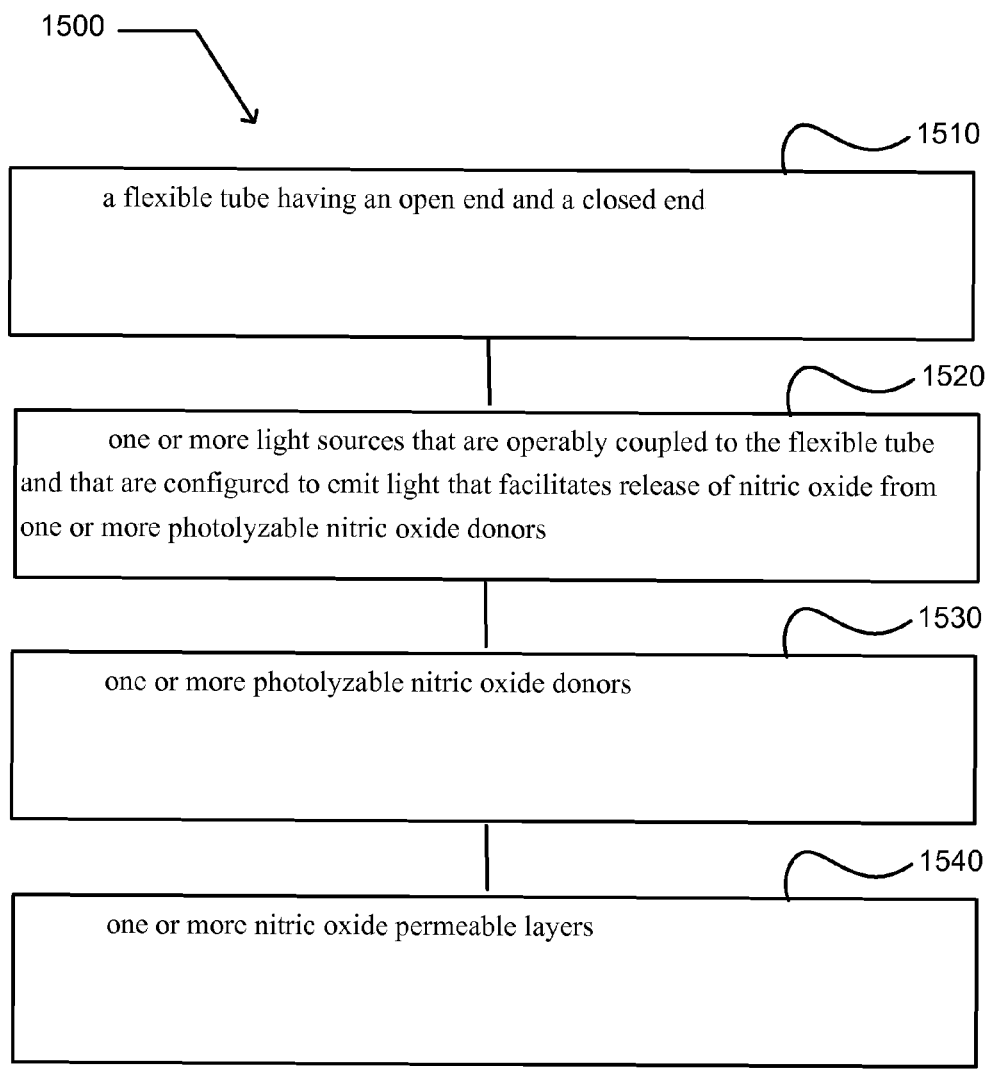
FIG. 15 illustrates embodiment 1500 of condom 102 within system 100.

FIG. 15 illustrates embodiment 1500 of condom 102 within system 100. In FIG. 15, discussion and explanation may be provided with respect to the above-described example of FIG. 1, and/or with respect to other examples and contexts. In some embodiments, modules 210 and 220 as described with respect to embodiment 200 of condom 102 of FIG. 2 may correspond to modules 1510 and 1520 as described with respect to embodiment 1500 of condom 102 within system 100. In some embodiments, module 930 as described with respect to embodiment 900 of condom 102 of FIG. 9 may correspond to module 1530 as described with respect to embodiment 1500 of condom 102 within system 100. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 1500 may include module 1510 that includes a flexible tube having an open end and a closed end. In some embodiments, a condom 102 may include a flexible tube 104 having an open end and a closed end. In some embodiments, a flexible tube 104 may include one layer of elastomeric material. In some embodiments, a flexible tube 104 may include one or more layers of elastomeric material. For example, in some embodiments, a flexible tube 104 may be constructed of a single layer of latex rubber. In some embodiments, a flexible tube 104 may be constructed of a single layer of polyethylene. In some embodiments, a flexible tube 104 may be constructed of two or more laminated layers. For example, in some embodiments, a flexible tube 104 may include an inner layer that is constructed from polyethylene and an outer layer that is made from latex and laminated onto the inner layer. In some embodiments, a flexible tube 104 may include an inner layer that is a nitric oxide permeable layer 112 and an outer layer that is a nitric oxide impermeable layer. In some embodiments, a flexible tube 104 may include an inner layer that is a nitric oxide permeable layer 112, an outer layer that is a nitric oxide impermeable layer, and one or more photolyzable nitric oxide donors 108 positioned between the inner layer and the outer layer. In some embodiments, a flexible tube 104 may include one or more spermicidal agents. In some embodiments, one or more spermicidal agents may be associated with one or more portions of an interior surface of a flexible tube 104. In some embodiments, one or more spermicidal agents may be associated with one or more portions of an exterior surface of a flexible tube 104. In some embodiments, one or more spermicidal agents may be associated with one or more portions of an interior surface and one or more portions of an external surface of a flexible tube 104. In some embodiments, a flexible tube 104 may include one or more antimicrobial agents. In some embodiments, one or more antimicrobial agents may be associated with one or more portions of an interior surface of a flexible tube 104. In some embodiments, one or more antimicrobial agents may be associated with one or more portions of an exterior surface of a flexible tube 104. In some embodiments, one or more antimicrobial agents may be associated with one or more portions of an interior surface and one or more portions of an external surface of a flexible tube 104. In some embodiments, a flexible tube 104 may include one or more antiviral agents. In some embodiments, one or more antiviral agents may be associated with one or more portions of an interior surface of a flexible tube 104. In some embodiments, one or more antiviral agents may be associated with one or more portions of an exterior surface of a flexible tube 104. In some embodiments, one or more antiviral agents may be associated with one or more portions of an interior surface and one or more portions of an external surface of a flexible tube 104.

A flexible tube 104 may be constructed through use of numerous processes. For example, in some embodiments, a flexible tube 104 may be constructed through a dipping process where a former is coated with one or more elastomeric materials. In some embodiments, a flexible tube 104 may be constructed through a spraying process where a former is spray coated with one or more elastomeric materials. In some embodiments, a flexible tube 104 may be constructed through a molding process where one or more elastomeric materials are introduced into a mold and cast into a flexible tube 104. Accordingly, numerous processes may be used to construct flexible tubes 104. In some embodiments, one or more light sources 106 may be applied to a form and then the form may be coated with one or more elastomeric materials to form a flexible tube 104 that is associated with one or more light sources 106. In some embodiments, one or more light sources 106 may be associated with a preformed flexible tube 104. Methods that may be used to construct a flexible tube 104 are known and have been described (e.g., U.S. Pat. Nos. 7,235,505; 6,983,751; 6,651,667; 6,308,708; 6,000,398; and 4,919,149).

The embodiment 1500 may include module 1520 that includes one or more light sources that are operably coupled to the flexible tube and that are configured to emit light that facilitates release of nitric oxide from one or more photolyzable nitric oxide donors. In some embodiments, a condom 102 may include one or more light sources 106 that are operably coupled to a flexible tube 104 and that are configured to emit light that facilitates release of nitric oxide from one or more photolyzable nitric oxide donors 108. A light source 106 may be configured in numerous ways. For example, in some embodiments, a light source 106 may include a chemiluminescent light source 106. In some embodiments, a light source 106 may include a phosphorescent light source 106. In some embodiments, a light source 106 may include a light emitter that is coupled to a power supply. For example, in some embodiments, a light source 106 may include one or more light emitting diodes that are coupled to one or more power supplies. Examples of power supplies include, but are not limited to, capacitors, batteries, electromagnetic receivers 114, and the like. In some embodiments, one or more light sources 106 may be configured to emit light that specifically facilitates release of nitric oxide from one or more photolyzable nitric oxide donors 108. For example, in some embodiments, one or more light sources 106 may be configured to emit one or more wavelengths of light that facilitate photodecomposition of one or more photolyzable nitric oxide donors 108. In some embodiments, one or more light sources 106 may be configured such that they do not emit one or more wavelengths of light that do not facilitate photodecomposition of one or more photolyzable nitric oxide donors 108. Accordingly, in some embodiments, one or more light sources 106 may be configured to emit light that is matched to one or more photolyzable nitric oxide donors 108 and causes photodecomposition of the one or more photolyzable nitric oxide donors 108. In some embodiments, one or more light sources 106 may be configured such that they do not emit light that cross-links biological structures (e.g., proteins) or that causes the formation of DNA adducts. Accordingly, in some embodiments, one or more light sources 106 may be configured to emit light that photolyzes one or more photolyzable nitric oxide donors 108 with reduced damage to surrounding tissue. For example, in some embodiments, one or more light sources 106 may be configured to emit visible light ($\lambda=550$ nm) to facilitate homolytic decomposition of S-nitrosoglutathione to generate nitric oxide (e.g., Singh et al., FEBS Letters, 360:47-51 (1995)). In some embodiments, ultraviolet light may be used to facilitate release of nitric oxide from one or more photolyzable nitric oxide donors 108. For example, in some embodiments, one or more light sources 106 may be configured to emit ultraviolet light ($\lambda$=355 nm) to release nitric oxide from S-nitrosothiols (e.g., Rotta et al., Braz. J. Med. Biol. Res., 36:587-594 (2003)). In some embodiments, one or more light sources 106 may be configured to emit light over a broad range of wavelengths that will facilitate release of nitric oxide from one or more photolyzable nitric oxide donors 108. For example, in some embodiments, $O^2$-benzyl substituted diazeniumdiolates, $O^2$-napthylmethyl substituted diazeniumdiolates, and/or $O^2$-napththylallyl substituted diazeniumdiolates may be photolyzed by light over a broad range of wavelengths ($\lambda$=254 nm to $\lambda$=700 nm) (e.g., U.S. Pat. No. 7,122,529).

The embodiment 1500 may include module 1530 that includes one or more photolyzable nitric oxide donors. In some embodiments, a condom 102 may include one or more photolyzable nitric oxide donors 108. Examples of such photolyzable nitric oxide donors 108 include, but are not limited to, diazeniumdiolates (e.g., U.S. Pat. Nos. 7,105,502; 7,122,529; 6,673,338; herein incorporated by reference), trans-[RuCl([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550:819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference).

The embodiment 1500 may include module 1540 that includes one or more nitric oxide permeable layers. In some embodiments, a condom 102 may include one or more nitric oxide permeable layers 112. A condom 102 may include one or more nitric oxide permeable layers 112 that are fabricated from numerous types of material. Examples of such materials include, but are not limited to, ceramics, polymeric materials, metals, plastics, and the like. In some embodiments, one or more nitric oxide permeable layers 112 may include numerous combinations of materials. For example, in some embodiments, a nitric oxide permeable layer 112 may include a nitric oxide impermeable material that is coupled to a nitric oxide permeable material. In some embodiments, a nitric oxide permeable layer 112 may include one or more nitric oxide permeable membranes (e.g., U.S. Patent Application No. 20020026937). In some embodiments, a nitric oxide permeable layer 112 may include a selectively permeable membrane. For example, in some embodiments, a nitric oxide permeable layer 112 may include a selectively permeable membrane that is a hydrophilic polyester co-polymer membrane system that includes a copolymer with 70% polyester and 30% polyether (e.g., Sympatex™ 10 μm membrane, see Hardwick et al., Clinical Science, 100:395-400 (2001)). In some embodiments, a nitric oxide permeable layer 112 may include a nitric oxide permeable coating (e.g., U.S. Patent Application Nos. 20050220838 and 20030093143).

In some embodiments, one or more nitric oxide permeable layers 112 may form the interior surface of a flexible tube 104 forming a condom 102. In some embodiments, one or more nitric oxide permeable layers 112 may be included in one or more portions of a flexible tube 104 forming a condom 102. For example, in some embodiments, a flexible tube 104 may include one or more nitric oxide permeable portions that facilitate release of nitric oxide to the interior of a condom 102 that includes the nitric oxide permeable layer 112.

In some embodiments, one or more nitric oxide permeable layers 112 may be configured to enclose at least a portion of one or more photolyzable nitric oxide donors 108. In some embodiments, one or more nitric oxide permeable layers 112 may be configured to enclose at least a portion of one or more light sources 106, at least a portion of one or more sensors 110, at least a portion of one or more electromagnetic receivers 114, or substantially any combination thereof.

Figure 16:
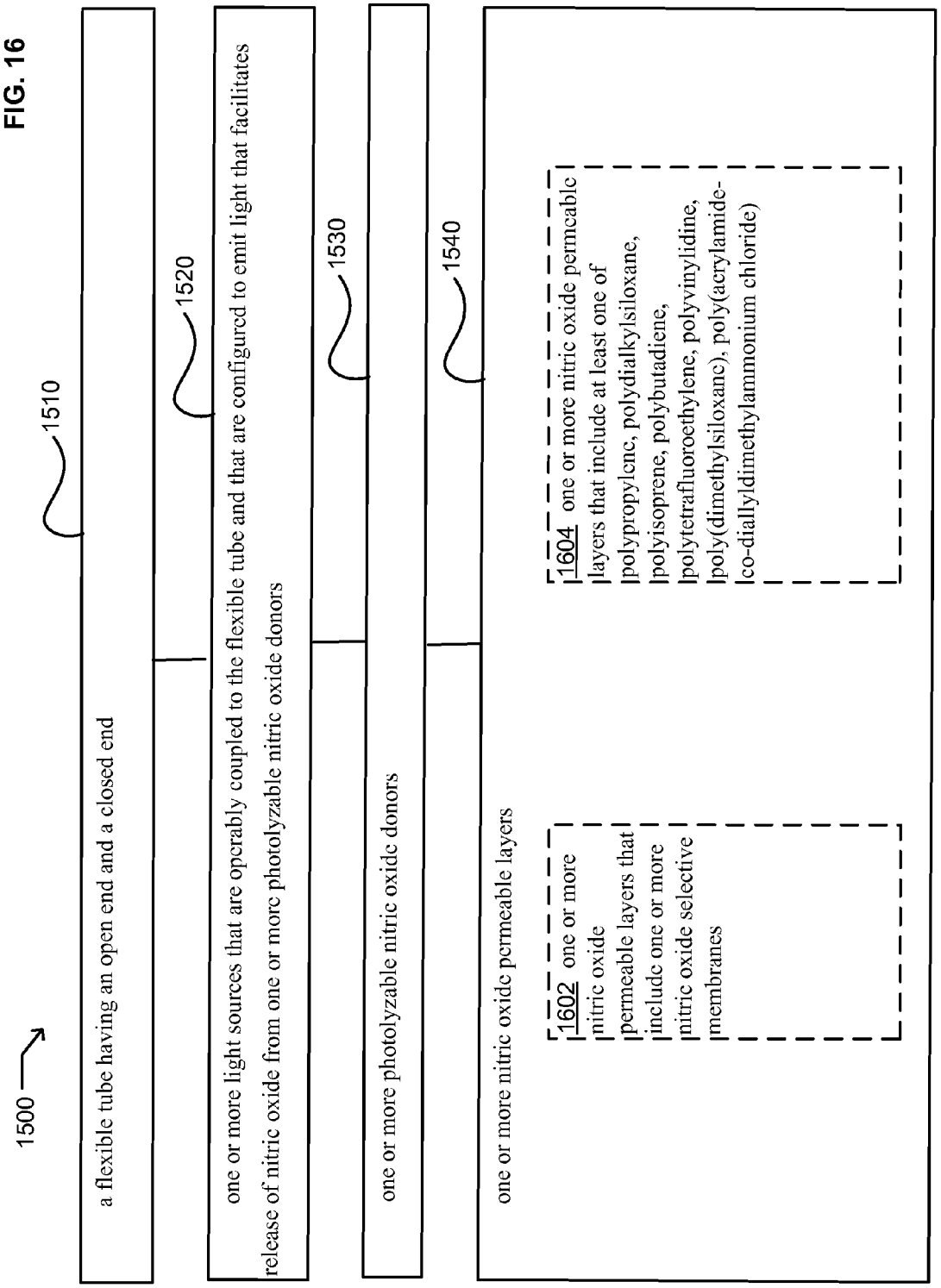
FIG. 16 illustrates alternate embodiments of module 1540 of embodiment 1500 of condom 102 within system 100.

FIG. 16 illustrates alternative embodiments of embodiment 1500 of condom 102 within system 100 of FIG. 15. FIG. 16 illustrates example embodiments of module 1540 of condom 102. Additional embodiments may include an embodiment 1602 and/or an embodiment 1604.

At embodiment 1602, module 1540 may include one or more nitric oxide permeable layers that include one or more nitric oxide selective membranes. In some embodiments, one or more nitric oxide permeable layers 112 may include one or more nitric oxide permeable layers 112 that include one or more nitric oxide selective membranes. In some embodiments, a nitric oxide permeable layer 112 may include a selectively permeable membrane. For example, in some embodiments, a nitric oxide permeable layer 112 may include a selectively permeable membrane that is a hydrophilic polyester co-polymer membrane system that includes a copolymer with 70% polyester and 30% polyether (e.g., Sympatex™ 10 μm membrane, see Hardwick et al., Clinical Science, 100:395-400 (2001)). Methods to fabricate nitric oxide permeable membranes are known (e.g., U.S. Patent Application No. 20020026937).

At embodiment 1604, module 1540 may include one or more nitric oxide permeable layers that include at least one of polypropylene, polydialkylsiloxane, polyisoprene, polybutadiene, polytetrafluoroethylene, polyvinylidine, poly(dimethylsiloxane), poly(acrylamide-co-diallyldimethylammonium chloride). In some embodiments, one or more nitric oxide permeable layers 112 may include one or more nitric oxide permeable layers 112 that include at least one of polypropylene, polydialkylsiloxane, polyisoprene, polybutadiene, polytetrafluoroethylene, polyvinylidine, poly(dimethylsiloxane), poly(acrylamide-co-diallyldimethylammonium chloride).

Figure 17:
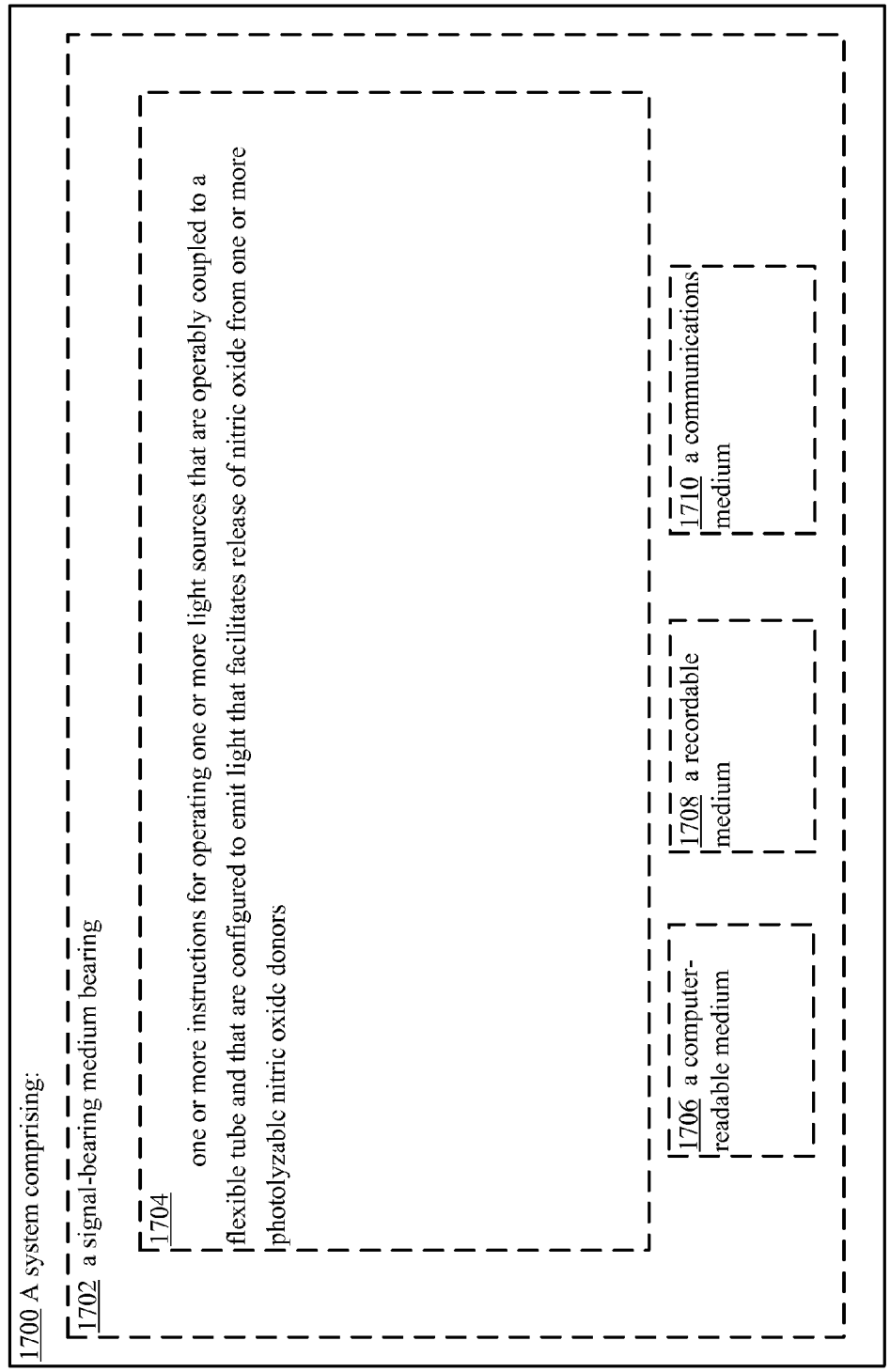
FIG. 17 illustrates a partial view of a system 1700 that includes a computer program for executing a computer process on a computing device.

FIG. 17 illustrates a partial view of a system 1700 that includes a computer program 1704 for executing a computer process on a computing device. An embodiment of system 1700 is provided using a signal-bearing medium 1702 bearing one or more instructions for operating one or more light sources that are operably coupled to a flexible tube 104 and that are configured to emit light that facilitates release of nitric oxide from one or more photolyzable nitric oxide donors 108. The one or more instructions may be, for example, computer executable and/or logic-implemented instructions. In some embodiments, the signal-bearing medium 1702 may include a computer-readable medium 1706. In some embodiments, the signal-bearing medium 1702 may include a recordable medium 1708. In some embodiments, the signal-bearing medium 1702 may include a communications medium 1710.

FIG. 18 illustrates a partial view of a system 1800 that includes a computer program 1804 for executing a computer process on a computing device. An embodiment of system 1800 is provided using a signal-bearing medium 1802 bearing one or more instructions for operating one or more light sources that are operably coupled to a flexible tube 104 and that are configured to emit light that facilitates release of nitric oxide from one or more photolyzable nitric oxide donors 108 and one or more instructions for operating one or more sensors 110. The one or more instructions may be, for example, computer executable and/or logic-implemented instructions. In some embodiments, the signal-bearing medium 1802 may include a computer-readable medium 1806. In some embodiments, the signal-bearing medium 1802 may include a recordable medium 1808. In some embodiments, the signal-bearing medium 1802 may include a communications medium 1810.

Figure 19:
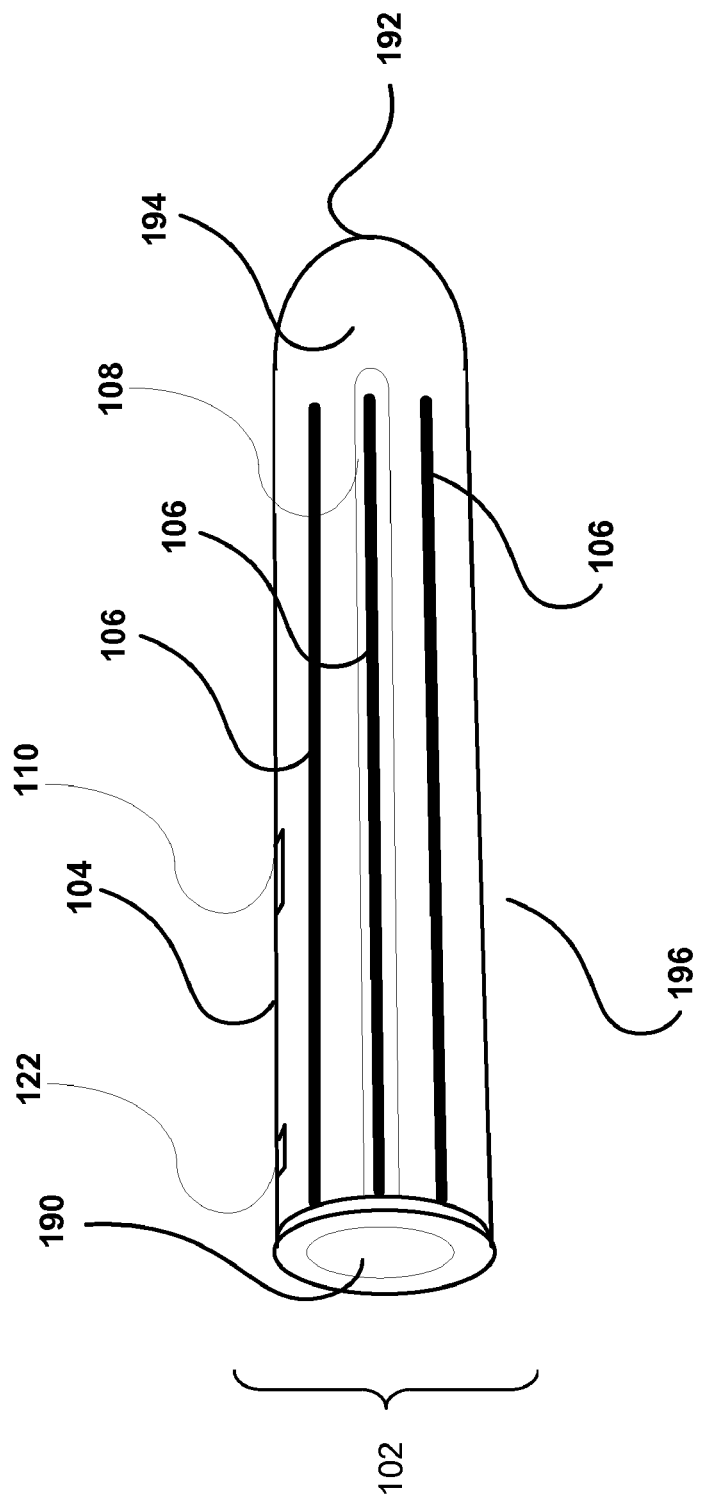
FIG. 19 illustrates an embodiment of condom 102 within system 100.

FIG. 19 illustrates an embodiment of condom 102. A flexible tube 104 is shown in association with light sources 106. Flexible tube 104 includes an open end 190 and a closed end 192. Flexible tube 104 includes an interior space 194 and an exterior space 196.

Figure 20:
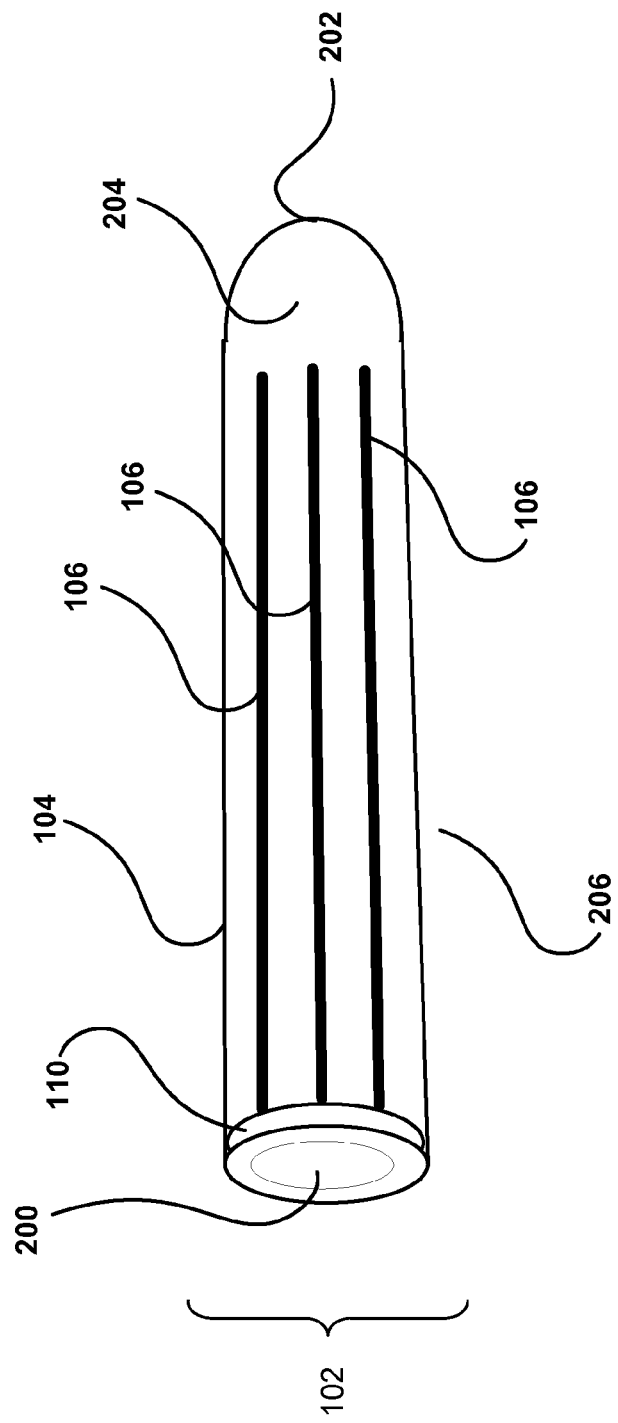
FIG. 20 illustrates an embodiment of condom 102 within system 100.

FIG. 20 illustrates an embodiment of condom 102. A flexible tube 104 is shown in association with light sources 106. Flexible tube 104 includes an open end 200 and a closed end 202. Flexible tube 104 includes an interior space 204 and an exterior space 206. A sensor 110 is shown in association with flexible tube 104.

Figure 21:
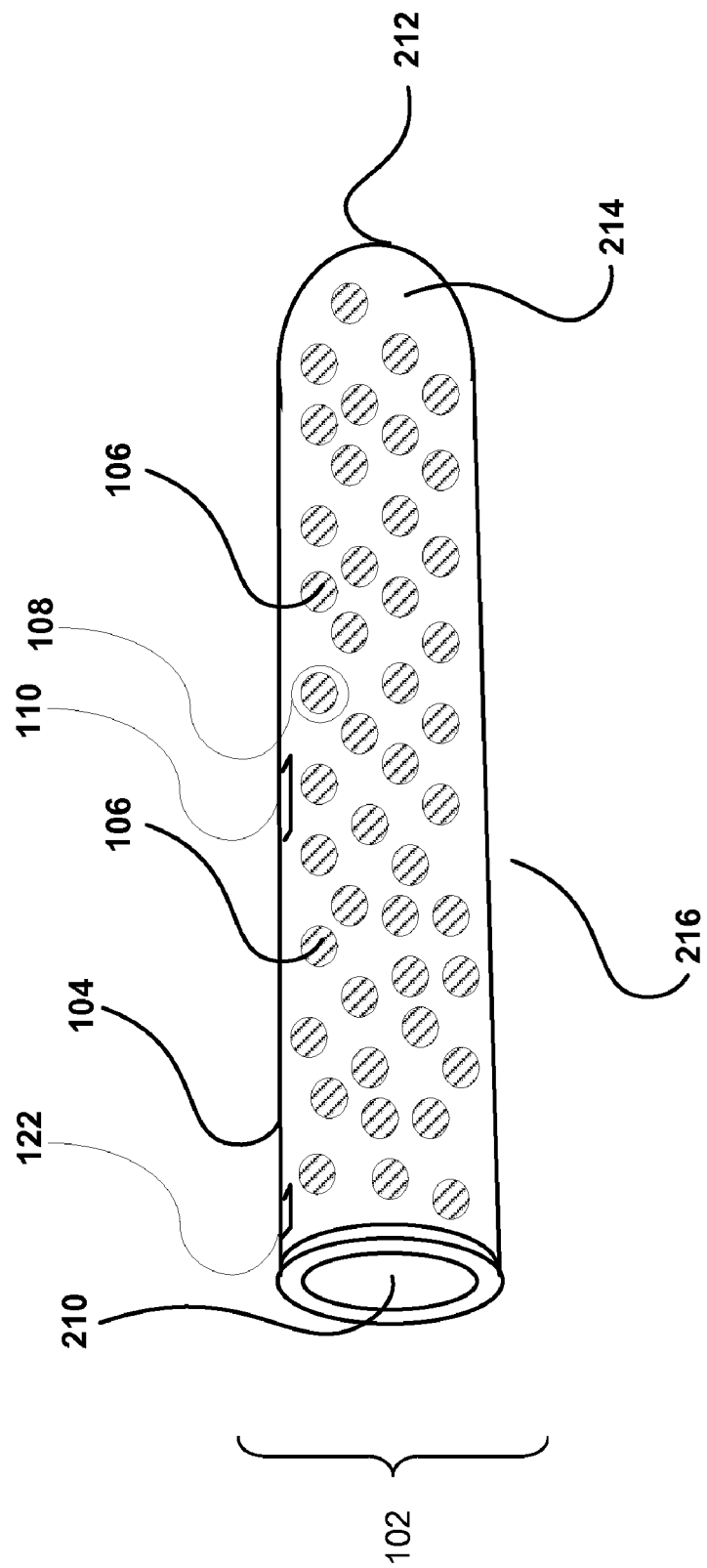
FIG. 21 illustrates an embodiment of condom 102 within system 100.

FIG. 21 illustrates an embodiment of condom 102. A flexible tube 104 is shown in association with light sources 106. Flexible tube 104 includes an open end 210 and a closed end 212. Flexible tube 104 includes an interior space 214 and an exterior space 216.

Figure 22:
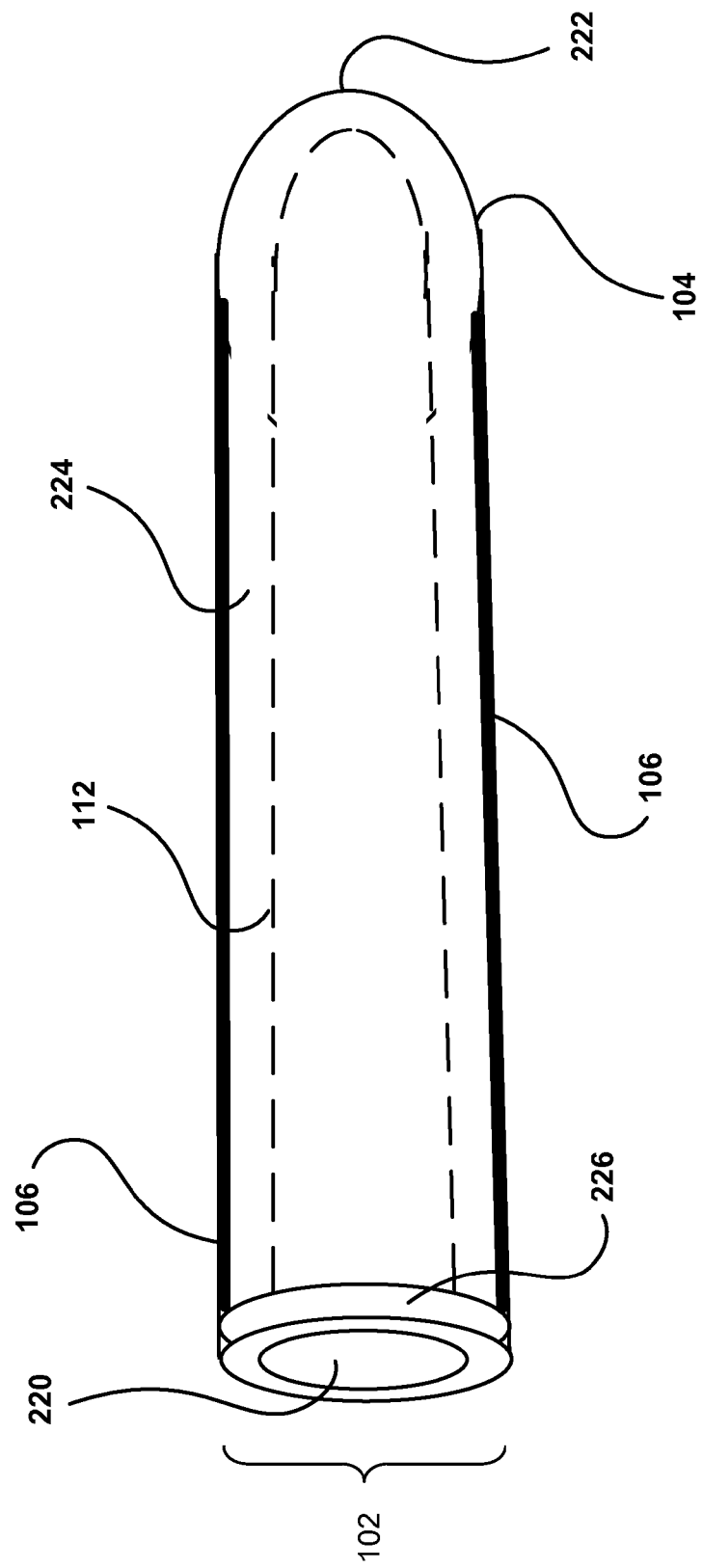
FIG. 22 illustrates an embodiment of condom 102 within system 100.

FIG. 22 illustrates an embodiment of condom 102. A flexible tube 104 is shown in association with light sources 106. Flexible tube 104 includes an open end 220 and a closed end 222. Flexible tube 104 includes a nitric oxide permeable layer 112 and a reservoir 224. A collar 226 is shown in association with the flexible tube 104.

Figure 23:
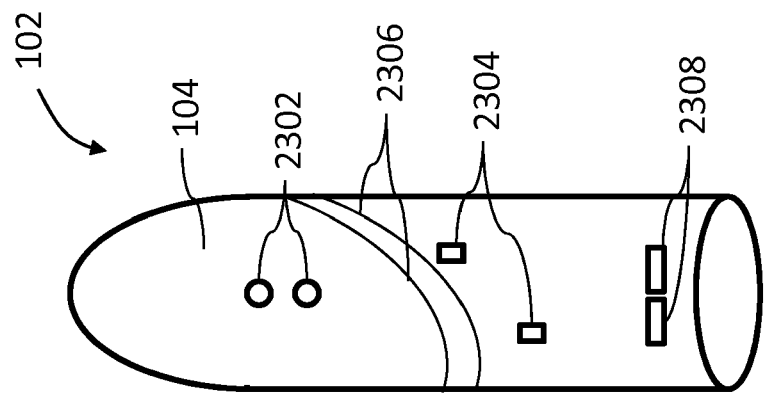
FIG. 23 illustrates an embodiment of condom 102 within system 100.

FIG. 23 illustrates an embodiment of condom 102. A flexible tube 104 is shown in association with one or more sensors 2302, one or more donors 2304, one or more waveguides 2306, and one or more transmitters and/or receivers 2308.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electromechanical systems include but are not limited to a variety of consumer electronics systems, as well as other systems such as motorized transport systems, factory automation systems, security systems, and communication/computing systems. Those skilled in the art will recognize that electromechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a voice-over IP system, etc.), (f) a business entity (e.g., an Internet Service Provider (ISP) entity such as Comcast Cable, Quest, Southwestern Bell, etc), or (g) a wired/wireless services entity (e.g., such as Sprint, Cingular, Nextel, etc.), etc.

Although the user interface 124 is shown/described herein as a single illustrated figure that is associated with an individual, those skilled in the art will appreciate that a user interface 124 may be utilized by a user that is a representative of a human user, a robotic user (e.g., computational entity), and/or substantially any combination thereof (e.g., a user may be assisted by one or more robotic based systems). In addition, a user as set forth herein, although shown as a single entity may in fact be composed of two or more entities. Those skilled in the art will appreciate that, in general, the same may be said of "sender" and/or other entity-oriented terms as such terms are used herein.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

What is claimed is:

1. A condom comprising:
   a flexible tube having an open end and a closed end;
   one or more sensors operably associated with one or more control units and configured to detect penile rigidity;
   one or more light sources configured to release light in response to one or more detected values of penile rigidity; and
   one or more photolyzable nitric oxide donors configured to release nitric oxide in response to light of at least one of the one or more light sources.

2. The condom of claim 1, further comprising:
   one or more optical waveguides.

3. The condom of claim 1, wherein the one or more light sources configured to release light in response to one or more detected values of penile rigidity comprises:
   one or more light emitters configured to release light in response to one or more detected values of penile rigidity.

4. The condom of claim 1, further comprising:
   one or more power supplies.

5. The condom of claim 1, further comprising:
   one or more electromagnetic receivers.

6. The condom of claim 1, further comprising:
   one or more quantum dots.

7. The condom of claim 1, further comprising:
   one or more rare-earth materials.

8. The condom of claim 1, further comprising:
   one or more fluorescent materials.

9. The condom of claim 1, wherein the one or more light sources configured to release light in response to one or more detected values of penile rigidity comprise:
   one or more light sources configured to release light that specifically facilitates release of nitric oxide in response to one or more detected values of penile rigidity.

10. The condom of claim 1, wherein the one or more light sources configured to release light in response to one or more detected values of penile rigidity comprise:
    one or more light sources configured to release light specifically selected to avoid tissue damage in response to one or more detected values of penile rigidity.

11. The condom of claim 1, further comprising:
    one or more transmitters.

12. The condom of claim 1, further comprising:
    one or more receivers.

13. The condom of claim 1, wherein the one or more photolyzable nitric oxide donors configured to release nitric oxide in response to light of at least one of the one or more light sources comprises:
    one or more photolyzable nitric oxide donors decoupled from the flexible tube and configured to release nitric oxide in response to light of at least one of the one or more light sources.

14. The condom of claim 1, wherein the one or more photolyzable nitric oxide donors configured to release nitric oxide in response to light of at least one of the one or more light sources comprises:
    one or more photolyzable nitric oxide donors that include one or more diazeniumdiolates configured to release nitric oxide in response to light of at least one of the one or more light sources.

15. The condom of claim 1, further comprising:
    one or more other sensors.

16. The condom of claim 1, further comprising:
    one or more sensors configured to detect nitric oxide.

17. The condom of claim 1, further comprising:
    one or more sensors configured to detect nitric oxide donors.

18. The condom of claim 1, further comprising:
    one or more nitric oxide permeable layers.

19. The condom of claim 1, further comprising:
    one or more nitric oxide permeable layers that include one or more nitric oxide selective membranes.

20. The condom of claim 1, wherein the one or more light sources configured to release light in response to one or more detected values of penile rigidity comprises:
    one or more light sources configured to release light in response to one or more detected values of penile rigidity and one or more detected values of nitric oxide.

* * * * *